(12) United States Patent
E et al.

(10) Patent No.: US 12,196,761 B2
(45) Date of Patent: *Jan. 14, 2025

(54) USE OF LC-MS/MS TO QUANTITATE PROTEIN BIOMARKERS

(71) Applicant: Regeneron Pharmaceuticals, Inc., Tarrytown, NY (US)

(72) Inventors: Sook Yen E, Croton-on-Hudson, NY (US); Haibo Qiu, Hartsdale, NY (US); Ning Li, New Canaan, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 8 days.

This patent is subject to a terminal disclaimer.

(21) Appl. No.: 18/175,066

(22) Filed: Feb. 27, 2023

(65) Prior Publication Data

US 2023/0366888 A1 Nov. 16, 2023

Related U.S. Application Data

(62) Division of application No. 16/534,095, filed on Aug. 7, 2019, now Pat. No. 11,592,449.

(60) Provisional application No. 62/715,973, filed on Aug. 8, 2018.

(51) Int. Cl.
G01N 33/68 (2006.01)
G16B 40/10 (2019.01)
G16H 50/30 (2018.01)

(52) U.S. Cl.
CPC ......... *G01N 33/6851* (2013.01); *G16B 40/10* (2019.02); *G16H 50/30* (2018.01)

(58) Field of Classification Search
None
See application file for complete search history.

(56) References Cited

U.S. PATENT DOCUMENTS

| 11,592,449 B2 | 2/2023 | E et al. |
| 2013/0137595 A1 | 5/2013 | Zangar et al. |
| 2015/0111220 A1 | 4/2015 | Blume et al. |
| 2015/0168421 A1 | 6/2015 | Kearney et al. |
| 2017/0233816 A1 | 8/2017 | Mascarell et al. |
| 2020/0064355 A1 | 2/2020 | E et al. |

FOREIGN PATENT DOCUMENTS

| CN | 103025342 A | 4/2013 |
| EP | 2821076 A1 | 1/2015 |
| JP | 2016515199 A | 5/2016 |
| JP | 2017503503 A | 2/2017 |
| JP | 2021512316 A | 5/2021 |
| KR | 20160072041 A | 6/2016 |
| WO | WO-2011159878 A1 | 12/2011 |
| WO | WO-2012037603 A1 | 3/2012 |
| WO | WO-2012111249 A1 | 8/2012 |
| WO | WO-2013151726 A1 | 10/2013 |

(Continued)

OTHER PUBLICATIONS

Shen, Y., et al., "Blood peptidome-degradome profile of breast cancer", PloS One (2010); 5(10): e13133; 13 pages.

(Continued)

*Primary Examiner* — Xiaoyun R Xu
(74) *Attorney, Agent, or Firm* — COOLEY LLP

(57) ABSTRACT

The present disclosure provides methods and compositions for the determining the abundance and/or concentration of protein biomarkers in a biological sample.

8 Claims, 33 Drawing Sheets

Specification includes a Sequence Listing.

(56) References Cited

FOREIGN PATENT DOCUMENTS

| WO | WO-2015000988 A1 | 1/2015 |
|---|---|---|
| WO | WO-2015103645 A2 | 7/2015 |
| WO | WO-2016185385 A1 | 11/2016 |
| WO | WO-2017026241 A1 | 2/2017 |
| WO | WO-2017053983 A1 | 3/2017 |
| WO | WO-2018136825 A1 | 7/2018 |
| WO | WO-2019149816 A1 | 8/2019 |
| WO | WO-2020033537 A1 | 2/2020 |

OTHER PUBLICATIONS

Biognosys AG, "PlasmaDive™ Reference Peptides Kit for Human Plasma", First Edition, Version 1.00 [online] https://www.biognosys.com/media.ashx/plasmadiverefpep-manual.pdf (2017); 11 pages.

Cambridge Isotope Laboratories, Inc. and MRM Proteomics, "PeptiQuant™ Biomarker Assessment Kit (BAK-76)", [online] https://www.si-science.co.jp/product/data/2015product-2.pdf (Apr. 23, 2015); 3 pages.

Gallien, S., et al., "Selected reaction monitoring applied to proteomics", Journal of Mass Spectrometry (2011); 46(3): 298-312.

GenBank Accession No. ACN62221.1, complement C1q subcomponent subunit A [Danio rerio] (Sep. 3, 2010); 2 pages.

GenBank Accession No. ACN62222.1, complement C1q subcomponent subunit B [Danio rerio] (Sep. 3, 2010); 2 pages.

GenBank Accession No. ACN62223.1, complement C1q subcomponent subunit C [Danio rerio] (Sep. 3, 2010); 2 pages.

Mayr, M., et al., "Proteomics, metabolomics, and immunomics on microparticles derived from human atherosclerotic plaques", Circulation: Cardiovascular Genetics (2009); 2(4): 379-388; Supplemental Material, 55 pages.

Melis, J., et al., "Complement in therapy and disease: regulating the complement system with antibody-based therapeutics", Molecular Immunology (2015); 67(2): 117-130.

Molloy, B. J., "A Semi Quantitative Method for the Analysis of Tryptic Peptides in Human Serum: A Rapid, Targeted UPLC-MS/MS Approach Using Biognosys Plasma Dive Kit", Waters Corporation [online] https://www.waters.com/webassets/cros/library/docs/720006323en.pdf (Aug. 2018); 5 pages.

Molloy, B. J., "Single High-Throughput UPLC-MS-MS Platform For Targeted Metabolomic, Lipidomic and Proteomic Studies (Targeted Multi-Omics)", Water Corporation, Poster [online] https://www.waters.com/webassets/cms/library/dots/2018msacl_molloy_multi-omics.pdf 92018); 1 page.

NCBI Reference Sequence: NP_000482.3, complement C1q subcomponent subunit B precursor [Homo sapiens] (Jan. 2, 2020); 5 pages.

NCBI Reference Sequence: NP_001008515.1, complement C1q subcomponent subunit A precursor [Rattus norvegicus] (Dec. 27, 2019); 4 pages.

NCBI Reference Sequence: NP_001008524.1, complement C1q subcomponent subunit C precursor [Rattus norvegicus] (Dec. 24, 2019); 3 pages.

NCBI Reference Sequence: NP_001253737.1, complement C1q subcomponent subunit C precursor [Macaca mulatta] (Apr. 29, 2019); 2 pages.

NCBI Reference Sequence: NP_031598.2, complement C1q subcomponent subunit A precursor [Mus musculus] (Jan. 21, 2020); 4 pages.

NCBI Reference Sequence: NP_031600.2, complement C1q subcomponent subunit C precursor [Mus musculus] (Dec. 26, 2019); 4 pages.

NCBI Reference Sequence: NP_033907.1, complement C1q subcomponent subunit B precursor [Mus musculus] (Dec. 30, 2019); 4 pages.

NCBI Reference Sequence: NP_057075.1, complement C1q subcomponent subunit A precursor [Homo sapiens] (Nov. 26, 2019); 5 pages.

NCBI Reference Sequence: NP_062135.1, complement C1q subcomponent subunit B precursor [Rattus norvegicus] (Dec. 25, 2019); 4 pages.

NCBI Reference Sequence: NP_758957.2, complement C1q subcomponent subunit C isoform 1 precursor [Homo sapiens] (Dec. 31, 2019); 4 pages.

NCBI Reference Sequence: XP_003433793.1, complement C1q subcomponent subunit C [Canis lupus familiaris] (Sep. 5, 2017); 2 pages.

NCBI Reference Sequence: XP_005544557.1, Predicted: complement C1q subcomponent subunit B [Macaca fascicularis] (Jan. 25, 2016); 2 pages.

NCBI Reference Sequence: XP_014985904.1, complement C1q subcomponent subunit A [Macaca mulatta] (Apr. 26, 2019); 2 pages.

NCBI Reference Sequence: XP_014985910.1, complement C1q subcomponent subunit B [Macaca mulatta] (Apr. 26, 2019); 2 pages.

NCBI Reference Sequence: XP_015296579.1, Predicted: complement C1q subcomponent subunit C [Macaca fascicularis] (Jan. 25, 2016); 2 pages.

NCBI Reference Sequence: XP_015296582.1, Predicted: complement C1q subcomponent subunit A [Macaca fascicularis] (Jan. 25, 2016); 2 pages.

NCBI Reference Sequence: XP_535367.1, complement C1q subcomponent subunit A [Canis lupus familiaris] (Sep. 5, 2017); 2 pages.

NCBI Reference Sequence: XP_544507.2, complement C1q subcomponent subunit B [Canis lupus familiaris] (Sep. 5, 2017); 2 pages.

Rezeli, M., et al., "Quantitation of 87 proteins by nLC-MRM/MS in human plasma: workflow for large-scale analysis of biobank samples", Journal of Proteome Research (2017); 16(9): 3242-3254.

Zhou, G., et al., "Ultra Performance Liquid Chromatography-Tandem Mass Spectrometric Method for Detection of Pork Peptide Biomarkers", Chinese Journal of Analytical Chemistry (Feb. 2017); 45(2): 205-210.

UniProtKB/Swiss-Prot Accession No. P02745.2, "RecName: Full= Complement C1q subcomponent subunit A; Flags: Precursor", National Center for Biotechnology Information (NCBI) (Jul. 31, 2019) [online] https://www.ncbi.nlm.nih.gov/protein/399138?sat=47&satkey=98638392 (Access Date: Aug. 13, 2024); 8 pages.

UniProtKB/Swiss-Prot Accession No. P02746.3, "RecName: Full= Complement C1q subcomponent subunit B; Flags: Precursor", National Center for Biotechnology Information (NCBI) (Jul. 31, 2019) [online] https://www.ncbi.nlm.nih.gov/protein/298286922?sat=47&satkey=97893171 (Access Date: Aug. 13, 2024); 7 pages.

UniProtKB/Swiss-Prot Accession No. P02747.3, "RecName: Full= Complement C1q subcomponent subunit C; Flags: Precursor", National Center for Biotechnology Information (NCBI) (Jul. 31, 2019) [online] https://www.ncbi.nlm.nih.gov/protein/20178281?sat=47&satkey=97893211 (Access Date: Aug. 13, 2024); 7 pages.

USE OF LC-MS/MS TO QUANTITATE PROTEIN BIOMARKERS

RELATED APPLICATIONS

This application is a divisional of U.S. application Ser. No. 16/534,095, filed Aug. 7, 2019, now U.S. U.S. Pat. No. 11,592,449, which claims priority to, and the benefit of, U.S. Provisional Application No. 62/715,973, filed on Aug. 8, 2018, the contents of each of which are incorporated herein by reference in their entireties.

SEQUENCE LISTING

The Sequence Listing associated with this application is provided electronically in XML file format and is hereby incorporated by reference into the specification. The name of the XML file containing the Sequence Listing is "REGE-015_D01US_SeqList.xml". The XML file is 41,926 bytes and was created on Feb. 27, 2023.

BACKGROUND OF THE INVENTION

C1q is an important, druggable protein involved in the complement system of the innate immune system. There are currently immuno-based methods for determining the concentration of C1q in biological samples derived from humans. However, there exists limited immunoreagents for assaying the abundance of C1q in samples derived from non-human primates, an important model organism in preclinical research and trials. Thus, there is a need in the art for methods and compositions directed towards determining C1q concentration in samples derived from human, non-human primate and other model organisms that are rapid, specific and accurate, and that do not require the costly and time-consuming development of immunoreagents. The present disclosure addresses these needs.

SUMMARY OF THE INVENTION

The present disclosure provides an assay comprising: (1) contacting a biological sample with at least one proteolytic enzyme to produce at least one peptide fragment of the protein C1q present in the biological sample; and (2) performing selected reaction monitoring mass spectrometry (SRM-MS) to measure the abundance of the at least one C1q peptide fragment, wherein the abundance of the at least C1q peptide fragment determines the concentration of C1q in the biological sample.

The preceding assay can further comprise between step (1) and step (2), adding to the biological sample at least one labeled, synthetic C1q peptide fragment comprising an amino acid sequence identical to the amino acid sequence of the at least one C1q peptide fragment.

Measuring the abundance of the at least one C1q peptide fragment in the preceding assay can comprise comparing a signal corresponding to the at least one C1q peptide generated by SRM-MS to a standard curve.

The present disclosure provides an assay comprising: (1) contacting a biological sample with at least one proteolytic enzyme to produce at least one peptide fragment of the protein C1q present in the biological sample; (2) performing selected reaction monitoring mass spectrometry (SRM-MS) to generate a signal corresponding to the at least one C1q peptide fragment; and (3) determining the abundance of the at least one C1q peptide fragment by comparing the signal to a standard curve, wherein the abundance of the at least C1q peptide fragment determines the concentration of C1q in the biological sample.

The preceding assay can further comprise between step (1) and step (2), adding to the biological sample at least one labeled, synthetic peptide fragment comprising an amino acid sequence identical to the amino acid sequence of the at least one C1q peptide fragment, and between step (2) and step (3), performing SRM-MS to generate a signal corresponding to the at least one labeled, synthetic peptide.

The biological sample can be a blood sample. The biological sample can be a human sample. The biological sample can be a non-human primate sample.

The at least one peptide fragment can comprise at least 5 amino acids. The at least one peptide fragment can comprise a peptide selected from Table 2.

The at least one peptide fragment can comprise SLGFCDTTNK (SEQ ID NO: 26), IAFSATR (SEQ ID NO: 29) or QTHQPPAPNSLIR (SEQ ID NO: 36). The at least one peptide fragment can comprise at least two of SLGFCDTTNK (SEQ ID NO: 26), IAFSATR (SEQ ID NO: 29) or QTHQPPAPNSLIR (SEQ ID NO: 36). The at least one peptide fragment can comprise each of SLGFCDTTNK (SEQ ID NO: 26), IAFSATR (SEQ ID NO: 29) and QTHQPPAPNSLIR (SEQ ID NO: 36).

The selected reaction monitoring mass spectrometry can be LC-SRM-MS/MS.

The at least one proteolytic enzyme can be trypsin.

A standard curve can be produced using a method comprising: (a) preparing at least two C1q concentration standards by mixing known quantities of purified C1q protein and C1q-depleted serum; (b) adding to the at least two C1q concentration standards at least one labeled, synthetic peptide fragment with an amino acid sequence identical to an at least one peptide fragment of C1q that is expected to be produced following contacting the C1q concentration standard with a proteolytic enzyme; (c) contacting the at least two labeled C1q concentration standards with a proteolytic enzyme to produce at least one peptide fragment of C1q; (d) performing selected reaction monitoring mass spectrometry to determine the strength of the signal that corresponds to the at least one peptide fragment of C1q and the strength of the signal that corresponds to the at least one labeled, synthetic peptide fragment in each of the at least two labeled C1q concentration standards; and (e) determining a standard curve using the signals and the known quantities of C1q protein.

The present disclosure provides a composition comprising at least one isolated synthetic peptide, said composition comprising at least one isolated synthetic peptide with an amino acid sequence selected from the protein C1q.

A composition comprising at least one isolated synthetic peptide, said composition comprising at least one isolated synthetic peptide with an amino acid sequence selected from the protein C1q, wherein the amino acid sequence selected from the protein C1q is the sequence of a C1q peptide fragment generated by contacting C1q with at least one proteolytic enzyme.

The C1q protein can be from a human. The C1q protein can be from a non-human primate.

The at least one isolated synthetic peptide can comprise at least 5 amino acids.

The amino acid sequence selected from the protein C1q can be the sequence of a C1q peptide fragment generated by contacting C1q with at least one proteolytic enzyme. The at least one proteolytic enzyme can be trypsin.

The at least one isolated synthetic peptide can be labeled.

The at least one isolated synthetic peptide can comprise a peptide selected from Table 2.

The at least one isolated synthetic peptide can comprise SLGFCDTTNK (SEQ ID NO: 26), IAFSATR (SEQ ID NO: 29) or QTHQPPAPNSLIR (SEQ ID NO: 36). The cysteine in the synthetic peptide SLGFCDTTNK (SEQ ID NO: 26) can be modified. The modification can be carbamidomethylation.

The present disclosure provides a composition comprising at least one transition ion pair, said composition comprising at least one transition ion pair of the protein C1q, wherein the at least one transition ion pair consists of a precursor ion with a corresponding m/z and a fragment ion with a corresponding ion m/z.

The C1q protein can be from a human. The C1q protein can be from a non-human primate.

The present disclosure provides a composition comprising at least one transition ion pair, said composition comprising at least one transition ion pair of the protein C1q, wherein the at least one transition ion pair consists of a precursor ion with a corresponding m/z and a fragment ion with a corresponding ion m/z, and wherein the transition ion pair is selected from precursor SLGFC(Cam)DTTNK (SEQ ID NO: 41) transition pair 571.8-942.3, precursor IAFSATR (SEQ ID NO: 29) transition pair 383.1-581.1 and precursor QTHQPPAPNSLIR (SEQ ID NO: 36) transition pair 487.0-350.3. Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

DETAILED DESCRIPTION OF THE INVENTION

Figure 1:
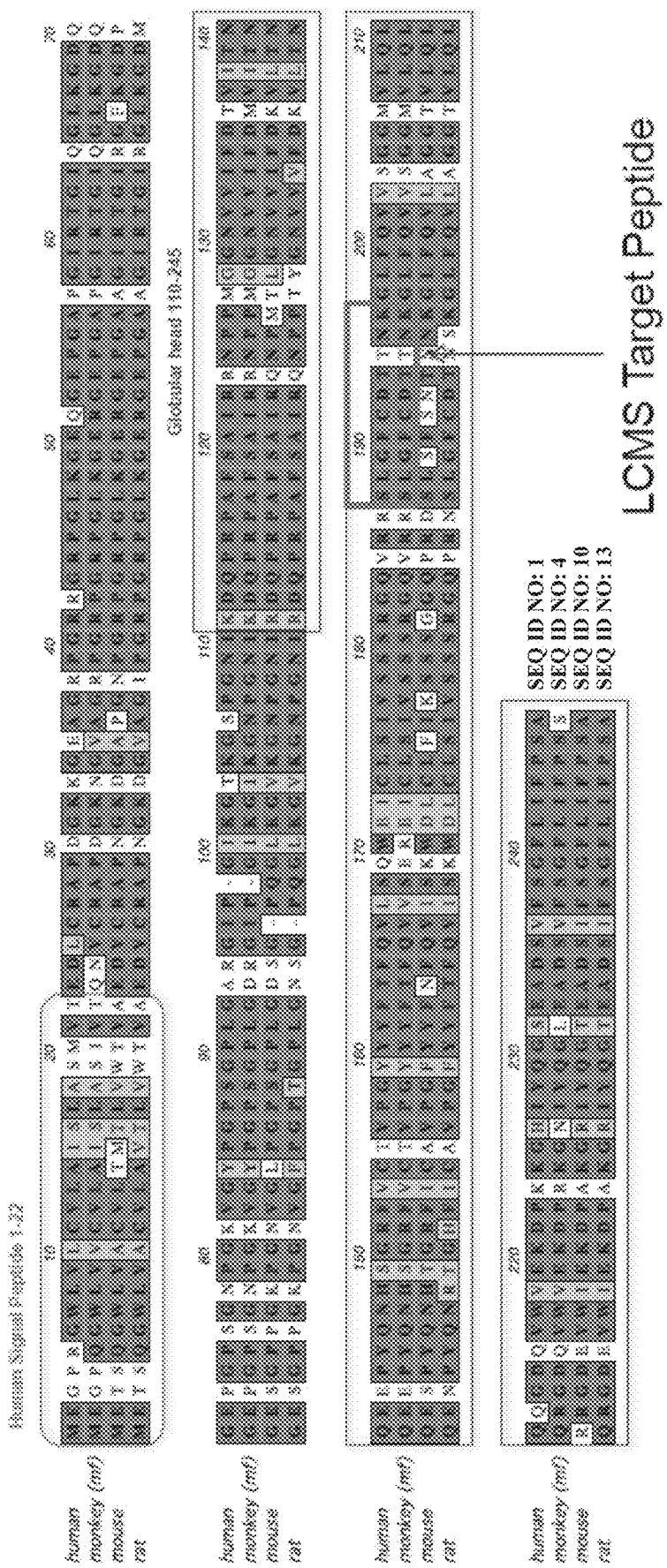
FIG. 1 is the amino acid sequence alignment of the A subunit of C1q from human, monkey, mouse and rat.

The present disclosure provides methods and compositions for determining the abundance and/or concentration of protein biomarkers in a biological sample. In some aspects, this protein biomarker is the protein C1q. In some aspects, the methods of the present disclosure comprise liquid chromatography selected reaction monitoring mass spectrometry (LC-SRM-MS) analysis.

The complement component 1q (C1q) is a protein complex involved in the complement system, which is part of the innate immune system. C1q together with C1r and C1s form the C1 complex. C1q is a 400 kDa protein consisting of 18 polypeptide subunits: six A-subunits, six B-subunits, and six C-subunits. Complement inhibitors have been successfully used in treating several diseases. C1q-targeted monoclonal antibodies have potential as therapy for autoimmune diseases involving the classical complement pathway. The development of C1q-targeting treatment approaches requires methods for determining the concentration of C1q levels in biological samples during laboratory research and clinical trials. To date, determining the C1q abundance in human samples requires the use of immunoassays, such as ELISA. Furthermore, there exists limited immunoreagents for assaying C1q in non-human primate samples, which are an important aspect of pre-clinical research and trials. Thus, there exists a need for an improved assay for determining C1q concentration in biological samples derived from humans, non-human primates and other model organisms.

Liquid chromatography selected reaction monitoring mass spectrometry (LC-SRM-MS) methods are highly desirable because LC-SRM-MS methods provide both absolute structural specificity for the target protein and relative or absolute measurement of the target protein concentration when suitable internal standards are utilized.

Methods of the Present Disclosure

Various methods of the present disclosure are described in full detail herein.

The present disclosure provides a method comprising an assay comprising: (1) contacting a biological sample with at least one proteolytic enzyme to produce at least one peptide fragment of the protein C1q present in the biological sample; and (2) performing selected reaction monitoring mass spectrometry (SRM-MS) to measure the abundance of the at least one C1q peptide fragment, wherein the abundance of the at least one C1q peptide fragment determines the concentration of C1q in the biological sample.

In some aspects, the preceding method can further comprise between step (1) and step (2), adding to the biological sample at least one labeled synthetic C1q peptide fragment comprising an amino acid sequence identical to the amino acid sequence of the at least one C1q peptide fragment.

The present disclosure also provides a method comprising an assay comprising: (1) contacting a biological sample with at least one proteolytic enzyme to produce at least one peptide fragment of the protein C1q present in the biological sample; (2) performing selected reaction monitoring mass spectrometry (SRM-MS) to generate a signal corresponding to the at least one C1q peptide fragment; and (3) determining the abundance of the at least one C1q peptide fragment by comparing the signal to a standard curve, wherein the abundance of the at least one C1q peptide fragment determines the concentration of C1q in the biological sample.

In some aspects, the preceding method can further comprise between step (1) and step (2), adding to the biological sample at least one labeled, synthetic peptide fragment comprising an amino acid sequence identical to the amino acid sequence of the at least one C1q peptide fragment, and between step (2) and step (3), performing SRM-MS to generate a signal corresponding to the at least one labeled, synthetic peptide.

In some aspects, the biological sample can be a blood sample. In preferred aspects, the biological sample can be a serum sample. In some aspects, the biological sample can be a human sample. Alternatively, the biological sample can be a non-human primate sample. The non-human primate can be *Macaca fascicularis* or *Macaca mulatta*.

In some aspects, the C1q protein can be human C1q protein. In other aspects, the C1q protein is *Macaca fascicularis* C1q protein. In yet another aspect, the C1q protein can be *Macaca mulatta* C1q protein. The C1q protein can comprise any of the sequences show in Table 1.

TABLE 1

Sequences of C1q proteins

| Species | Subunit | NCBI ref # | Sequence | SEQ ID NO |
|---------|---------|------------|----------|-----------|
| Human (*Homo sapiens*) | A | NP_057075 | MEGPRGWLVLCVLAISLASMVTEDLCRAPD GKKGEAGRPGRRGRPGLKGEQGEPGAPGIR TGIQGLKGDQGEPGPSGNPGKVGYPGPSGP LGARGIPGIKGTKGSPGNIKDQPRPAFSAI RRNPPMGGNVVIFDTVITNQEEPYQNHSGR FVCTVPGYYYFTFQVLSQWEICLSIVSSSR GQVRRSLGFCDTTNKGLFQVVSGGMVLQLQ QGDQVWVEKDPKKGHIYQGSEADSVFSGFL IFPSA | 1 |
| | B | NP_000482 | MMMKIPWGSIPVLMLLLLLGLIDISQAQLS CTGPPAIPGIPGIPGTPGPDGQPGTPGIKG EKGLPGLAGDHGEFGEKGDPGIPGNPGKVG PKGPMGPKGGPGAPGAPGPKGESGDYKATQ KIAFSATRTINVPLRRDQTIRFDHVITNMN NNYEPRSGKFTCKVPGLYYFTYHASSRGNL CVNLMRGRERAQKVVTFCDYAYNTFQVTTG GMVLKLEQGENVFLQATDKNSLLGMEGANS IFSGFLLFPDMEA | 2 |
| | C | NP_758957 | MDVGPSSLPHLGLKLLLLLLLLPLRGQANT GCYGIPGMPGLPGAPGKDGYDGLPGPKGEP GIPAIPGIRGPKGQKGEPGLPGHPGKNGPM | 3 |

TABLE 1-continued

Sequences of C1q proteins

| Species | Subunit | NCBI ref # | Sequence | SEQ ID NO |
|---|---|---|---|---|
| | | | GPPGMPGVPGPMGIPGEPGEEGRYKQKFQS VFTVTRQTHQPPAPNSLIRFNAVLTNPQGD YDTSTGKFTCKVPGLYYFVYHASHTANLCV LLYRSGVKVVTFCGHTSKTNQVNSGGVLLR LQVGEEVWLAVNDYYDMVGIQGSDSVFSGF LLFPD | |
| Cynomolgus monkey (*Macaca fascicularis*) | A | XP_015296582 | MEGPQGWLVVCVLAISLASIVTQNVCRAPD GKNGVAGRPGRPGRPGLKGERGEPGAPGIR TGIQGLKGDQGEPGPSGNPGKVGYPGPSGP LGDRGIPGIKGIKGNPGNIKDQPRPAFSAI RRNPPMGGNVVIFDMVITNQEEPYQNHSGR FVCTVPGYYYFTFQVVSEREICLSIVSSSR GQVRRSLGFCDTTNKGLFQVVSGGMVLQLQ RGDQVWVEKDPRKGNIYQGLEADSVFSGFL IFPSS | 4 |
| | B | XP_005544557 | MMMKILWGSIPVLMLLLLLGLLDVSWAQGS CTGPPAIPGTPGIPGTPGSDGQPGTPGIKG EKGLPGLAGDHGEFGEKGDPGIPGNPGKVG PKGPMGPKGGPGAPGAPGPKGESGDYKATQ KIAFSATRTVNTPLRRDQTIRFDHVITNMN NNYEPRSGKFTCRVPGLYYFTYHASSRGNL CVKLMRGRERPQKVVTFCDYAYNTFQVTTG GMVLKLEQGENVFLQATDKNSLLGMEGANS IFSGFLLFPDVEA | 5 |
| | C | XP_015296579 | MDVGPSSLPHLGLKLLLLLLLLPLRGQANT GCYGIPGMPGLPGAPGKDGHDGLPGPKGEP GIPAIPGTRGPKGQKGEPGTPGHPGKNGPM GPPGMPGVPGPMGIPGEPGEEGRYKQKYQS VFTVARQTHQPPAPNSLIRFNAVLTNPQGD YDTSTGKFTCKVPGLYYFVYHASHTANLCV LLYRGGVKVVTFCGHTSQANQVNSGGVLLR LQVGEEVWLGVNDYYDMVGIQGSDSVFSGF LLFPD | 6 |
| Rhesus monkey (*Macaca mulatta*) | A | XP_014985904 | MEGPQGWLVVCVLAISLASIVTQNVCRAPD GKNGVAGRPGRPGRPGLKGERGEPGAPGIR TGIQGLKGDQGEPGPSGNPGKVGYPGPSGP LGDRGIPGIKGIKGNPGNIKDQPRPAFSAI RRNPPMGGNVVIFDMVITNQEEPYQNHSGR FVCTVPGYYYFTFQVVSEREICLSIVSSSR GQVRRSLGFCDTTNKGLFQVVSGGMVLQLQ RGDQVWVEKDPRKGNIYQGLEADSVFSGFL IFPST | 7 |
| | B | XP_014985910 | MMMKILWGSIPVLMLLLLLGLLDVSWAQGS CTGPPAIPGTPGIPGTPGSDGQPGTPGIKG EKGLPGLAGDHGEFGEKGDPGIPGNPGKVG PKGPMGPKGGPGAPGAPGPKGESGDYKATQ KIAFSATRTINTPLRRDQTIRFDHVITNMN NNYEPRSGKFTCRVPGLYYFTYHASSRGNL CVKLMRGRERPQKVVTFCDYAYNTFQVTTG GMVLKLEQGENVFLQATDKNSLLGMEGANS IFSGFLLFPDVEA | 8 |
| | C | NP_001253737 | MDVGPSSLPHLGLKLLLLLLLLPLRGQANT GCYGIPGMPGLPGAPGKDGHDGLPGPKGEP GIPAIPGTRGPKGQKGEPGTPGHPGKNGPM GPPGMPGVPGPMGIPGEPGEEGRYKQKYQS VFTVARQTHQPPAPNSLIRFNAVLTNPQGD YDTSTGKFTCKVPGLYYFVYHASHTANLCV LLYRGGVKVVTFCGHTSQANQVNSGGVLLR LQVGEEVWLGVNDYYDMVGIQGSDSVFSGF LLFPD | 9 |
| Mouse (*Mus musculus*) | A | NP_031598 | METSQGWLVACVLTMTLVWTVAEDVCRAPN GKDGAPGNPGRPGRPGLKGERGEPGAAGIR TGIRGFKGDPGESGPPGKPGNVGLPGPSGP LGDSGPQGLKGVKGNPGNIRDQPRPAFSAI RQNPMTLGNVVIFDKVLTNQESPYQNHTGR FICAVPGFYYFNFQVISKWDLCLFIKSSSG GQPRDSLSFSNTNNKGLFQVLAGGTVLQLR | 10 |

TABLE 1-continued

Sequences of C1q proteins

| Species | Subunit | NCBI ref # | Sequence | SEQ ID NO |
|---|---|---|---|---|
| | | | RGDEVWIEKDPAKGRIYQGTEADSIFSGFL IFPSA | |
| | B | NP_033907 | MKTQWGEVWTHLLLLLLGFLHVSWAQSSCT GPPGIPGIPGVPGVPGSDGQPGTPGIKGEK GLPGLAGDLGEFGEKGDPGIPGTPGKVGPK GPVGPKGTPGPSGPRGPKGDSGDYGATQKV AFSALRTINSPLRPNQVIRFEKVITNANEN YEPRNGKFTCKVPGLYYFTYHASSRGNLCV NLVRGRDRDSMQKVVTFCDYAQNTFQVTTG GVVLKLEQEEVVHLQATDKNSLLGIEGANS IFTGFLLFPDMDA | 11 |
| | C | NP_031600 | MVVGPSCQPPCGLCLLLLFLLALPLRSQAS AGCYGIPGMPGMPGAPGKDGHDGLQGPKGE PGIPAVPGTRGPKGQKGEPGMPGHRGKNGP RGTSGLPGDPGPRGPPGEPGVEGRYKQKHQ SVFTVTRQTTQYPEANALVRFNSVVTNPQG HYNPSTGKFTCEVPGLYYFVYYTSHTANLC VHLNLNLARVASFCDHMFNSKQVSSGGVLL RLQRGDEVWLSVNDYNGMVGIEGSNSVFSG FLLFPD | 12 |
| Rat (Rattus norvegicus) | A | NP_001008515 | METSQGWLVACVLAVTLVVVTVAEDVCRAP NGKDGVAGIPGRPGRPGLKGERGEPGAAGI RTGIRGLKGDMGESGPPGKPGNVGFPGPTG PLGNSGPQGLKGVKGNPGNIRDQPRPAFSA IRQNPPTYGNVVVFDKVLTNQENPYQNRTG HFICAVPGFYYFTFQVISKWDLCLSIVSSS RGQPRNSLGFCDTNSKGLFQVLAGGTVLQL QRGDEVWIEKDPAKGRIYQGTEADSIFSGF LIFPSA | 13 |
| | B | NP_062135 | MKTQWSEILTPLLLLLLGLLHVSWAQSSCT GSPGIPGVPGIPGVPGSDGKPGTPGIKGEK GLPGLAGDHGELGEKGDAGIPGIPGKVGPK GPVGPKGAPGPPGPRGPKGGSGDYKATQKV AFSALRTVNSALRPNQAIRFEKVITNVNDN YEPRSGKFTCKVPGLYYFTYHASSRGNLCV NIVRGRDRDRMQKVLTFCDYAQNTFQVTTG GVVLKLEQEEVVHLQATDKNSLLGVEGANS IFTGFLLFPDMDV | 14 |
| | C | NP_001008524 | MVVGTSCQPQHGLYLLLLLLALPLRSQANA GCYGIPGMPGLPGTPGKDGHDGLQGPKGEP GIPAIPGTQGPKGQKGEPGMPGHRGKNGPM GTSGSPGDPGPRGPPGEPGEEGRYKQKHQS VFTVTRQTAQYPAANGLVKFNSAITNPQGD YNTNTGKFTCKVPGLYYFVHHTSQTANLCV QLLLNNAKVTSFCDHMSNSKQVSSGGVLLR LQRGDEVWLAVNDYNGMVGTEGSDSVFSGF LLFPD | 15 |
| Dog (Canis lupus familiaris) | A | XP_535367 | MEAPWGWLALCVLATSLASAVTQDVCRALD GRDGAAGTPGRPGRPGLKGEQGEPGAPGMR TGIRGLKGDQGDPGPPGNPGNMGFPGPSGL MGLPGIPGRRGPKGNPGNIRDQPRPAFSAI RRNPPTGGNVVIFDTVITNQEGPYQNHSGR FICAVPGYYYFTFQVVSKWDICLSIVSSGR AQIRRSLGFCDTNSKGIFQVVSGGMALQLQ QGDQVWIEKDPIKGRIYQGPEADSIFSGFL IFPSL | 16 |
| | B | XP_544507 | MKTPRGGILALLLPLLLGLLEVSWAQSCTG HPAIPGIPGIPGAPGTDGTPGTPGTKGEKG LPGLAGDHGEFGEKGDPGIPGTPGKVGPKG PVGPKGSPGPPGARGAKGESGDYKATQKIA FSAMRTINIPLRRDQTIRFDHIVTNENRNY EPRSGKFTCNVPGIYYFAYHASSRGNLCVN VMRGRERMQKVVTFCDYVQNTFQVTTGSVV LKLSQGENVYLQATDKNSLLGMEGANSIFS GFLLFPDAEA | 17 |

TABLE 1-continued

Sequences of C1q proteins

| Species | Subunit | NCBI ref # | Sequence | SEQ ID NO |
|---|---|---|---|---|
| | C | XP_003433793 | MDTGPSSWPHLGLNLLLLLLALPLGGQAST GCYGIPGMPGLPGAPGKDGHDGLPGPKGEP GIPAIPGTRGPKGQKGEPGTPGYPGKNGPM GTPGIPGVPGPVGPPGEPGEEGRYKQKHQS VFTVTRQTAQYPLANNLVKFNTVITNPQGD YDTSTGKFTCKVPGLYYFVYHTSLTSNLCV HLYRSGTRVTTFCDHMSNSKQVSSGGVLLR LQMGEQVWLAVNDYNGMVGTEGSDSVFSGF LLFPD | 18 |
| Zebrafish (Danio rerio) | A | ACN62221 | MQPSAFFAFLWAGALFPFSFCQDECVKHGR NGADGPNGRDGLPGPKGEKGEPALQVKLSS IALEELKGDMGVRGPPGEPGLEGLMGAIGP RGPLGPAGPRGSSVGADGAKASEKPAFSVL RNEASQAQYKQPVTFNDKLSDANDDFQIKT GYFTCKVPGVYYFVFHASSEGRLCLRLKST SAPPVSLSFCDFNSKSVSLVVSGGAVLTLL KGDKVWIEPFAGDGGVGQMPKRLYAVFNGF LIYRNAE | 19 |
| | B | ACN62222 | MLFALMSAHVVPQLAIMLLLVTSSMSETCA GNKGFPGTPGIPGVPGTDGKDGAKGEKGDP GENEVQMTGPKGDPGKPGLPGRPGVKGPEG PQGPPGPPGPKGQRGVLSGKVAPDQYFVFS YKKSQKLEKILQDKLVVFDVPLITGIDGVL DGEGYFDVTITGMYYISYQISFQQSACLKI QIGAEEKVKFCDSPKLILGTAASVVLKLNK GDKVSVQSTGESTVFSRDTDCTFTGFMLFP IK | 20 |
| | C | ACN62223 | MFGGHLILVSLLSASLCLCLASADTCPAGA MPGLPGIPGFPGRDGRQGMKGEKGDLGIPI KPGDTVKKGERGAFGLKGPPGKRGPHGDPG IMGPPGPPGEPGEAGLVDVSGSQLQSAFSV SRHTRIPPDANKVIRFSKVITNPQGHFSTD ESKFVCKIPGTYYFVLHASSHDKKLCVILV HDDKNLVSFCDHTQRGSQQVSSGGLSLYLK ENEKVWLMTNALNGMYATADRADSVFSGFL IHAH | 21 |

In some aspects of the preceding methods, the at least one peptide fragment of the protein C1q comprises at least 3, at least 4, at least 5, at least 6, at least 7, at least 8, at least 9, at least 10 or at least 20 amino acids.

In some aspects of the preceding methods, the at least one peptide fragment of the protein C1q comprises a peptide selected from Table 2. In other aspects, the at least one peptide fragment comprises a tryptic peptide of the protein C1q.

TABLE 2

C1q peptide sequences

| Peptide Sequence | Subunit of C1q | SEQ ID NO |
|---|---|---|
| VGYPGPSGPLGAR | A | 22 |
| DQPRPAFSAIR* | A | 23 |
| NPPMGGNVVIFDTVITNQEEPYQNHSGR | A | 24 |
| FVCTVPGYYYFTFQVLSQWEICLSIVSSSR | A | 25 |
| SLGFCDTTNK* | A | 26 |
| GLFVVSGGMVLQLQQGDQVWVEKDPK | A | 27 |

TABLE 2-continued

C1q peptide sequences

| Peptide Sequence | Subunit of C1q | SEQ ID NO |
|---|---|---|
| GHIYQGSEADSVFSGFLIFPSA | A | 28 |
| IAFSATR* | B | 29 |
| TINVPLRR | B | 30 |
| FDHVITNMNNNYEPR* | B | 31 |
| VPGLYYFTYHASSR* | B | 32 |
| GNLCVNLMR | B | 33 |
| LEQGENVFLQATDK* | B | 34 |
| FQSVFTVTR | C | 35 |
| QTHQPPAPNSLIR* | C | 36 |
| FNAVLTNPQGDYDTSTGK* | C | 37 |
| VPGLYYFVYHASHTANLCVLLYR* | C | 38 |

TABLE 2-continued

C1q peptide sequences

| Peptide Sequence | Subunit of C1q | SEQ ID NO |
|---|---|---|
| VVTFCGHTSK | C | 39 |
| TNQVNSGGVLLR | C | 40 |

*denotes human/monkey C1q common peptide.

In some aspects of the preceding methods, the at least one peptide fragment of the protein C1q comprises SLGFCDTTNK (SEQ ID NO: 26), IAFSATR (SEQ ID NO: 29) or QTHQPPAPNSLIR (SEQ ID NO: 36). In other aspects, the at least one peptide fragment comprises at least two of SLGFCDTTNK (SEQ ID NO: 26), IAFSATR (SEQ ID NO: 29) or QTHQPPAPNSLIR (SEQ ID NO: 36). In still other aspects, the at least one peptide fragment comprises each of SLGFCDTTNK (SEQ ID NO: 26), IAFSATR (SEQ ID NO: 29) and QTHQPPAPNSLIR (SEQ ID NO: 36).

Thus, the present disclosure encompasses a method comprising an assay comprising: (1) contacting a biological sample with at least one proteolytic enzyme to produce at least one peptide fragment of the protein C1q present in the biological sample, wherein the at least one peptide fragment comprises each of SLGFCDTTNK (SEQ ID NO: 26), IAFSATR (SEQ ID NO: 29) and QTHQPPAPNSLIR (SEQ ID NO: 36); (2) performing SRM-MS to generate a signal corresponding to the at least one C1q peptide fragment, wherein the SRM-MS signals are according to transition ion pairs comprising each of precursor SLGFCDTTNK (SEQ ID NO: 26) transition pair 571.8-942.3, precursor IAFSATR (SEQ ID NO: 29) transition pair 383.1-581.1, and precursor QTHQPPAPNSLIR (SEQ ID NO: 36) transition pair 487.0-350.3; and (3) determining the abundance of the at least one C1q peptide fragment by comparing the signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprises each of SLGFCDTTNK (SEQ ID NO: 26), IAFSATR (SEQ ID NO: 29) and QTHQPPAPNSLIR (SEQ ID NO: 36); (2) adding to the biological sample at least one labeled, synthetic peptide fragment comprising an amino acid sequence identical to the amino acid sequence of each of SLGFCDTTNK (SEQ ID NO: 26), IAFSATR (SEQ ID NO: 29) and QTHQPPAPNSLIR (SEQ ID NO: 36); (3) performing SRM-MS to generate a signal corresponding to the at least one C1q peptide fragment, wherein the SRM-MS signals are according to transition ion pairs comprising each of precursor SLGFCDTTNK (SEQ ID NO: 26) transition pair 571.8-942.3, precursor IAFSATR (SEQ ID NO: 29) transition pair 383.1-581.1, and precursor QTHQPPAPNSLIR (SEQ ID NO: 36) transition pair 487.0-350.3, and a signal corresponding to the at least one labeled, synthetic peptide; and (4) determining the abundance of the at least one C1q peptide fragment by comparing the signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprises SLGFCDTTNK (SEQ ID NO: 26); (2) performing selected reaction monitoring mass spectrometry (SRM-MS) to generate a signal corresponding to the at least one C1q peptide fragment, wherein the SRM-MS signals are according to transition ion pairs comprising precursor SLGFC (Cam) DTTNK (SEQ ID NO: 41) transition pair 571.8-942.3; and (3) determining the abundance of the at least one C1q peptide fragment by comparing the normalized signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprises SLGFCDTTNK (SEQ ID NO: 26); (2) adding to the biological sample at least one labeled, synthetic peptide fragment comprising an amino acid sequence identical to the amino acid sequence of SLGFCDTTNK (SEQ ID NO: 26); (3) performing selected reaction monitoring mass spectrometry (SRM-MS) to generate a signal corresponding to the at least one C1q peptide fragment, wherein the SRM-MS signals are according to transition ion pairs comprising precursor SLGFC (Cam) DTTNK (SEQ ID NO: 41) transition pair 571.8-942.3, and a signal corresponding to the at least one labeled, synthetic peptide; and (4) determining the abundance of the at least one C1q peptide fragment by comparing the normalized signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprising IAFSATR (SEQ ID NO: 29); (2) performing selected reaction monitoring mass spectrometry (SRM-MS) to generate a signal corresponding to the at least one C1q peptide fragment, wherein the SRM-MS signals are according to transition ion pairs comprising precursor IAFSATR (SEQ ID NO: 29) transition pair 383.1-581.1; and (3) determining the abundance of the at least one C1q peptide fragment by comparing the signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprising IAFSATR (SEQ ID NO: 29); (2) adding to the biological sample at least one labeled, synthetic peptide fragment comprising an amino acid sequence identical to the amino acid sequence of IAFSATR (SEQ ID NO: 29); (3) performing selected reaction monitoring mass spectrometry (SRM-MS) to generate a signal corresponding to the at least one C1q peptide fragment, wherein the SRM-MS signals are according to transition ion pairs comprising precursor IAFSATR (SEQ ID NO: 29) transition pair 383.1-581.1, and a signal corresponding to the at least one labeled, synthetic peptide; and (4) determining the abundance of the at least one C1q peptide fragment by comparing the signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprises QTHQPPAPNSLIR (SEQ ID NO: 36); (2) performing selected reaction monitoring mass spectrometry (SRM-MS) to generate a signal corresponding to the at least one C1q peptide fragment, wherein the SRM-MS signals are according to transition ion pairs comprising precursor QTHQPPAPNSLIR (SEQ ID NO: 36) transition pair 487.0-350.3; and (3) determining the abundance of the at least one C1q peptide fragment by comparing the signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprises QTHQPPAPNSLIR (SEQ ID NO: 36); (2) adding to the biological sample at least one labeled, synthetic peptide fragment comprising an amino acid sequence identical to the amino acid sequence of QTHQPPAPNSLIR (SEQ ID NO: 36); (3) performing selected reaction monitoring mass spectrometry (SRM-MS) to generate a signal corresponding to the at least one C1q peptide fragment, wherein the SRM-MS signals are according to transition ion pairs comprising precursor QTHQPPAPNSLIR (SEQ ID NO: 36) transition pair 487.0-350.3, and a signal corresponding to the at least one labeled, synthetic peptide; and (4) determining the abundance of the at least one C1q peptide fragment by comparing the signal to a standard curve, wherein the abundance of the at least C1q peptide fragment determines the concentration of C1q in the biological sample.

In some aspects of the methods of the present disclosure, the selected reaction monitoring mass spectrometry is LC-SRM-MS/MS.

In some aspects of the methods of the present disclosure, the at least one proteolytic enzyme is trypsin. Other suitable proteolytic enzymes will be known to those of skill in the art, including, but not limited to Glu-C protease, Lys-N protease, Lys-C protease, Asp-N protease or chymotrypsin.

In some aspects of the methods of the present disclosure, a standard curve can be produced using a method comprising: (a) preparing at least two C1q concentration standards by mixing known quantities of purified C1q protein and C1q-depleted serum; (b) adding to the at least two C1q concentration standards at least one labeled, synthetic peptide fragment with an amino acid sequence identical to an at least one peptide fragment of C1q that is expected to be produced following contacting the C1q concentration standard with a proteolytic enzyme; (c) contacting the at least two labeled C1q concentration standards with a proteolytic enzyme to produce at least one peptide fragment of C1q; (d) performing selected reaction monitoring mass spectrometry to determine the strength of the signal that corresponds to the at least one peptide fragment of C1q and the strength of the signal that corresponds to the at least one labeled, synthetic peptide fragment in each of the at least two labeled C1q concentration standards; and (e) determining a standard curve using the signals and the known quantities of C1q protein.

In some aspects, a standard curve can be produced using at least three, or at least four, or at least five, or at least six, or at least seven, or at least eight, or at least nine or at least ten C1q concentration standards. In some aspects, preparing a C1q concentration standard can comprise diluting, or serially diluting, purified C1q protein in C1q-depleted serum, wherein the dilution factor can be 1:1, 1:1.5, or 1:2, or 1:2.5, or 1:3, or 1:3.5, or 1:4, or 1:5, or 1:6, or 1:7, or 1:8, or 1:9, or 1:10, or 1:100, or 1:1000, or any dilution factor within the range of 1:1 to 1:10000.

In some aspects of the methods of the present disclosure, at least one labeled, synthetic peptide fragment can be added to a biological sample prior to contacting the biological sample with a proteolytic enzyme.

In some aspects of the present disclosure, the at least one labeled, synthetic peptide fragment can be used for troubleshooting the methods of the present disclosure.

In some aspects of the present disclosure, the signal that correspond to the at least one labeled, synthetic peptide fragment can be used to normalize the signal of the at least one peptide fragment of the protein C1q to which the labeled, synthetic peptide fragment corresponds.

In some aspects of the methods of the present disclosure, a C1q standard curve can be used to measure the C1q abundance in biological samples. The abundance of the C1q peptides in predetermined, standard samples can be defined and the results compared to the LC-SRM-MS results from a corresponding C1q peptide found in a biological sample. This allows for the calculation of the abundance of the peptide in the biological sample. Thus, by knowing the abundance of a peptide in a sample, the abundance of the protein it corresponds to is determined.

Compositions of the Present Disclosure

Various compositions of the present disclosure are described in full detail herein.

The present disclosure provides a composition comprising at least one isolated synthetic peptide, said composition comprising at least one isolated synthetic peptide with an amino acid sequence selected from the protein C1q.

Synthetic peptides can be generated using any method known in the art. These methods can include recombinant expression techniques such as expression in bacteria or in vitro expression in eukaryotic cell lysate. These methods can also include solid phase synthesis.

The synthetic peptides can be isotopically labeled. The isotopes with which they can be labeled include $^{13}C$, $^{2}H$, $^{15}N$ and $^{18}O$. A labeled peptide can comprise at least one $^{13}C$ labeled and/or $^{15}N$ labeled Lysine residue, or at least one $^{13}C$ labeled and/or $^{15}N$ labeled Arginine residue. The peptides can also include a polar solvent. Polar solvents can include water and mixtures of ethanol and water.

In some aspects of compositions of the present disclosure, the C1q protein can be human C1q protein. In other aspects, the C1q protein is *Macaca fascicularis* C1q protein. In yet another aspect, the C1q protein can be *Macaca mulatta*. The C1q protein can comprise any of the sequences show in Table 1.

In some aspects of a composition of the present disclosure, the at least one isolated synthetic peptide comprises at least 3, at least 4, at least 5, at least 6, at least 7, at least 8, at least 9, at least 10 or at least 20 amino acids.

In some aspects of a composition of the present disclosure, an isolated synthetic peptide comprises a sequence of a C1q peptide fragment generated by contacting C1q with a proteolytic enzyme. In preferred aspects, the proteolytic enzyme is trypsin. Thus, in preferred aspects, an isolated synthetic peptide is a tryptic peptide of C1q.

In some aspects of a composition of the present disclosure, an isolated synthetic peptide is labeled. The isolated synthetic peptides can be isotopically labeled. The isotopes with which they can be labeled include, but are not limited to, $^{13}C$, $^{2}H$, $^{15}N$ and $^{18}O$. The peptides can also include a polar solvent. Polar solvents can include water, mixtures of ethanol and water and acetonitrile.

In some aspects of a composition of the present disclosure, the isolated synthetic peptide comprises a peptide selected from Table 2. In other aspects, the composition comprises any two peptides described in Table 2. In other aspects, the composition included, any 3, 4, 5, 6, 7, 8, 9, 10, 11, 12, 13, 14, 15, 16, 17, 18, or 19 peptides described in Table 2.

In a preferred aspect, a composition of the present disclosure can comprise at least one isolated synthetic peptide comprising SLGFCDTTNK (SEQ ID NO: 26), IAFSATR (SEQ ID NO: 29) or QTHQPPAPNSLIR (SEQ ID NO: 36). A composition can comprise at least one isolated synthetic peptide comprising at least two of SLGFCDTTNK (SEQ ID NO: 26), IAFSATR (SEQ ID NO: 29) or QTHQPPAPNSLIR (SEQ ID NO: 36). In yet other aspects, a composition can comprise at least one isolated synthetic peptide comprising each of SLGFCDTTNK (SEQ ID NO: 26), IAFSATR (SEQ ID NO: 29) or QTHQPPAPNSLIR (SEQ ID NO: 36).

In some aspects of the compositions of the present disclosure, the cysteine in the synthetic peptide SLGFCDTTNK (SEQ ID NO: 26) can be modified. The modification can be carbamidomethylation.

The present disclosure provides a composition comprising at least one transition ion pair, said composition comprising at least one transition ion pair of the protein C1q, wherein the at least one transition ion pair consists of a precursor ion with a corresponding m/z and a fragment ion with a corresponding ion m/z.

In some aspects of compositions of the present disclosure, the C1q protein can be human C1q protein. In other aspects, the C1q protein is *Macaca fascicularis* C1q protein. In yet another aspect, the C1q protein can be *Macaca mulatta*. The C1q protein can comprise any of the sequences show in Table 1.

The present disclosure provides a composition comprising at least one transition ion pair, said composition comprising at least one transition ion pair of the protein C1q, wherein the at least one transition ion pair consists of a precursor ion with a corresponding m/z and a fragment ion with a corresponding ion m/z, and wherein the transition ion pair is selected from precursor SLGFC (Cam) DTTNK (SEQ ID NO: 41) transition pair 571.8-942.3, precursor IAFSATR (SEQ ID NO: 29) transition pair 383.1-581.1 and precursor QTHQPPAPNSLIR (SEQ ID NO: 36) transition pair 487.0-350.3.

Definitions

As used herein, "m/z" indicates the mass-to-charge ratio of an ion.

As used herein, "MS/MS" represents tandem mass spectrometry, which is a type of mass spectrometry involving multiple stages of mass analysis with some form of fragmentation occurring in between the stages.

As used herein, "LC-SRM-MS" is an acronym for "selected reaction monitoring" and may be used interchangeably with "LC-MRM-MS" or "LC-SRM-MS/MS".

LC-SRM-MS is a highly selective method of tandem mass spectrometry which has the potential to effectively filter out all molecules and contaminants except the desired analyte(s). This is particularly beneficial if the analysis sample is a complex mixture which may comprise several isobaric species within a defined analytical window. LC-SRM-MS methods may utilize a triple quadrupole mass spectrometer which, as is known in the art, includes three quadrupole rod sets. A first stage of mass selection is performed in the first quadrupole rod set, and the selectively transmitted ions are fragmented in the second quadrupole rod set. The resultant transition (product) ions are conveyed to the third quadrupole rod set, which performs a second stage of mass selection. The product ions transmitted through the third quadrupole rod set are measured by a detector, which generates a signal representative of the numbers of selectively transmitted product ions. The RF and DC potentials applied to the first and third quadrupoles are tuned to select (respectively) precursor and product ions that have m/z values lying within narrow specified ranges. By specifying the appropriate transitions (m/z values of precursor and product ions), a peptide corresponding to a targeted protein may be measured with high degrees of sensitivity and selectivity. Signal-to-noise ratio in LC-SRM-MS is often superior to conventional tandem mass spectrometry (MS/MS) experiments that do not selectively target (filter) particular analytes but rather aim to survey all analytes in the sample.

LC-SRM-MS mass spectrometry involves the fragmentation of gas phase ions and occurs between the different stages of mass analysis. There are many methods used to fragment the ions and these can result in different types of fragmentation and thus different information about the structure and composition of the molecule. The transition ions observed in an LC-SRM-MS spectrum result from several different factors, which include, but are not limited to, the primary sequence, the amount of internal energy, the means of introducing the energy, and charge state. Transitions must carry at least one charge to be detected. An ion is categorized as either a, b or c if the charge is on a transition comprising the original N terminus of the peptide, whereas the ion is categorized as either x, y or z if the charge is on a transition comprising the original C terminus of the peptide. A subscript indicates the position of residues in the transition (e.g., first peptide residue in $x_1$ from C terminus, second peptide residues in $y_2$ from C terminus, and third peptide residues in $z_3$ from C terminus, etc.).

In a generic peptide repeat unit represented —N—C(O)—C—, an x ion and an a ion resulting from cleavage of the carbonyl-carbon bond (i.e., C(O)—C). The x ion is an acylium ion, and the a ion is an iminium ion. A y ion and a b ion result from cleavage of the carbonyl-nitrogen bond (i.e., C(O)—N, also known as the amide bond). In this case, the y ion is an ammonium ion and the b ion is an acylium ion. Finally, a z ion and a c ion result from cleavage of the nitrogen-carbon (i.e., C—N) bond. The z ion is a carbocation and the c ion is an ammonium ion.

Superscripts are sometimes used to indicate neutral losses in addition to the backbone fragmentation, for example, * for loss of ammonia and ° for loss of water. In addition to protons, c ions and y ions may abstract an additional proton from the precursor peptide. In electrospray ionization, tryptic peptides may carry more than one charge.

Internal transitions arise from double backbone cleavage. These may be formed by a combination of b-type and y-type cleavage (i.e., cleavage producing b and y ions). Internal cleavage ions may also be formed by a combination of a-type and y-type cleavage. An internal transition with a single side chain formed by a combination of a-type and y-type cleavage is called an iminium ion (sometimes also referred to as an imonium or immonium ion). These ions are labeled with the one letter code for the corresponding amino acid.

Low energy CID (i.e., collision induced dissociation in a triple quadrupole or an ion trap) involves the fragmentation of a peptide carrying a positive charge, primarily along its backbone, to generate primarily a, b and y ions.

One or more liquid chromatography (LC) purification steps are performed prior to a subsequent LC-SRM-MS analysis step. Traditional LC analysis relies on the chemical interactions between sample components and column packing materials, where laminar flow of the sample through the column is the basis for separation of the analyte of interest from the test sample. The skilled artisan will understand that separation in such columns is a diffusional process. A variety of column packing materials are available for chromatographic separation of samples, and selection of an appropriate separation protocol is an empirical process that depends on the sample characteristics, the analyte of interest, the interfering substances present and their characteristics, etc. Various packing chemistries can be used depending on the needs (e.g., structure, polarity, and solubility of compounds being purified). In various aspects the columns are polar, ion exchange (both cation and anion), hydrophobic interaction, phenyl, C-2, C-8, C-18 columns, polar coating on porous polymer, or others that are commercially available. During chromatography, the separation of materials is affected by variables such as choice of eluent (also known as a "mobile phase"), choice of gradient elution and the gradient conditions, temperature, etc. In certain aspects, an analyte may be purified by applying a sample to a column under conditions where the analyte of interest is reversibly retained by the column packing material, while one or more other materials are not retained. In these aspects, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. As discussed above, such procedures may enrich the amount of one or more analytes of interest relative to one or more other components of the sample.

The following parameters are used to specify an LC-SRM-MS assay of a protein under a particular LC-SRM-MS system: (1) a tryptic peptide of the protein; (2) the retention time (RT) of the peptide; (3) the m/z value of the peptide precursor ion; (4) the declustering potential used to ionize the precursor ion; (5) the m/z value of a fragment ion generated from the peptide precursor ion; and (6) the collision energy (CE) used to fragment the peptide precursor ion that is optimized for the particular peptide.

As used herein, "ISP" refers to "internal standard peptides".

To facilitate accurate quantification of the peptide transitions by the methods disclosed herein, a set of isotopically-labeled synthetic versions of the peptides of interest may be added in known amounts to the sample for use as internal standards. Since the isotopically-labeled peptides have physical and chemical properties identical to the corresponding surrogate peptide, they co-elute from the chromatographic column and are easily identifiable on the resultant mass spectrum. The addition of the labeled standards may occur before or after proteolytic digestion. Methods of synthesizing isotopically-labeled peptides will be known to those of skill in the art. Thus, in some aspects, the experimental samples contain internal standard peptides. Other aspects may utilize external standards or other expedients for peptide quantification.

As used herein, a "tryptic peptide" refers to the peptide that is formed by the treatment of a protein with trypsin.

As used herein, the term "standard curve" may be used interchangeably with the term "calibration curve".

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless defined otherwise, all technical and scientific terms used herein have the same meaning as commonly understood by one of ordinary skill in the art to which the invention pertains. Although other probes, compositions, methods, and kits similar, or equivalent, to those described herein can be used in the practice of the present disclosure, the preferred materials and methods are described herein. It is to be understood that the terminology used herein is for the purpose of describing particular aspects only, and is not intended to be limiting.

EXAMPLES

Example 1—Determining a C1q Concentration Standard Curve Using the Methods of the Present Disclosure The methods of the present disclosure were used to generate standard curves, also referred to as a calibration curves, using a set of C1q reference solutions of known C1q concentrations, including C1q standard and quality control (QC) samples. The sensitivity and accuracy of the methods of the present disclosure were also tested.

The calibration curves were generated using C1q standard samples that were prepared and applied using the following guidelines:

Purified C1q protein was diluted in the same biological matrix as experimental samples,
  The set of C1Q reference solutions tested consisted of a double blank, a blank, and at least 6 non-zero concentrations of C1q;
  The lower limit of quantitation (LLOQ) is defined the concentration of C1q protein at which the measured response of the LLOQ sample is at least 5 times compared to the response of the blank sample, such that the accuracy is within 25% of the nominal concentration and the coefficient of variation is less than 25%;

The upper limit of quantitation (ULOQ) is defined such that the accuracy is within 20% of the nominal concentration, and the coefficient of variation is less than 20%.

The calibration curves were generated using C1q QC samples that were prepared and applied using the following guidelines:

- At least 3 concentrations of QC samples were prepared and used for calibration;
- Each QC sample was prepared in duplicate;
- The QC samples covered the low, medium and high quantitation range of the assay, and the low QC (LQC) sample was within 3 times the concentration of LLOQ;
- The accuracy of at least 67% of QC samples was within 20% of nominal concentration;
- The accuracy of at least 50% of QC samples at each level was within 20% of nominal concentration;
- The minimum number of QC samples was equal to the greater of at least 5% of the number of unknown samples or 6 total QC samples;
- The QC samples were prepared with a C1q stock solution that was separate from the stock solution for the preparation of C1q reference solutions.

Materials:
- Purified Human Complement Protein C1q (Quidel, Item #A400)
- Complement C1q-Depleted Serum, Human (Sigma-Aldrich, Cat #234401-1ML)
- SLGFC (Cam) DTTNK (SEQ ID NO: 41) (New England Peptide)
- IAFSATR (SEQ ID NO: 29) (New England Peptide)
- QTHQPPAPNSLIR (SEQ ID NO: 36) (New England Peptide)
- Bispecific monoclonal antibody drug candidate
- Sequencing grade modified trypsin supplied with resuspension buffer (Promega, Cat #. V5117)
- UltraPure 1.0 M Tris-HCl pH 7.5 (Invitrogen, Cat #15567-027).
- UltraPure 1.0 M Tris-HCl pH 8.0 (Invitrogen, Cat #15568-025).
- UltraPure 1.0 M Tris-HCl pH 8.5 (Alfa Aesar, Cat #J61038)
- Urea (Sigma Aldrich, Cat #U5128-100G)
- TCEP HCL (Thermo Scientific; Cat #20491)
- Iodoacetamide (Sigma-Aldrich; Cat #A3221-10VL).
- Formic acid (Thermo Scientific; Cat #28905)
- Acetonitrile (Fisher Chemical, Cat #A955-4).
- ACQUITY UPLC BEH130 C18 column, 1.7 µm, 2.1 mm×50 mm (Waters, Part #1860035554)
- 96 well plate, 0.5 mL, Polypropylene (Agilent, Part #5042-1386)
- 25 mL Disposable Reagent Reservoir (VistaLab, Part #3054-1004)
- TripleQuad Mass Spectrometer (Agilent, Model #6495)
- 1290 Infinity II LC System (Agilent, Model #1290)

Sample Preparation

A 200 µg/mL C1q stock solution was prepared in C1q-deplete human serum and assay dilution buffer (ADB) containing 20 µg/mL of the bispecific monoclonal antibody drug candidate. The C1q stock solution was serially diluted 1 to 3, six times to prepare six C1q standard solutions (L6-L1). The LLOQ (lower limit of quantitation), low QC, medium QC, high QC, and ULOQ (upper limit of quantitation) samples were prepared in ADB independently from C1q stock solution. An aliquot of ADB was reserved as an L0 (blank) sample. The concentrations of the C1q standard and QC solutions are listed in Table 3.

TABLE 3

The concentrations of C1q standard and QC solutions.

| Level/QC | Concentration (µg/mL) |
|---|---|
| L1/LLOQ | 0.27 |
| L2 | 0.82 |
| L3 | 2.47 |
| L4 | 7.41 |
| L5 | 22.22 |
| L6/ULOQ | 66.67 |
| LQC | 0.78 |
| MQC | 6.25 |
| HQC | 50 |

The following isotope-labelled internal standard peptides (ISPs) were reconstituted to 6-12 mM in 30% acetonitrile in 0.1% formic acid to create isotope-labelled ISP solutions: SLGFC (Cam) DTTNK (SEQ ID NO: 41), IAFSATR (SEQ ID NO: 29), and QTHQPPAPNSLIR (SEQ ID NO: 36).

Each C1q sample was diluted by 50 times in 100 mM Tris-HCl, pH 7.5 and 20 µg/mL of the bispecific antibody. 5 µL of each diluted C1q sample was then denatured and reduced in 20 µL of 8 M urea and 10 mM tris (2-carboxyethyl) phosphine (TCEP) at 56° C. with shaking for 30 minutes. 5 µL of 50 mM iodoacetamide was then added to each sample, and the samples were then incubated in the dark at 25° C. with shaking for 30 minutes. 10 µL of the appropriate isotope-labelled ISP solution was then added to each sample. After addition of the ISPs, 100 µL of 0.01 µg/µL trypsin was also added to each sample. The samples were then incubated at 37° C. in the dark with shaking for 4 hours. 5 µL of 20% of formic acid was added to the samples to quench the tryptic digestion reaction. The samples were mixed and centrifuged at 4680 rpm for 5 minutes before being analyzed by LC-SRM-MS/MS.

LC-SRM-MS Analysis

The LC-SRM-MS analysis was performed on a TripleQuad Mass Spectrometer (Agilent, Model #6495) with a 1290 Infinity II LC system (Agilent, Model #1290). The LC gradient used is described in Table 4, wherein Buffer A consisted of 0.1% formic acid in water, and Buffer B consisted of 0.1% formic acid in acetonitrile.

TABLE 4

LC gradient

| Time (minute) | Buffer A (%) | Buffer B (%) | Flow (mL/minute) |
|---|---|---|---|
| 0.5 | 97 | 3 | 0.4 |
| 8.0 | 75 | 25 | 0.4 |
| 8.1 | 10 | 90 | 0.4 |
| 10.5 | 10 | 90 | 0.4 |
| 10.6 | 97 | 3 | 0.4 |
| 13.0 | 97 | 3 | 0.4 |

The SRM-MS analysis simultaneously monitored native C1q peptide fragments and isotope-labelled peptides in the samples. Peak areas for two transitions (native and heavy label) were collected and reported for both native and isotope-labelled C1q peptides. For each C1q standard and QC samples, the data output for C1q protein analyzed by LC-SRM-MS yielded six measurements consisting of two transition measurements (native and heavy label) from each of three selected peptides set forth in Table 5 below.

TABLE 5

The m/z transition and collision energy of C1q target peptides.

| C1q sub-unit | Peptide sequence | SEQ ID NO | m/z transition | Collision energy (V) |
|---|---|---|---|---|
| A | SLGFC(Cam)DTTNK | 41 | 571.8 > 942.3 | 18 |
| B | IAFSATR | 29 | 383.1 > 581.1 | 10 |
| C | QTHQPPAPNSLIR | 36 | 487.0 > 350.3 | 13 |

Each of the three peptides in Table 5 are from a different subunit of C1q. The peptide fragment derived from subunit B was used as the quantitation peptide (herein referred to as the subunit B peptide), and the peptide fragments derived from subunits A (herein referred to as the subunit A peptide) and C (herein referred to as the subunit C peptide) were used as confirmatory peptides. The isotope-labelled ISPs have amino acid sequences that are identical to each of the three selected peptides and are herein referred to as the isotope-labeled subunit A control peptide, the isotope-labeled subunit B control peptide, and the isotope-labeled subunit C control peptide.

Figure 2:
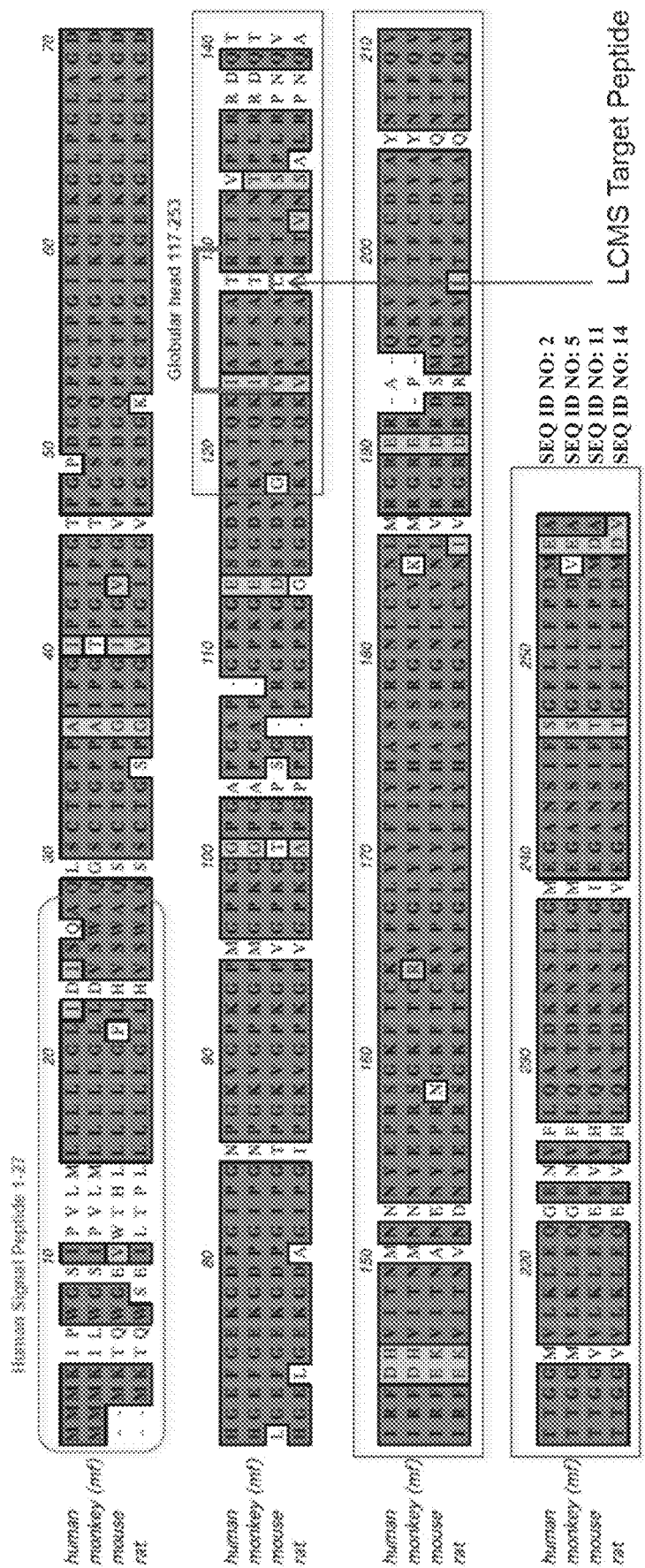
FIG. 2 is the amino acid sequence alignment of the B subunit of C1q from human, monkey, mouse and rat.
Figure 3:
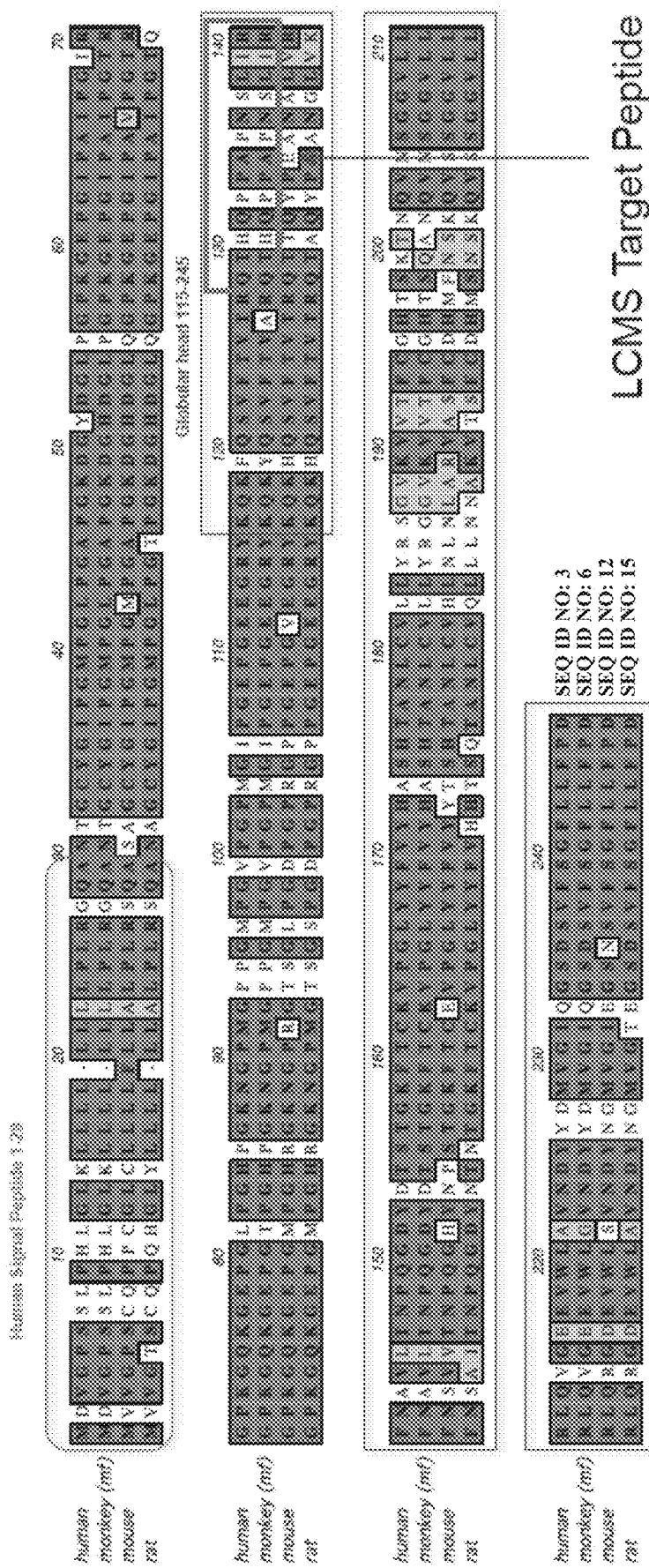
FIG. 3 is the amino acid sequence alignment of the C subunit of C1q from human, monkey, mouse and rat.

The three peptides listed in Table 5 were selected based previous results which had shown that these peptides were the best peptides for quantifying C1q concentration in a LC-SRM-MS/MS assay. The selection of these peptides was partly based on conservation of the peptide sequence between humans and monkey (*Macaca fascicularis*). FIG. 1 shows a sequence alignment of subunit A of human, monkey (*Macaca fascicularis*), mouse and rat C1q highlighting the subunit A peptide. FIG. 2 shows a sequence alignment of subunit B of human, monkey (*Macaca fascicularis*), mouse and rat C1q highlighting the subunit B peptide. FIG. 3 shows a sequence alignment of subunit C of human, monkey (*Macaca fascicularis*), mouse and rat C1q highlighting the subunit C peptide. Multiple tryptic peptides from each of the A, B and C subunits of C1q were initially tested. The tested peptides are listed in Table 2.

Results

Each C1q standard sample and each C1q QC sample were analyzed using LC-SRM-MS/MS. For each sample, 6 signals were recorded: the signal corresponding to the native subunit A peptide, the signal corresponding to the native subunit B peptide, the signal corresponding to the native subunit C peptide, the signal corresponding to the isotope-labeled subunit A control peptide, the signal corresponding to the isotope-labeled subunit B control peptide and the signal corresponding to the isotope-labeled subunit C control peptide. The data for isotope-labelled peptides were used as internal controls for assay performance troubleshooting purposes.

Figure 4:
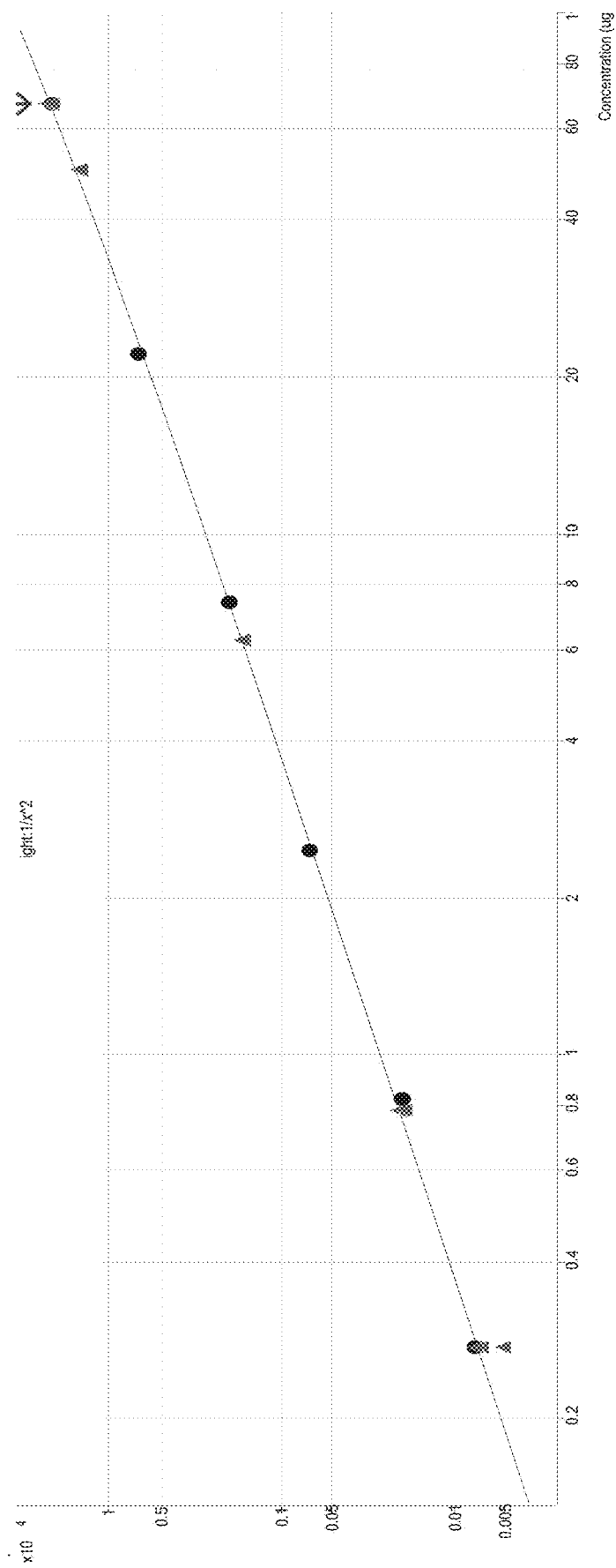
FIG. 4 is a calibration curve generated using the methods of the present disclosure and a peptide derived from the A subunit of the C1q protein.
Figure 5:
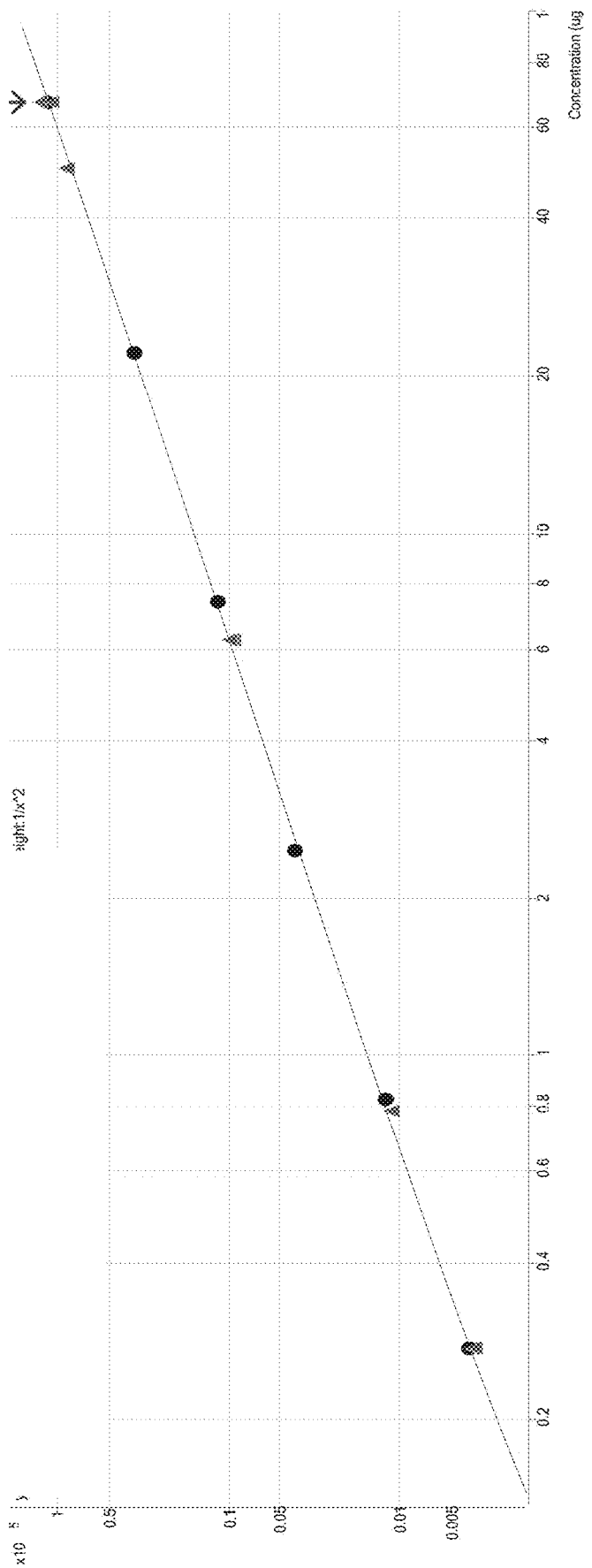
FIG. 5 is a calibration curve generated using the methods of the present disclosure and peptide derived from the B subunit of the C1q protein.
Figure 6:
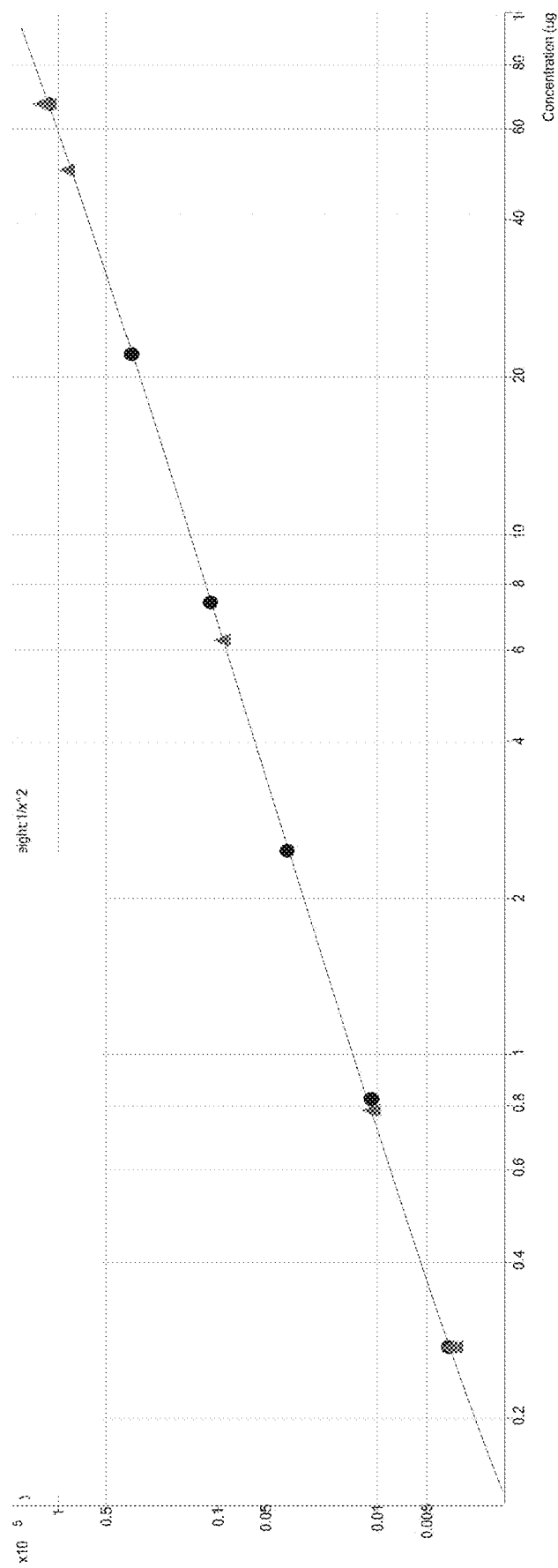
FIG. 6 is a calibration curve generated using the methods of the present disclosure and a peptide derived from the C subunit of the C1q protein.
Figure 7A:
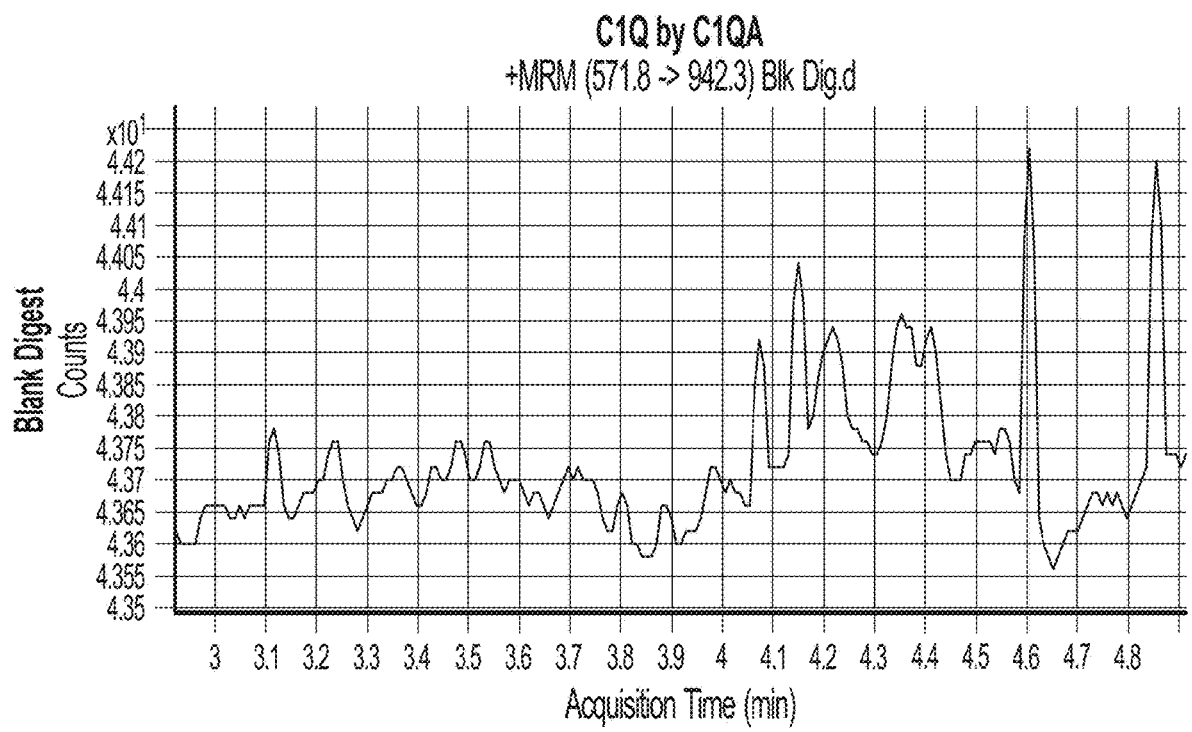
FIG. 7A, FIG. 7B, FIG. 7C, FIG. 7D, FIG. 7E and FIG. 7F are a series of LC-SRM-MS/MS chromatograms of selected peptides derived from the A, B, and C subunits of C1q in blank digest, double blank, blank, and Lower Limit of Quantitation (LLOQ) samples.
Figure 7A:
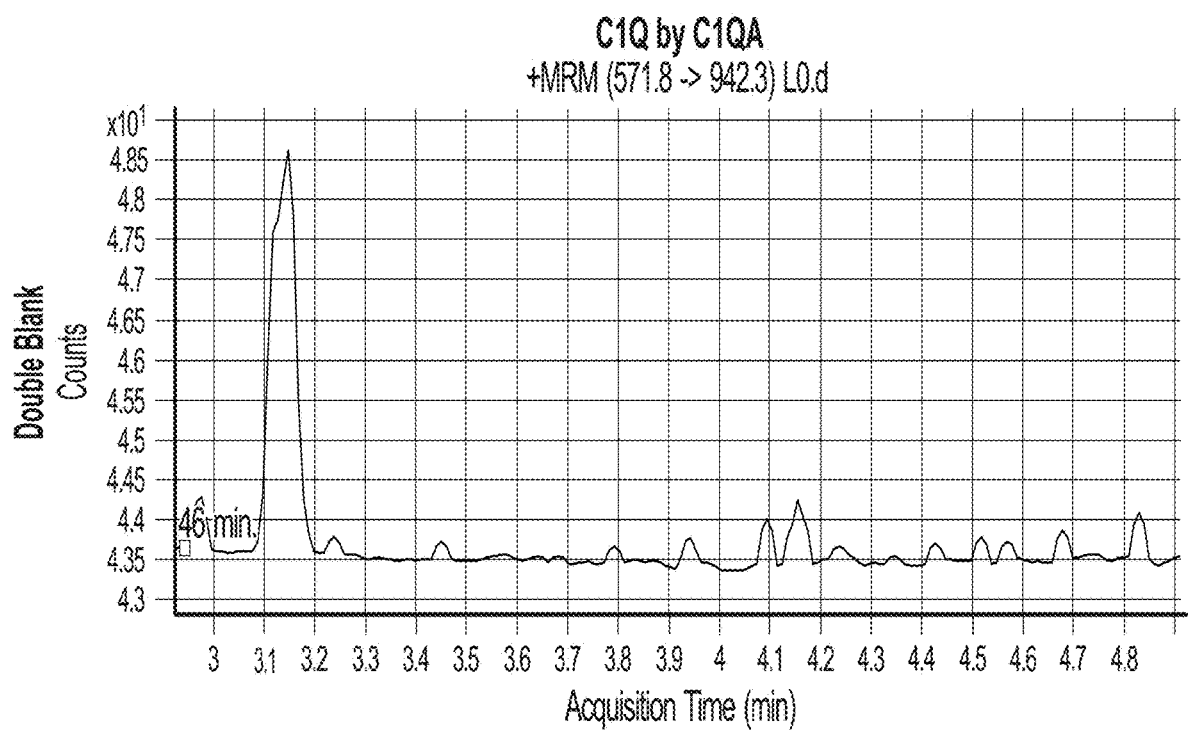
Figure 7B:
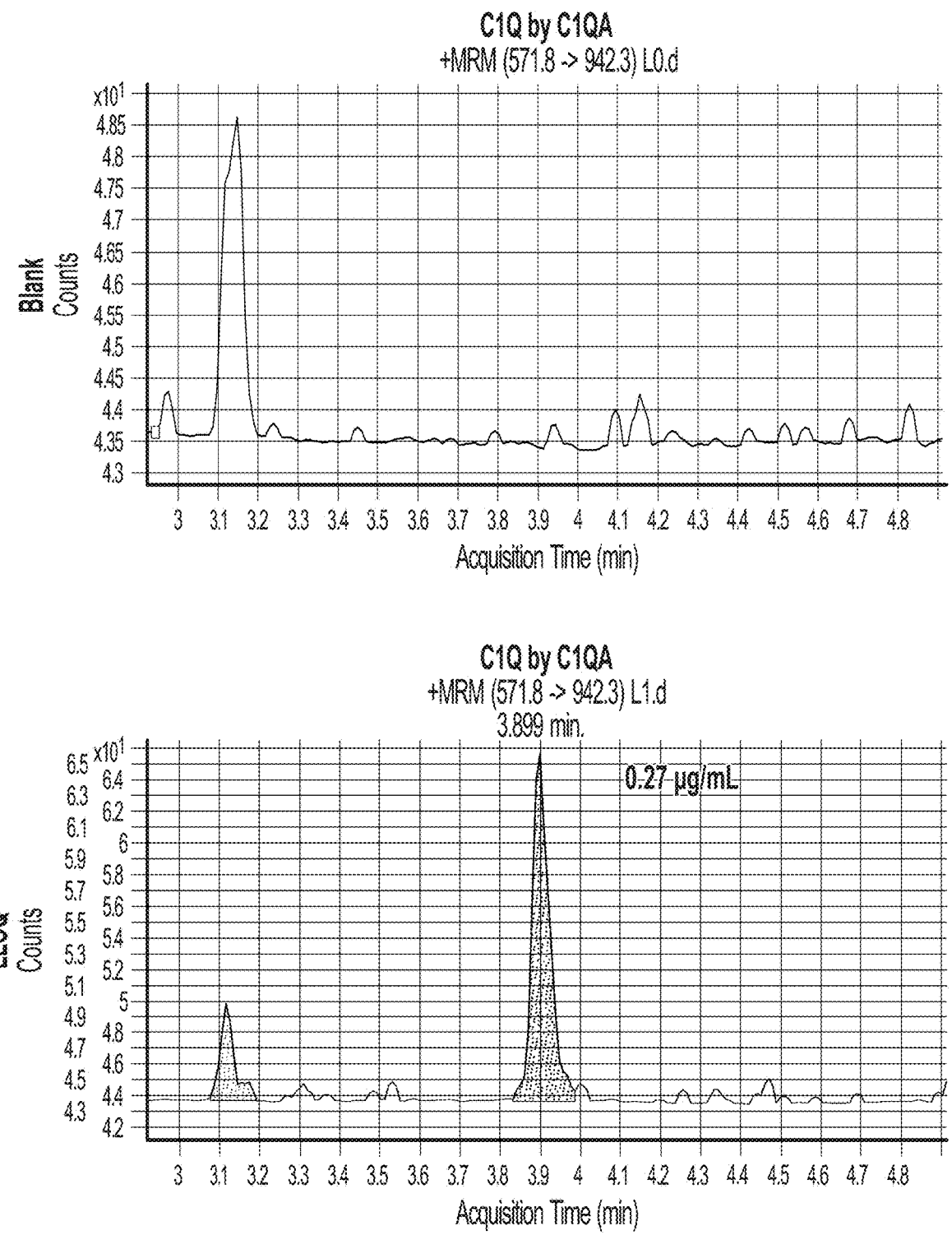
Figure 7C:
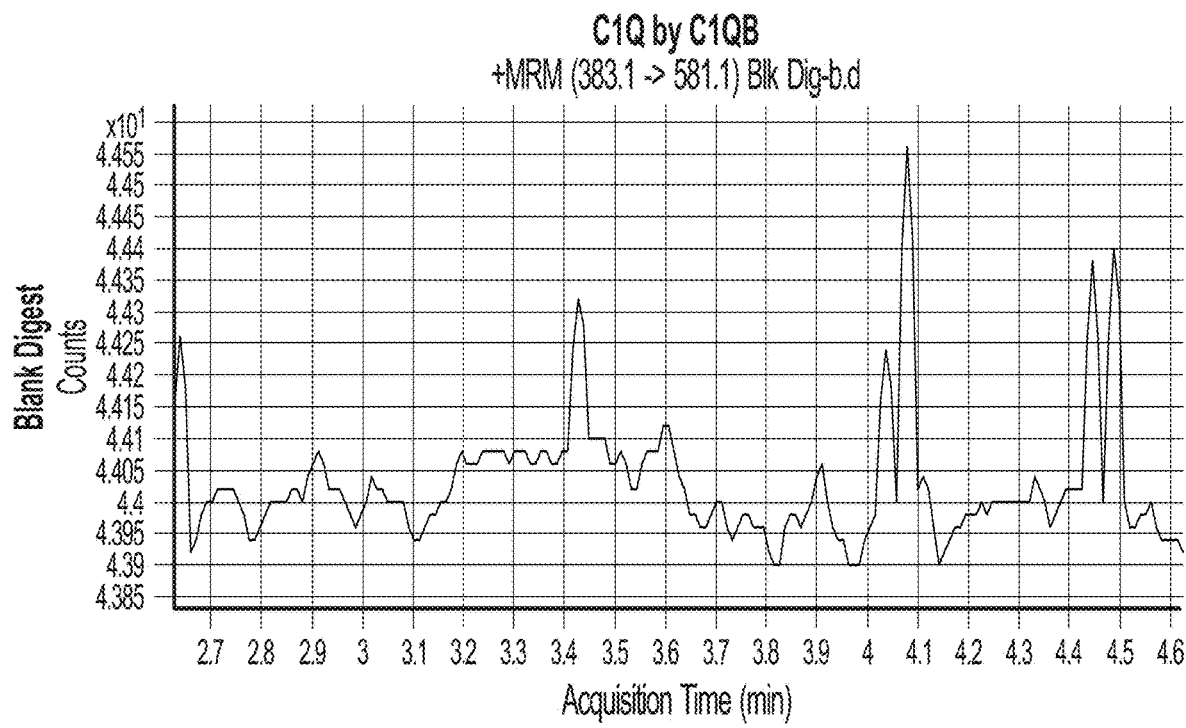
Figure 7C:
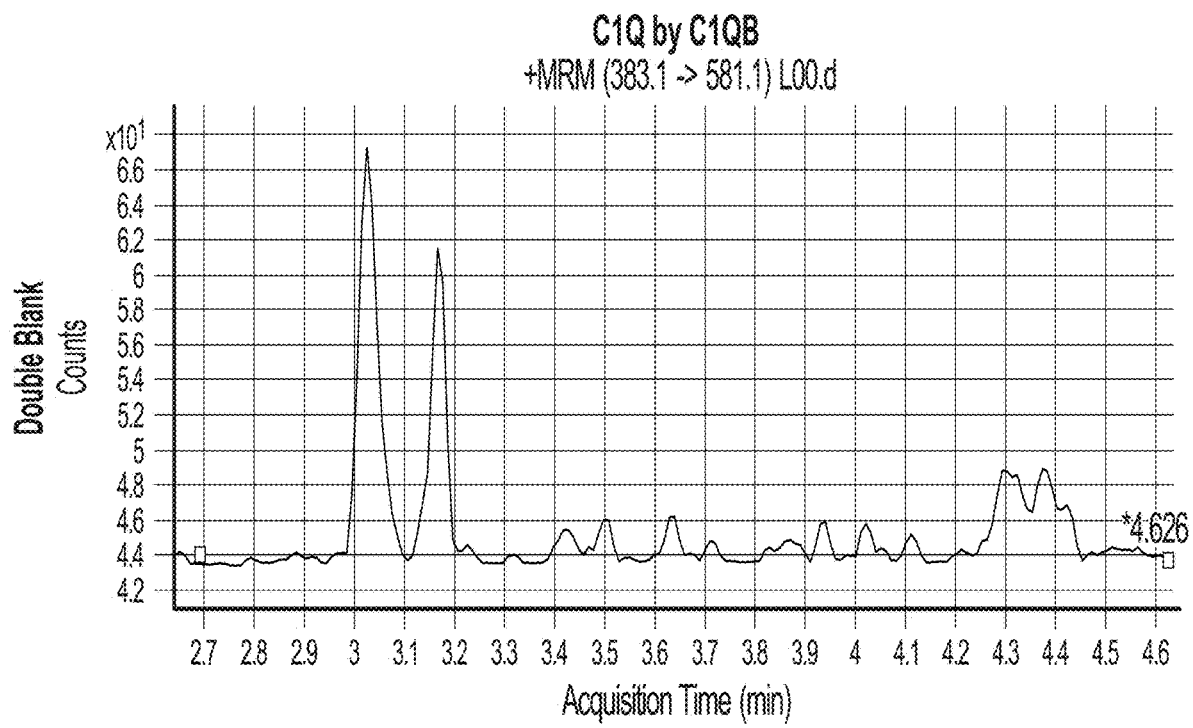
Figure 7D:
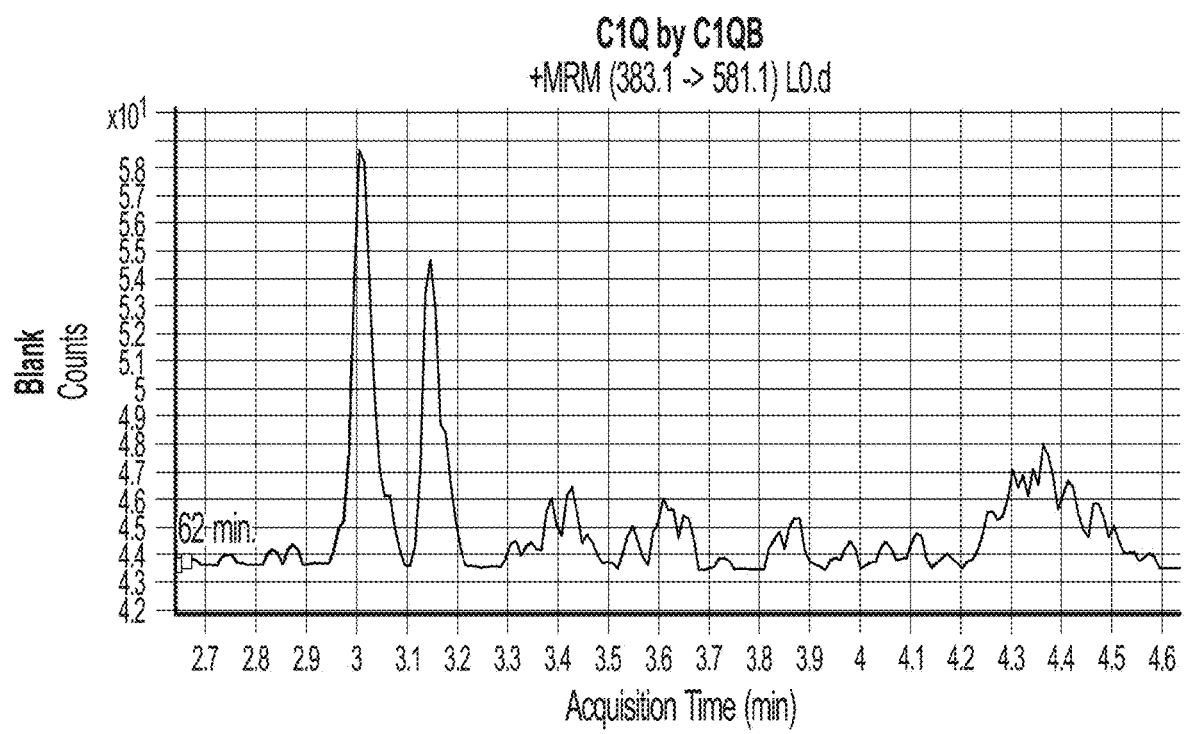
Figure 7D:
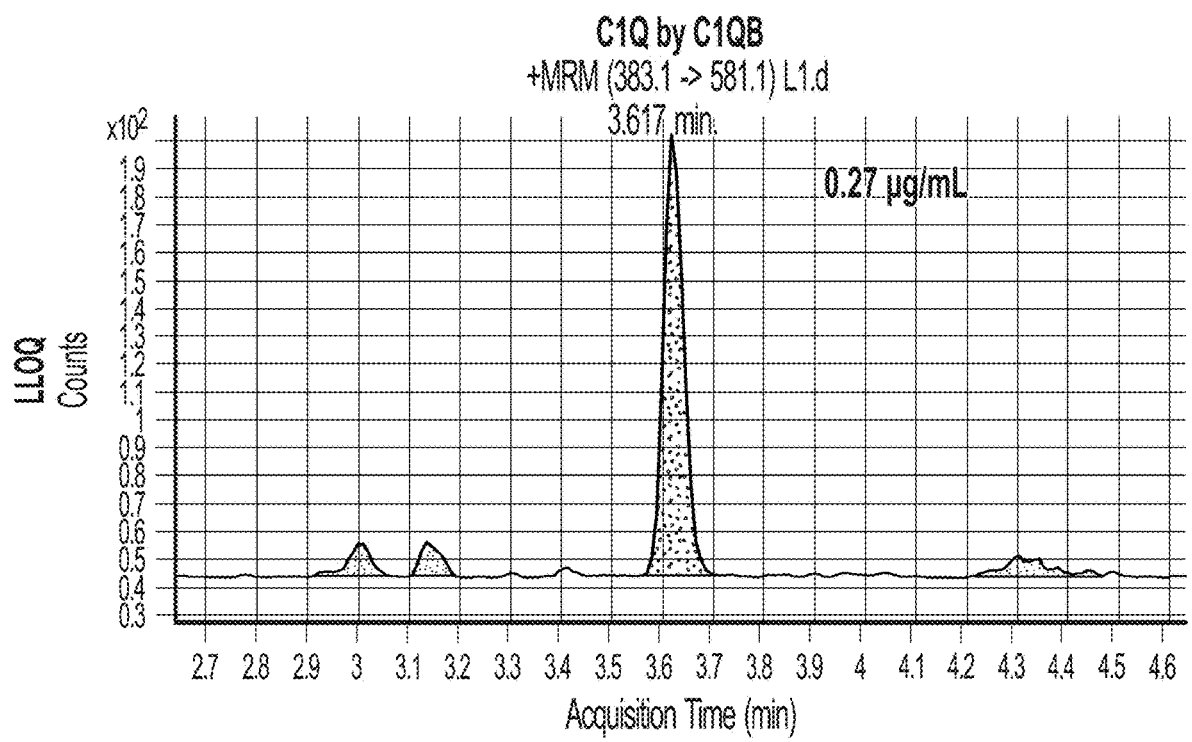
Figure 7E:
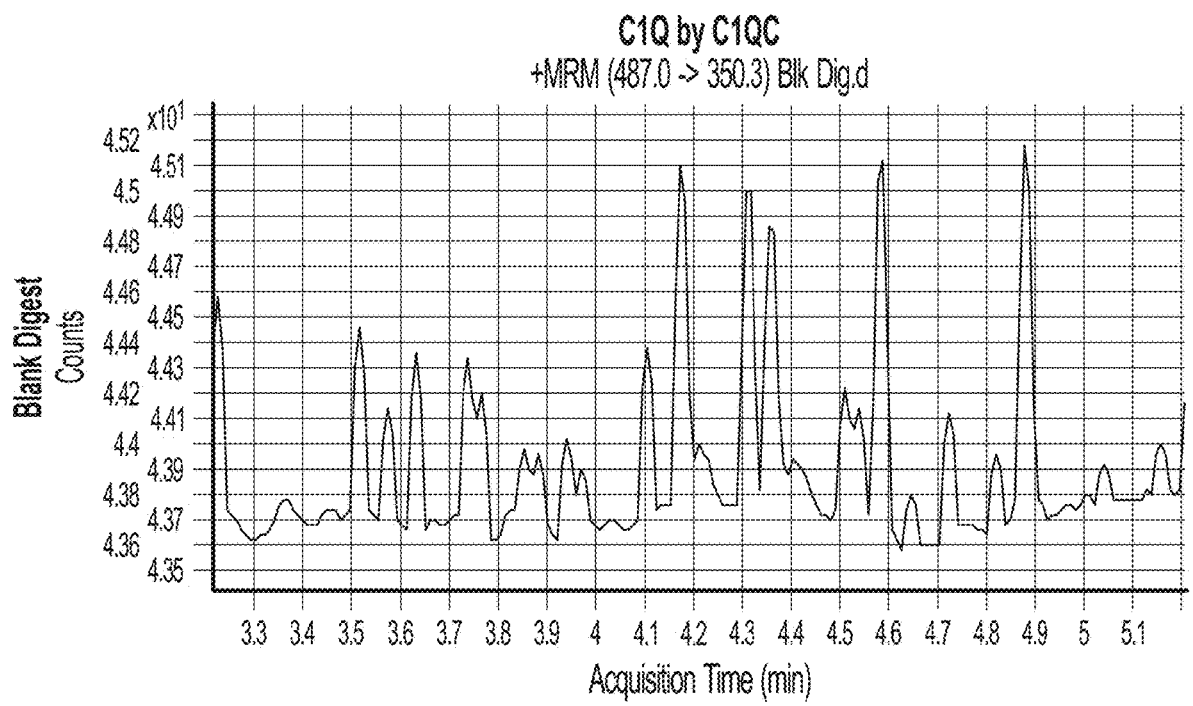
Figure 7E:
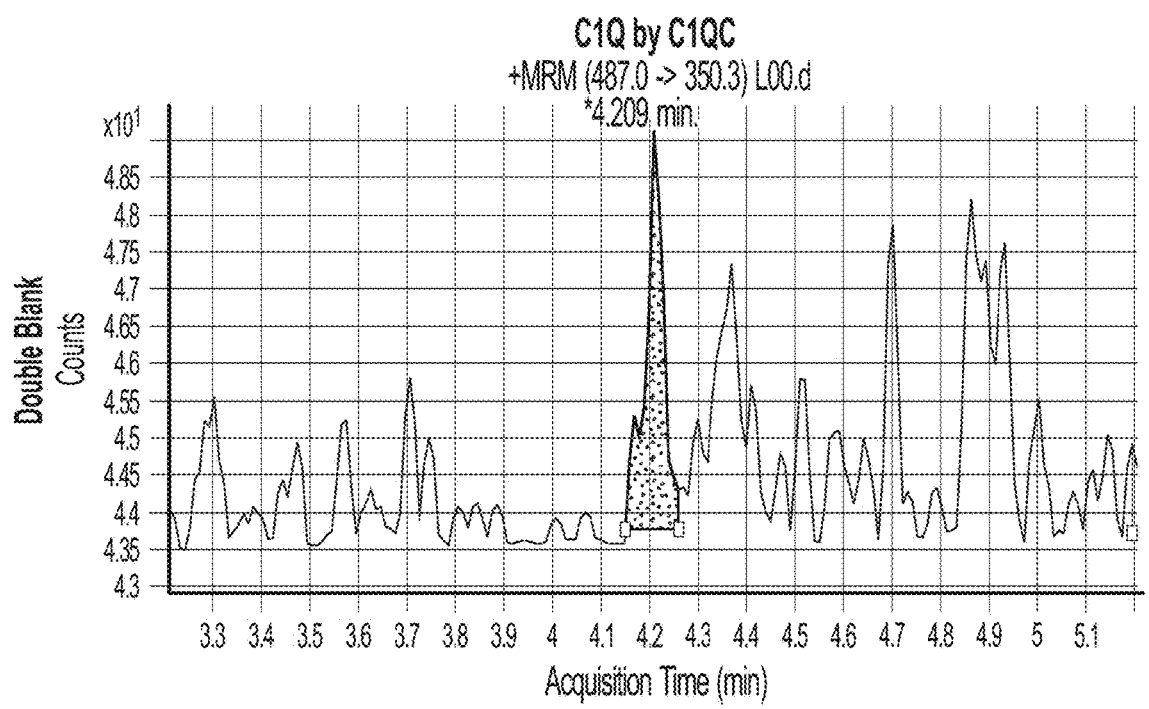
Figure 7F:
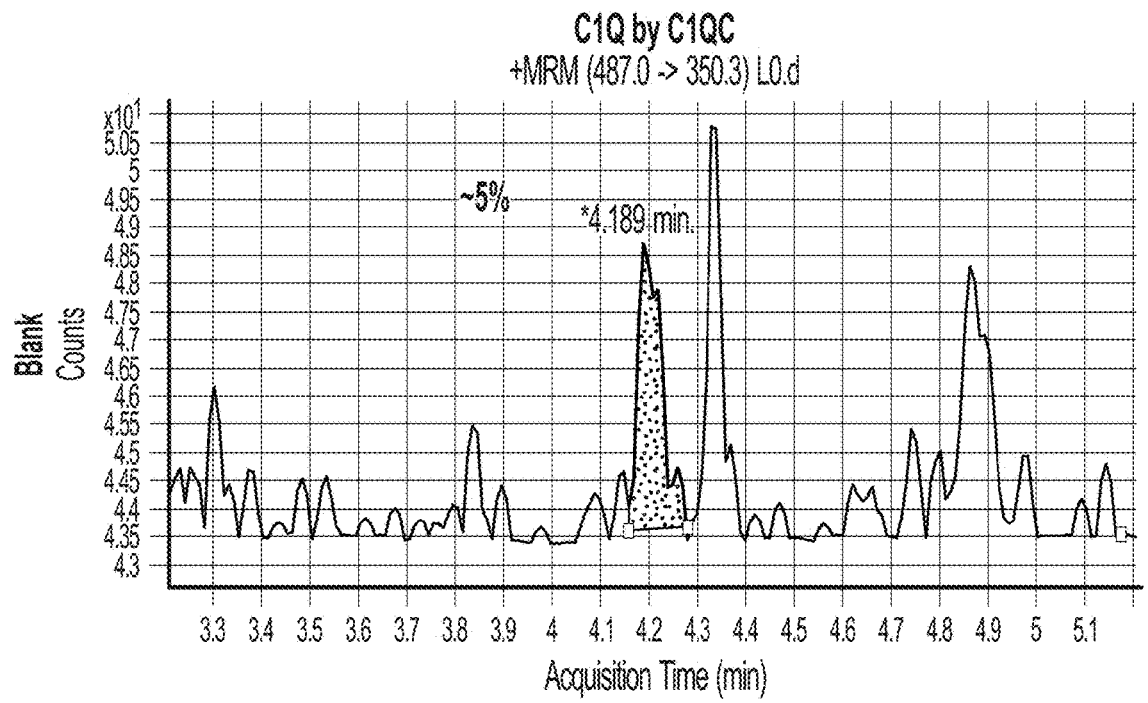
Figure 7F:
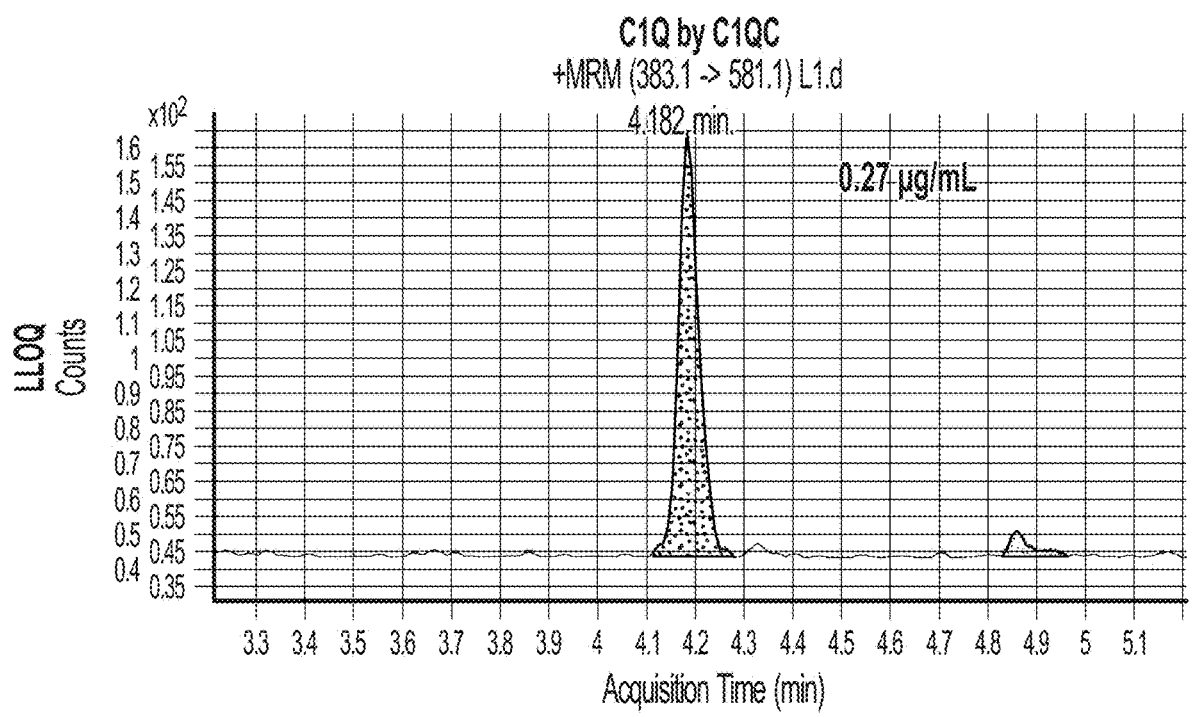

For each of the three selected peptides (the subunit A peptide, the subunit B peptide, and the subunit C peptide), a calibration curve was generated by plotting the normalized LC-SRM-MS signal recorded from C1q standard samples against the corresponding nominal concentrations of those samples. FIG. 4 shows the calibration curve generated using the signal corresponding to the subunit A peptide. FIG. 5 shows the calibration curve generated using the signal corresponding to the subunit B peptide. FIG. 6 shows the calibration curve generated using the signal corresponding to the subunit C peptide. For FIGS. 4-6, the black dots represent C1q standard samples at concentrations L1-L6. The blue triangles represent C1q QC samples at LLOQ, LQC, MQC, HQC, and ULOQ concentrations.

After generating the calibration curve, the concentrations of QC samples were then determined by comparing the LC-SRM-MS/MS signal of each of the three target peptides in the QC samples to the corresponding calibration curve. The accuracy of the assay was assessed by comparing the determined concentrations to the nominal concentrations of the QC samples. The results of the comparison is shown in Tables 6-8.

TABLE 6

Assay accuracy using target peptide SLGFC(Cam)DTTNK (SEQ ID NO: 41) derived from C1q A subunit.

| Standards | L1 | L2 | L3 | L4 | L5 | L6 |
|---|---|---|---|---|---|---|
| Nominal Conc. (µg/mL) | 0.27 | 0.82 | 2.47 | 7.41 | 22.22 | 66.67 |
| Accuracy (%) | 103 | 91 | 104 | 100 | 104 | 99 |
| QC (N = 3) | LLOQ | LQC | MQC | HQC | ULOQ | |
| Nominal Conc. (µg/mL) | 0.27 | 0.78 | 6.25 | 50 | 66.67 | |
| Accuracy (%)-Set1 | 96 | 99 | 97 | 95 | 97 | |
| Accuracy (%)-Set2 | 102 | 94 | 100 | 96 | 102 | |
| Accuracy (%)-Set3 | 71 | 101 | 101 | 97 | 104 | |
| % RSD (N = 3) | 19% | 4% | 2% | 1% | 4% | |

TABLE 7

Assay accuracy using target peptide IAFSATR (SEQ ID NO: 29) derived from C1q B subunit.

| Standard | L1 | L2 | L3 | L4 | L5 | L6 |
|---|---|---|---|---|---|---|
| Nominal Conc. (µg/mL) | 0.27 | 0.82 | 2.47 | 7.41 | 22.22 | 66.67 |
| Accuracy (%) | 101 | 95 | 106 | 98 | 99 | 100 |
| QC (N = 3) | LLOQ | LQC | MQC | HQC | ULOQ | |
| Nominal Conc. (µg/mL) | 0.27 | 0.78 | 6.25 | 50 | 66.67 | |
| Accuracy (%)-Set1 | 98 | 95 | 97 | 105 | 96 | |
| Accuracy (%)-Set2 | 94 | 94 | 100 | 106 | 111 | |
| Accuracy (%)-Set3 | 99 | 94 | 95 | 109 | 113 | |
| % RSD (N = 3) | 3% | 1% | 3% | 2% | 9% | |

TABLE 8

Calibration of C1q assay based on target peptide QTHQPPAPNSLIR (SEQ ID NO: 36) derived from C1q C subunit.

| Standard | L1 | L2 | L3 | L4 | L5 | L6 |
|---|---|---|---|---|---|---|
| Nominal Conc. (µg/mL) | 0.27 | 0.82 | 2.47 | 7.41 | 22.22 | 66.67 |
| Accuracy (%) | 101 | 95 | 103 | 100 | 101 | 100 |
| QC (N = 3) | LLOQ | LQC | MQC | HQC | ULOQ | |
| Nominal Conc. (µg/mL) | 0.27 | 0.78 | 6.25 | 50 | 66.67 | |
| Accuracy (%)-Set1 | 98 | 98 | 99 | 106 | 99 | |
| Accuracy (%)-Set2 | 104 | 101 | 103 | 105 | 110 | |
| Accuracy (%)-Set3 | 93 | 97 | 102 | 107 | 111 | |
| % RSD (N = 3) | 6% | 2% | 2% | 1% | 6% | |

These results demonstrate that the assay is both accurate and sensitive. They also demonstrate that using the peptide IAFSATR (SEQ ID NO: 29) derived from subunit B of C1q provided the best results, as there was a high response recorded by LC-SRM-MS/MS and the signal was free of background interference.

LLOQ and Limit of Detection (LOD)

Figure 8A:
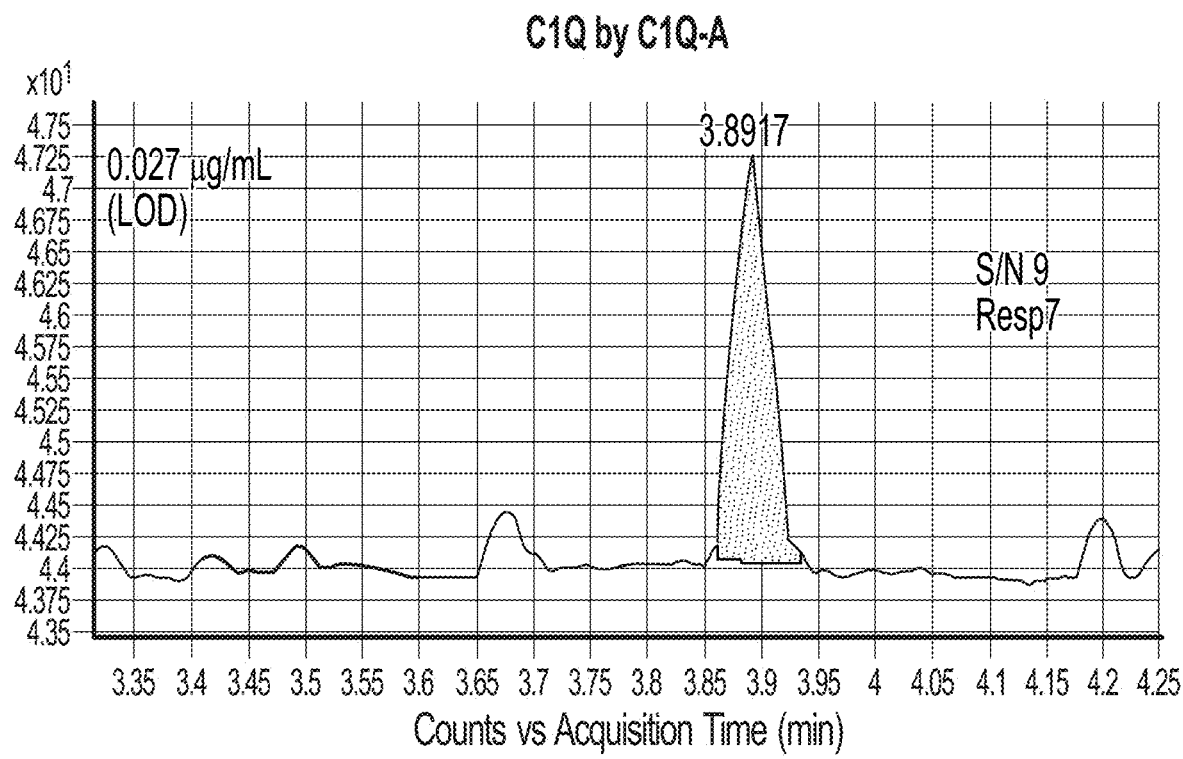
FIG. 8A, FIG. 8B and FIG. 8C are a series of LC-SRM-MS/MS chromatograms of selected peptides derived from the A, B, and C subunits of C1q in Limit of Detection (LOD) and LLOQ samples showing the signal to noise and response values for the highlighted peaks.
Figure 8A:
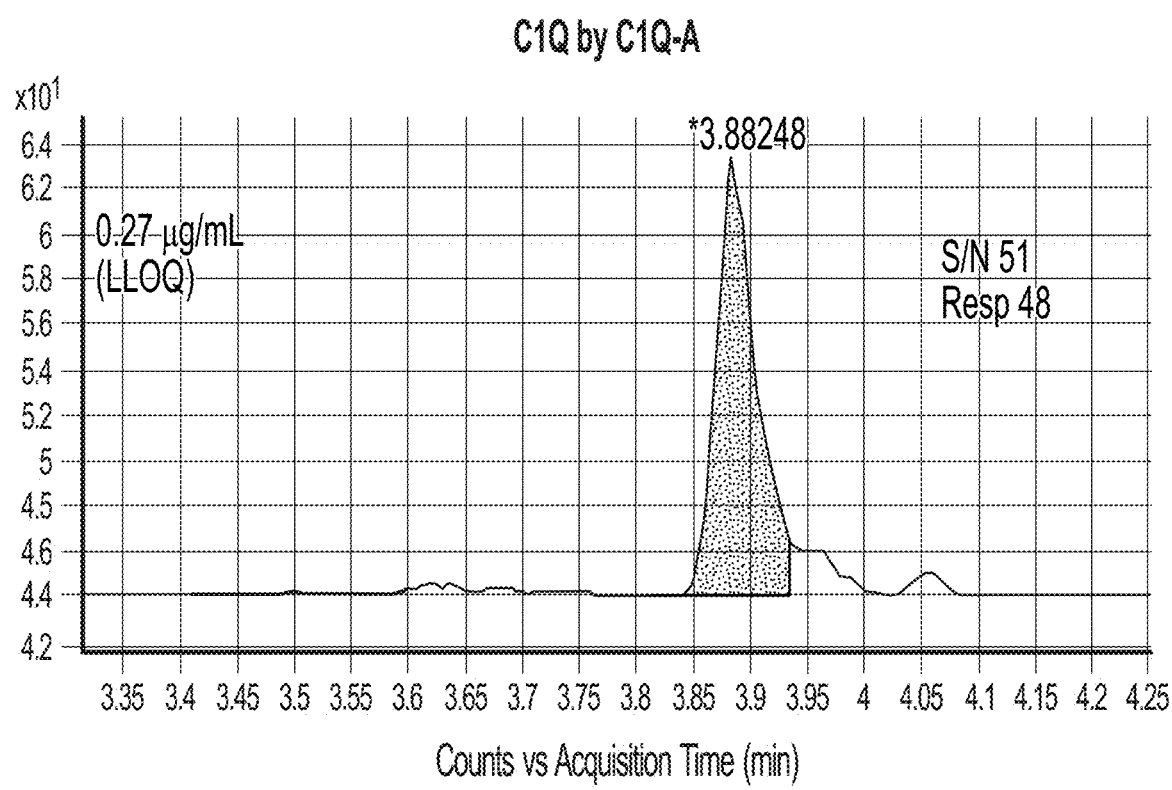
Figure 8B:
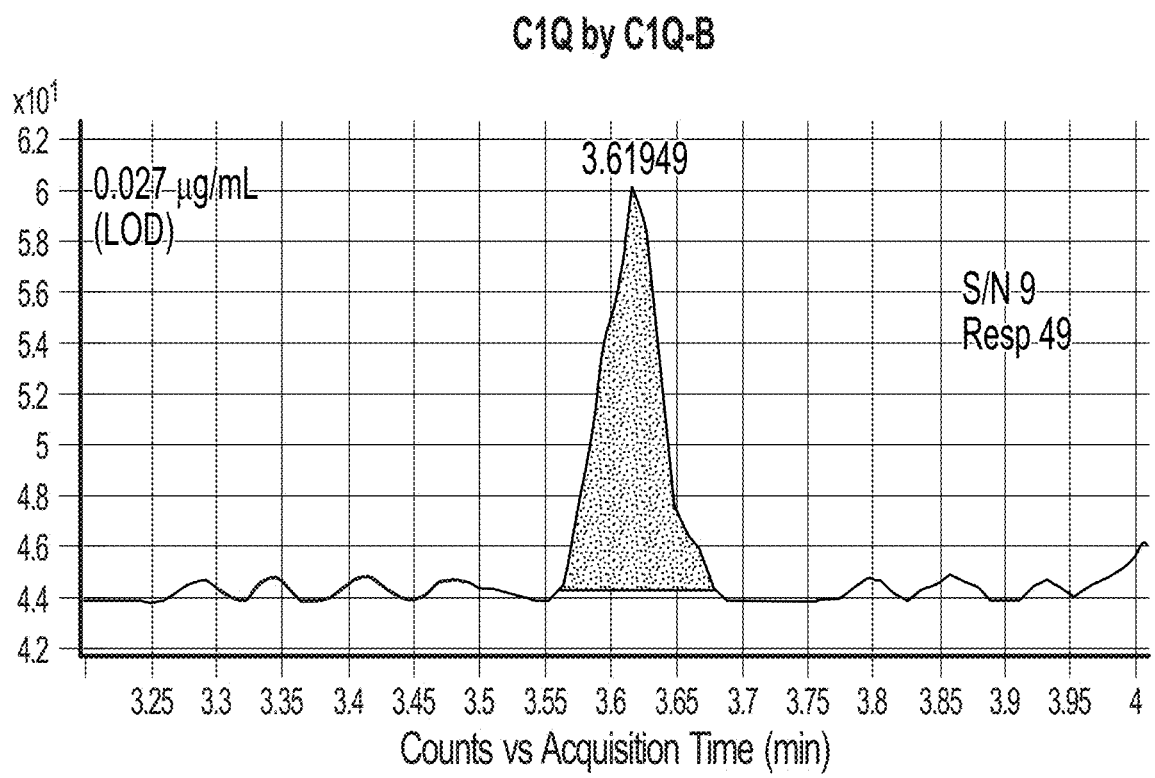
Figure 8B:
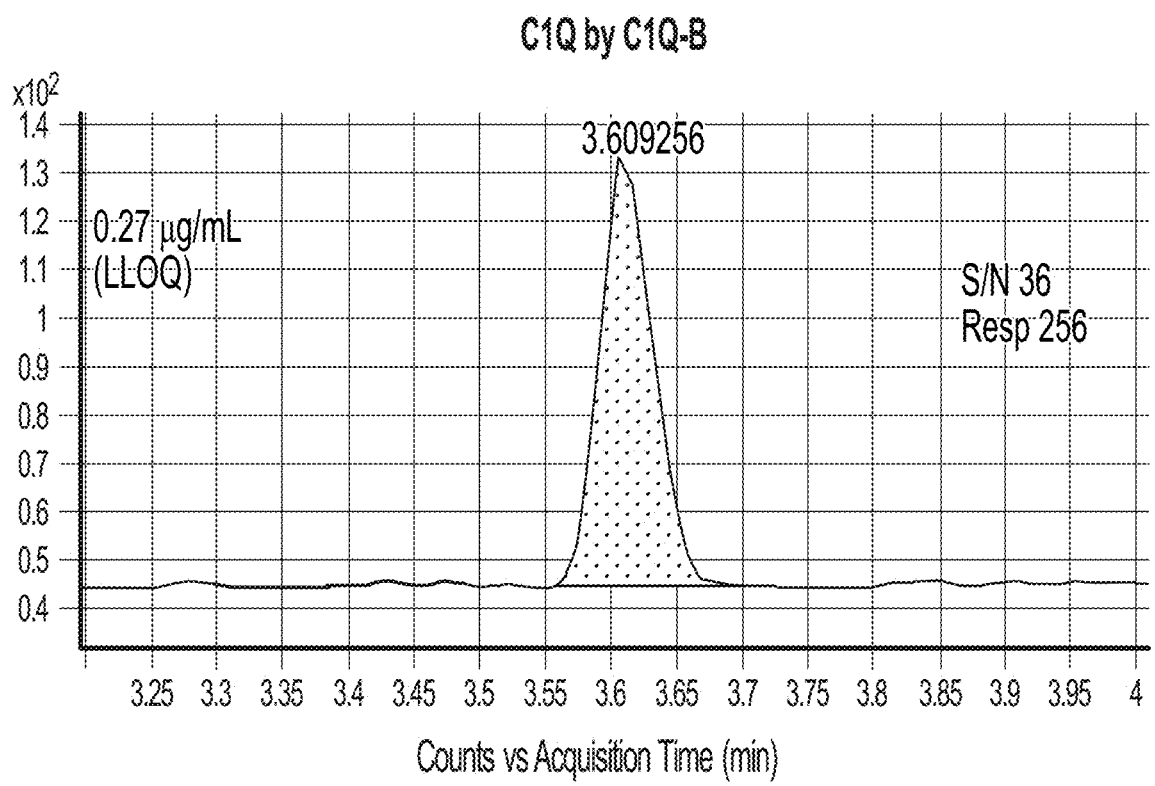
Figure 8C:
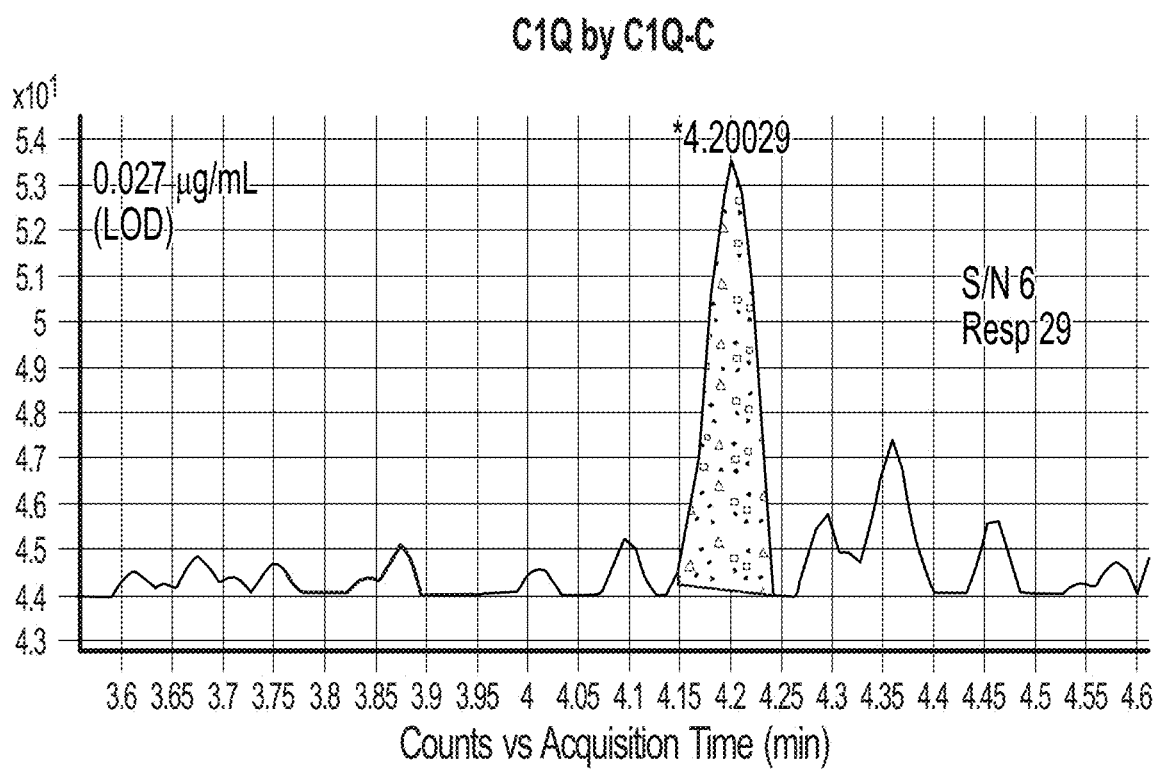
Figure 8C:
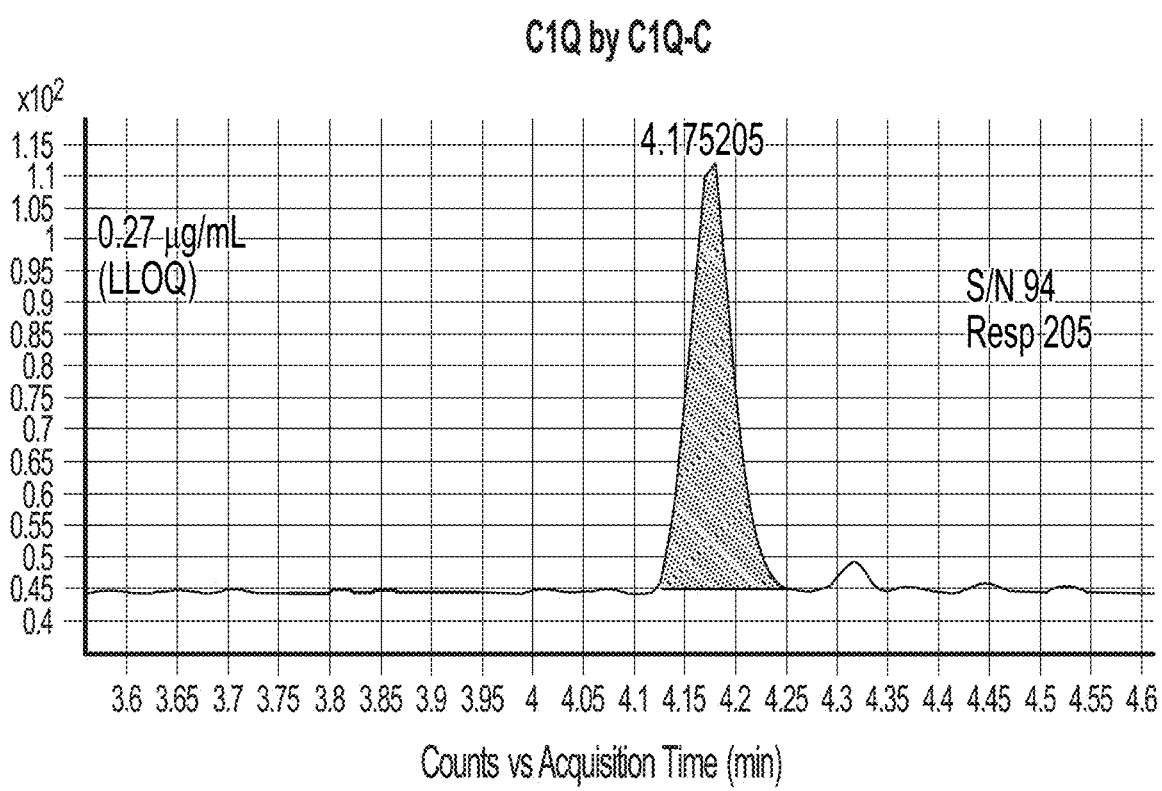
Figure 9A:
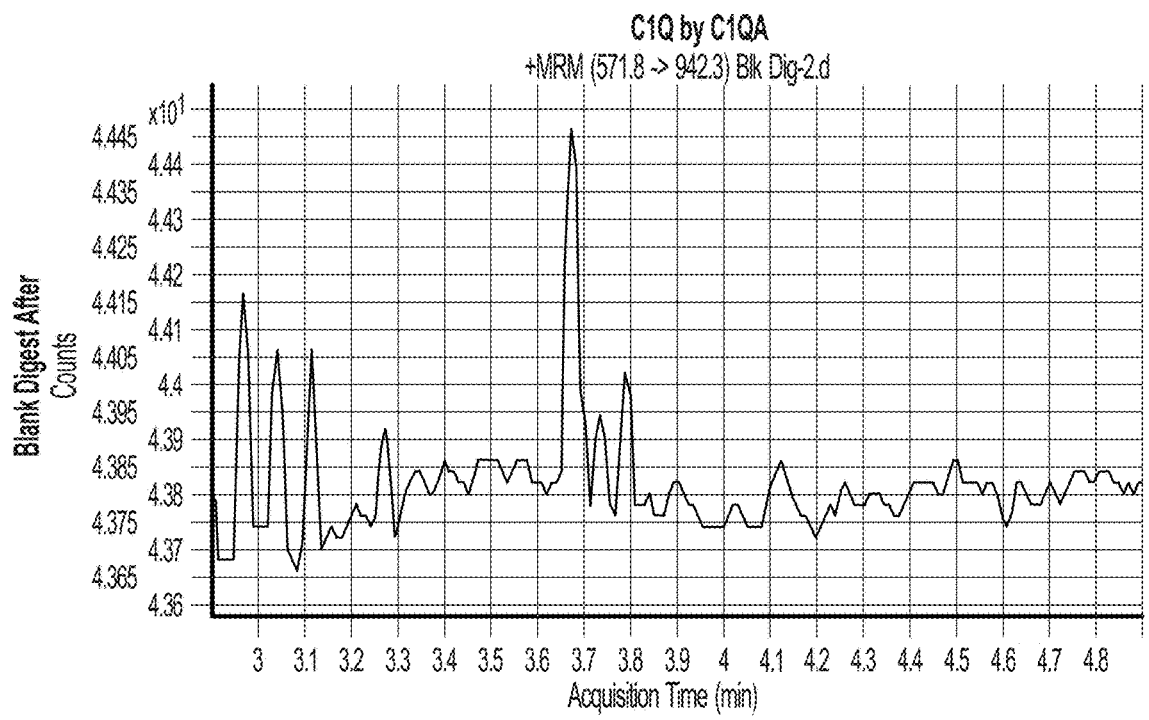
FIG. 9A, FIG. 9B, FIG. 9C, FIG. 9D and FIG. 9E are a series of LC-SRM-MS/MS chromatograms of selected peptides derived from the A, B, and C subunits of C1q in blank digest samples before and after analyzing a ULOQ sample.
Figure 9A:
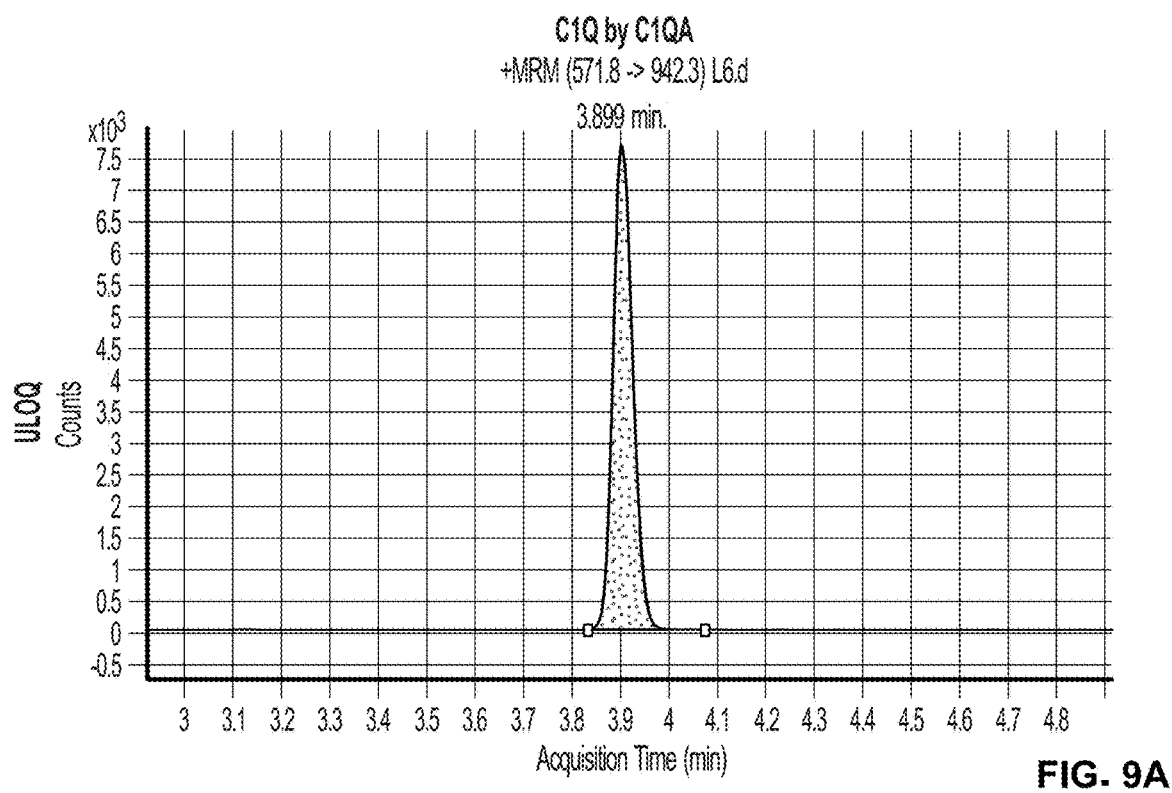
Figure 9B:
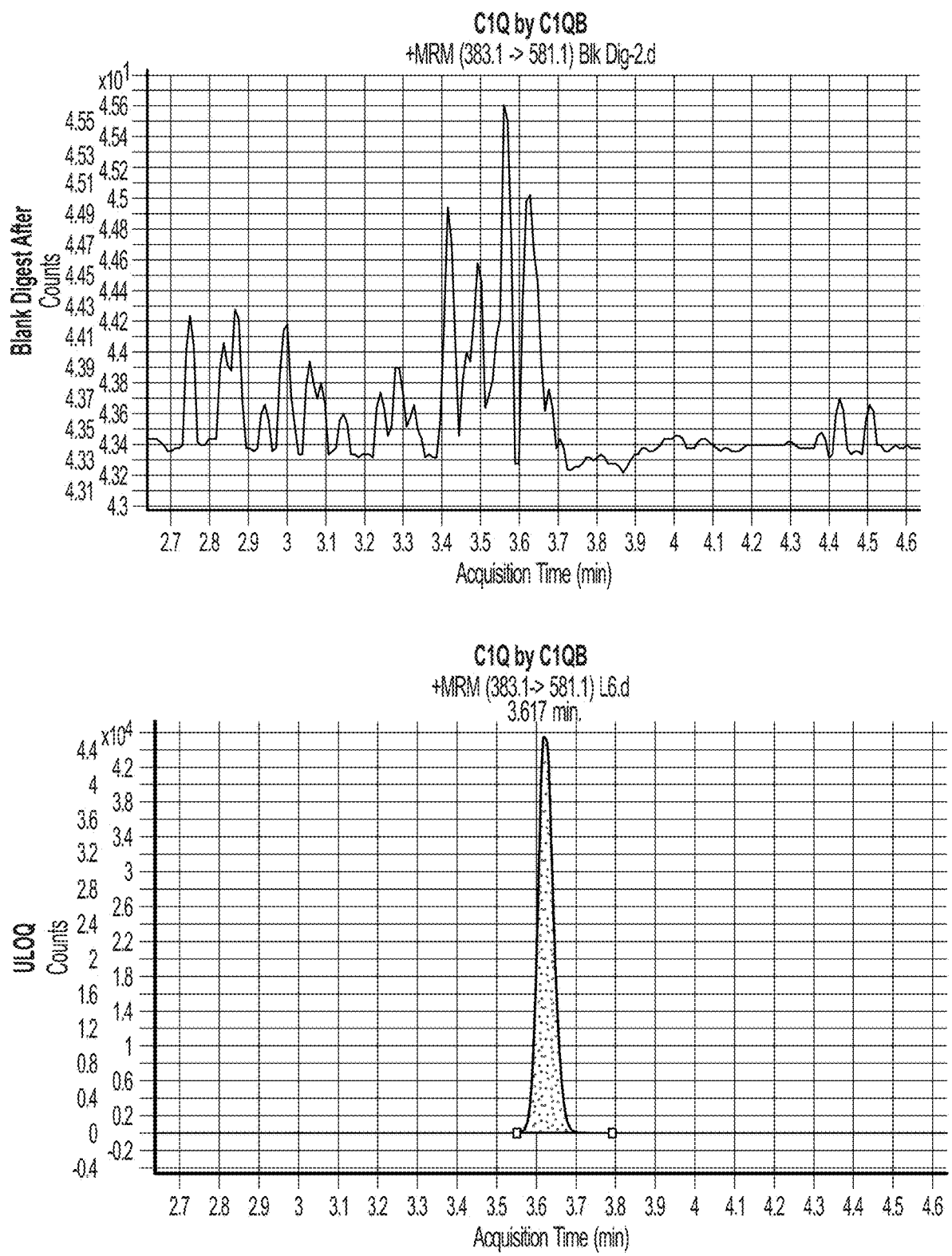
Figure 9C:
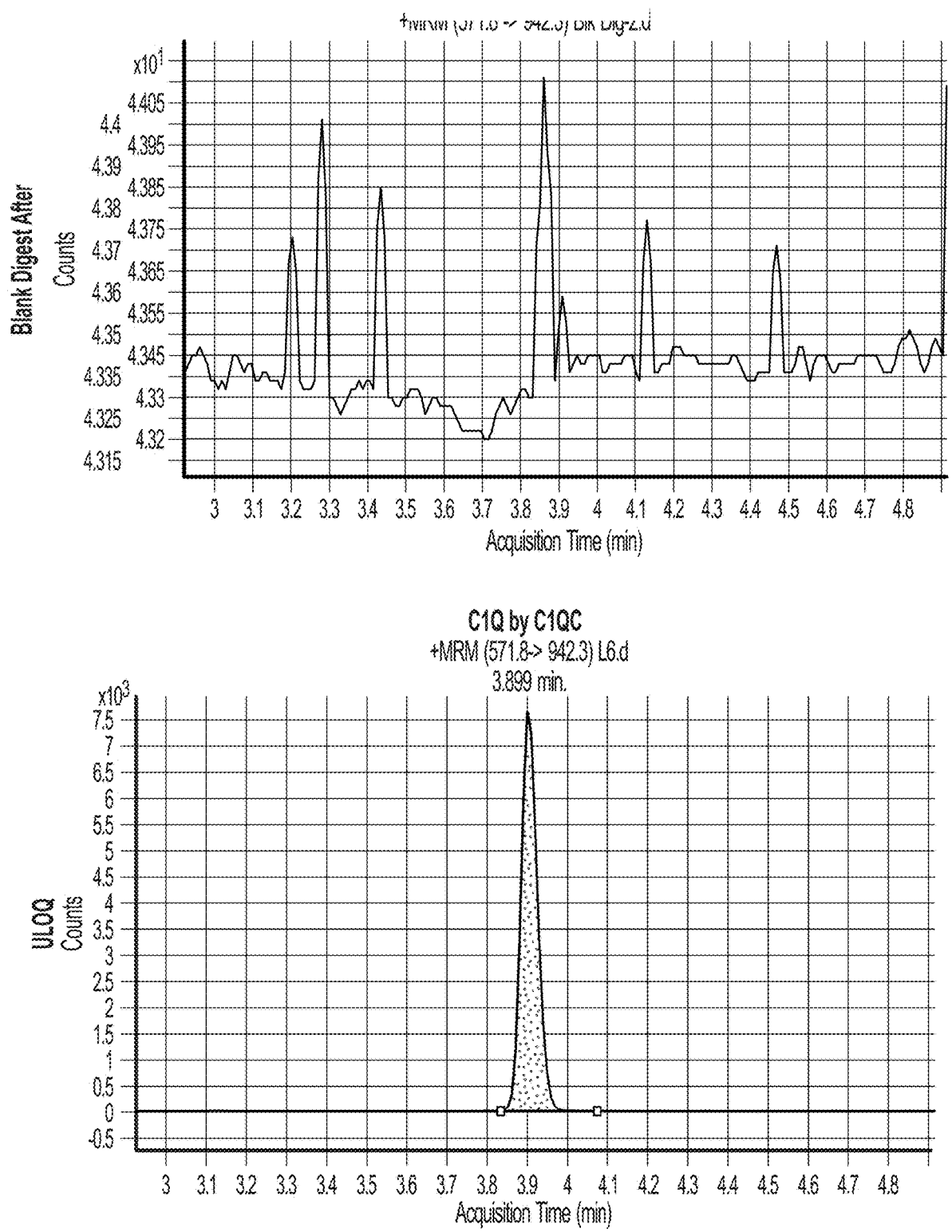
Figure 9D:
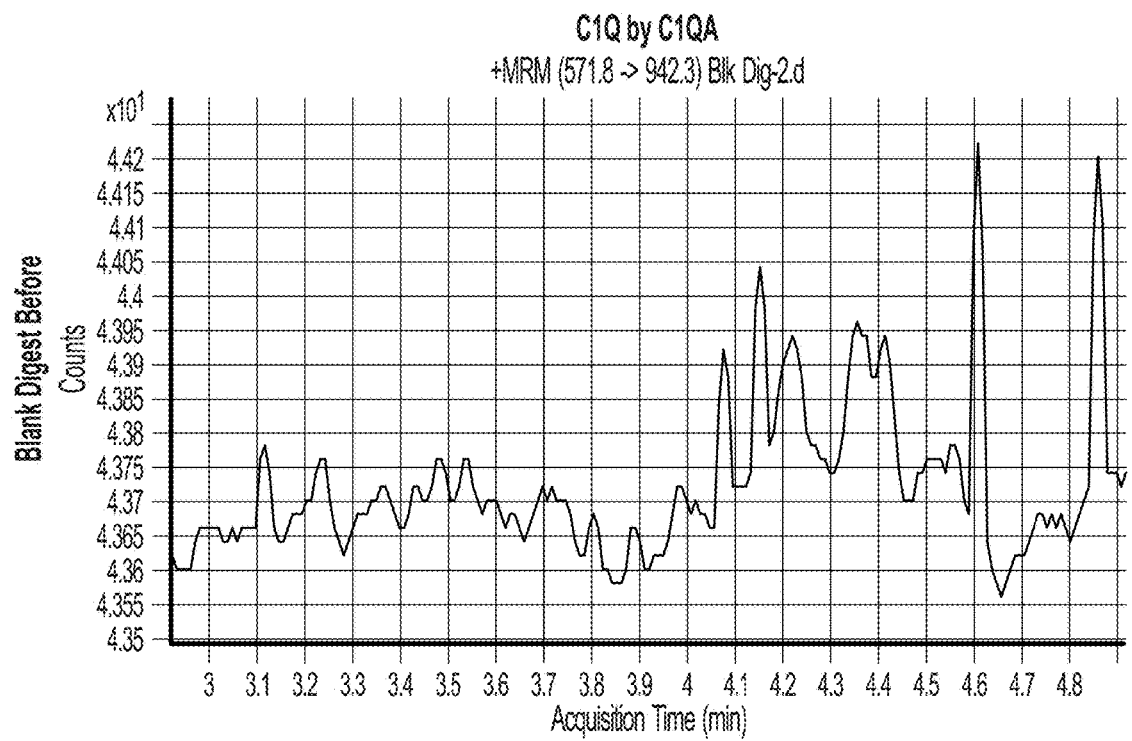
Figure 9D:
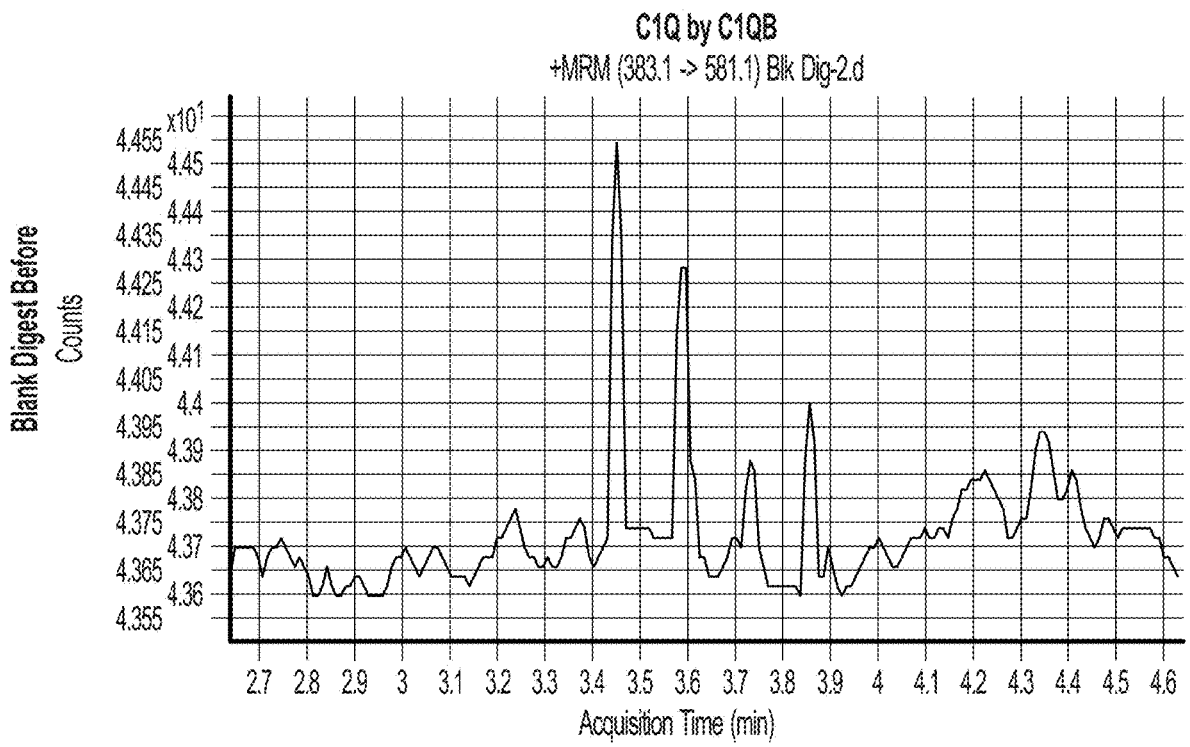
Figure 9E:
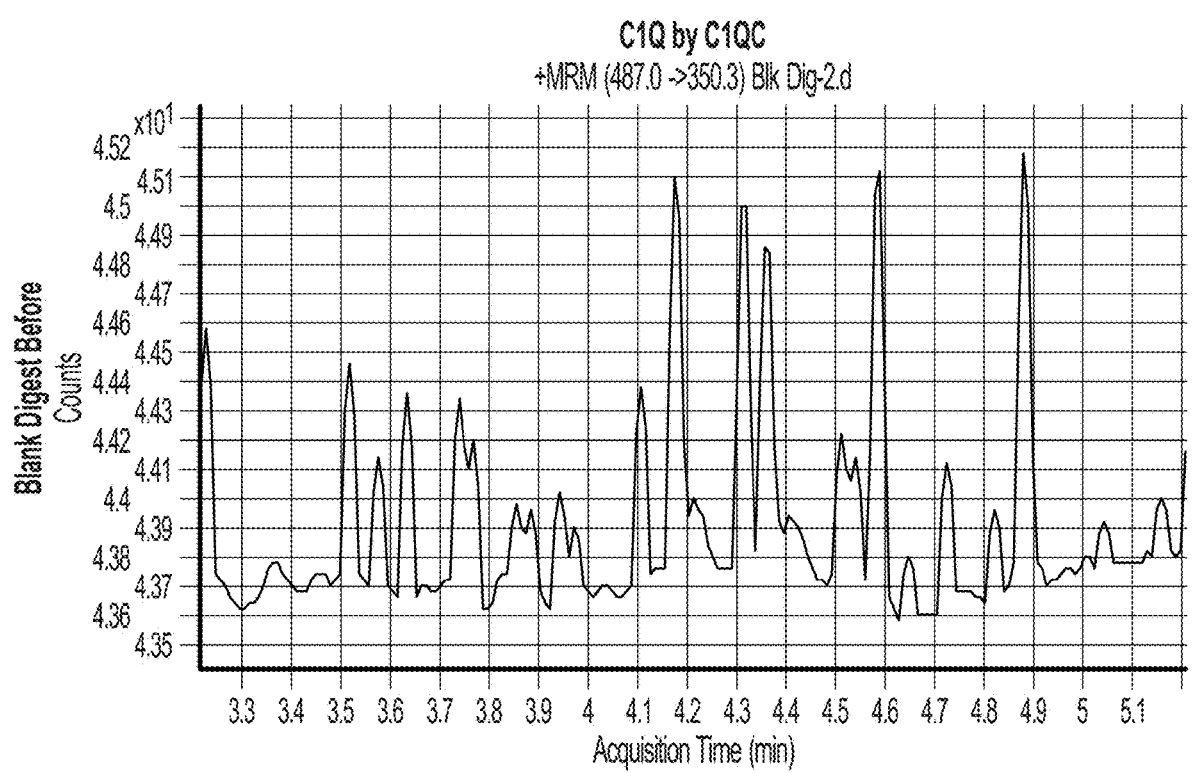
Figure 10A:
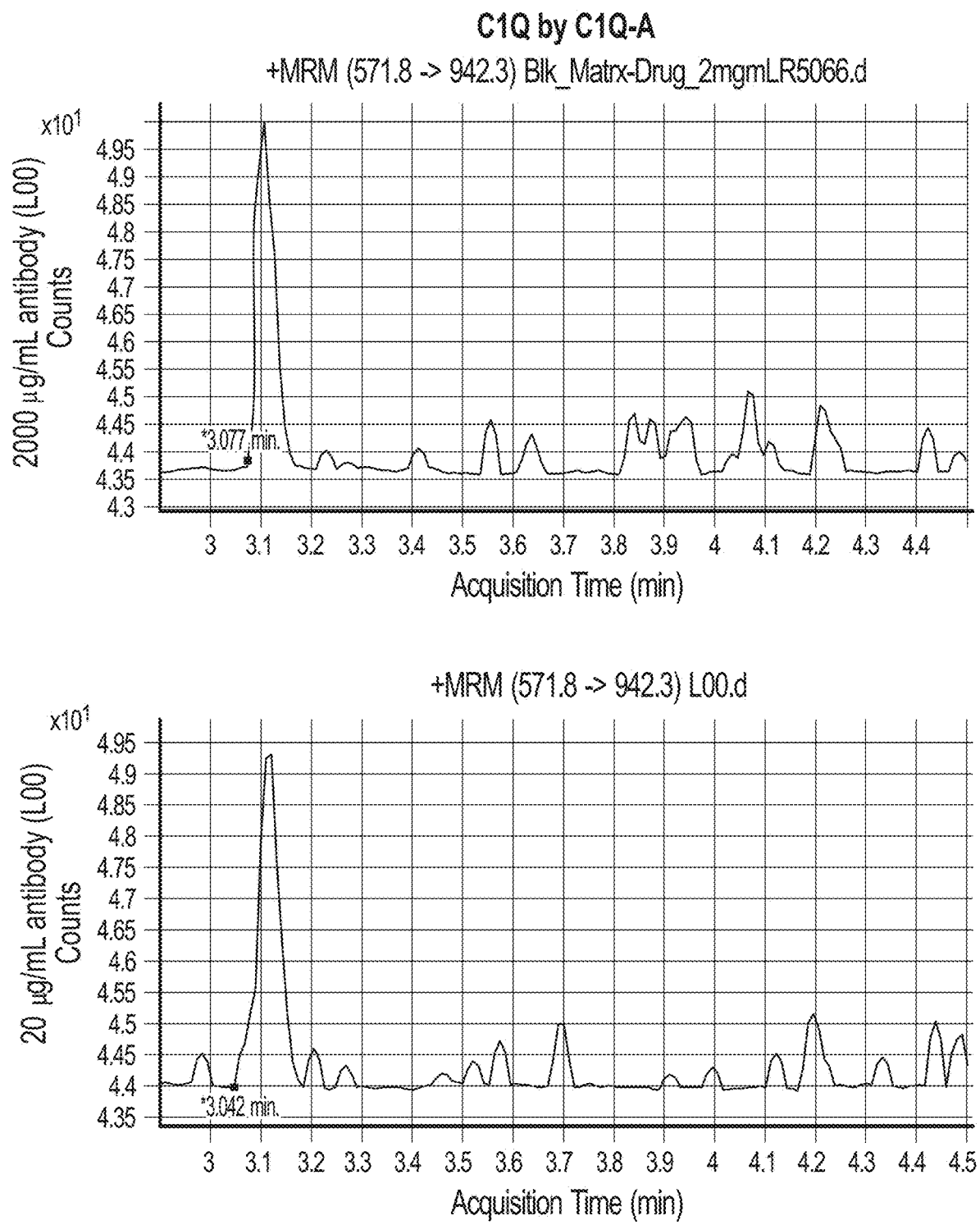
FIG. 10A, FIG. 10B, FIG. 10C, FIG. 10D, FIG. 10E and FIG. 10F show the LC-SRM-MS/MS chromatograms of selected peptides derived from the A, B, and C subunits of C1q in Double Blank (L00) standard solutions supplemented with 2000 µg/mL bispecific antibody, 20 µg/mL bispecific antibody or no bispecific antibody, and a LLOQ sample.
Figure 10B:
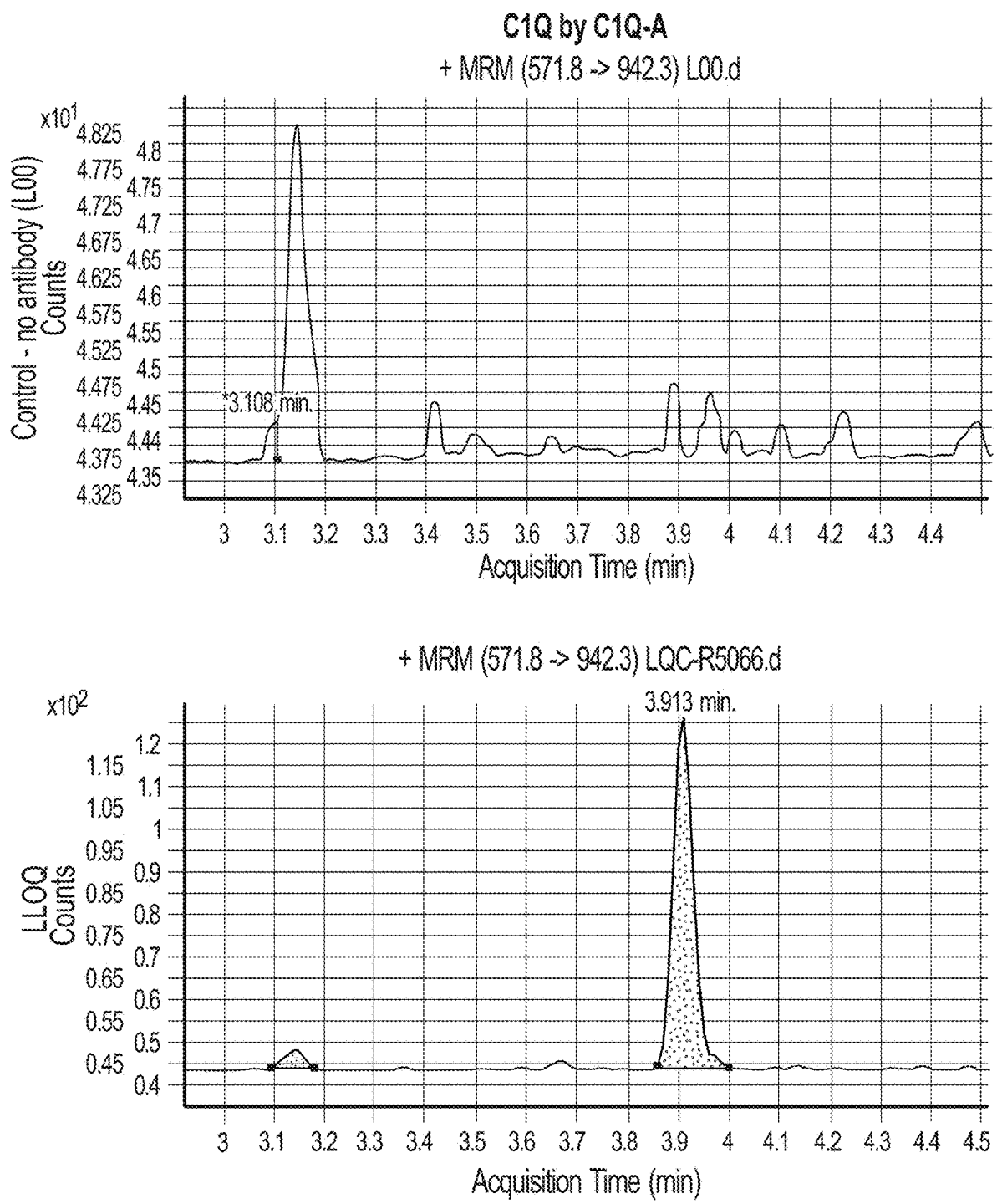
Figure 10C:
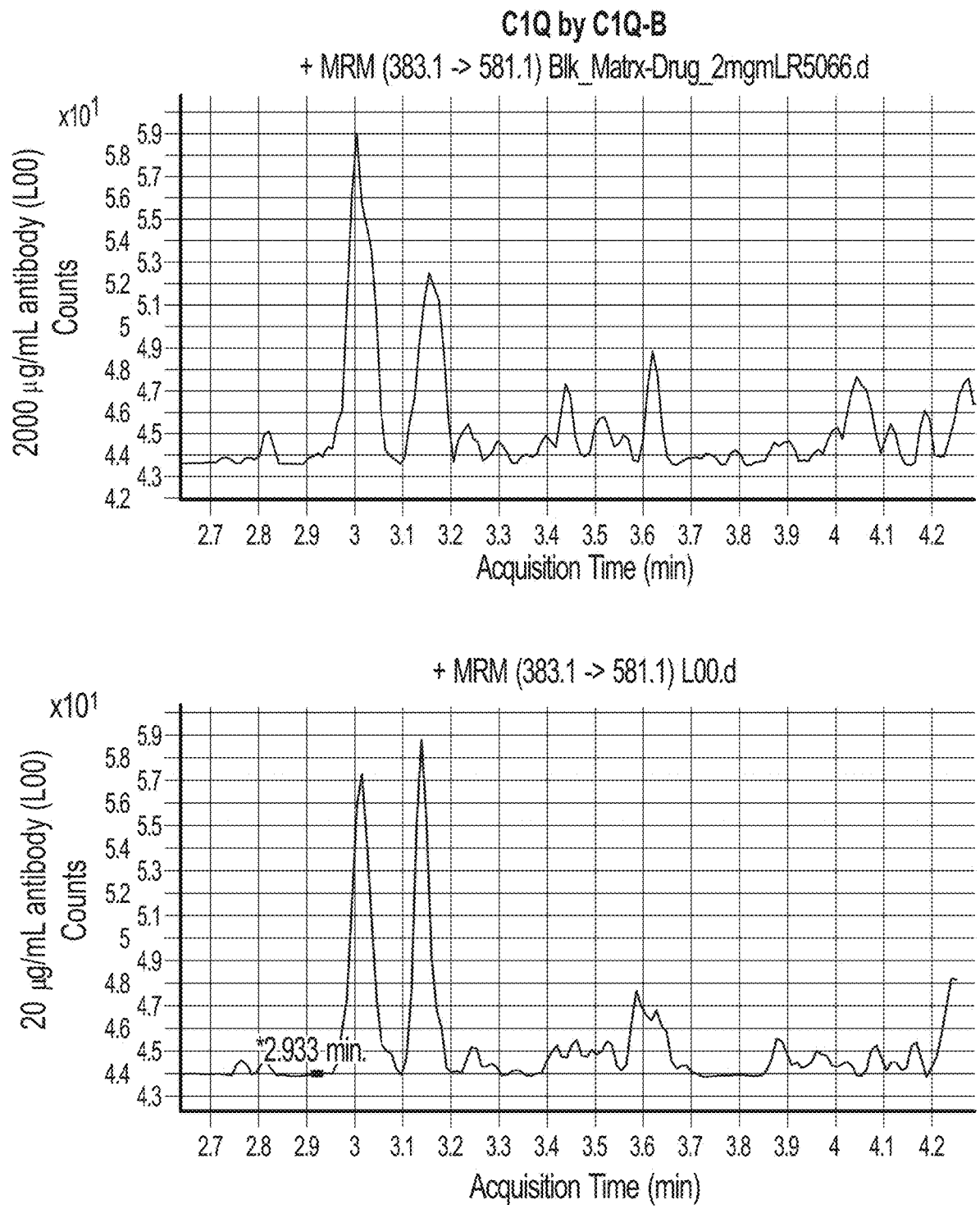
Figure 10D:
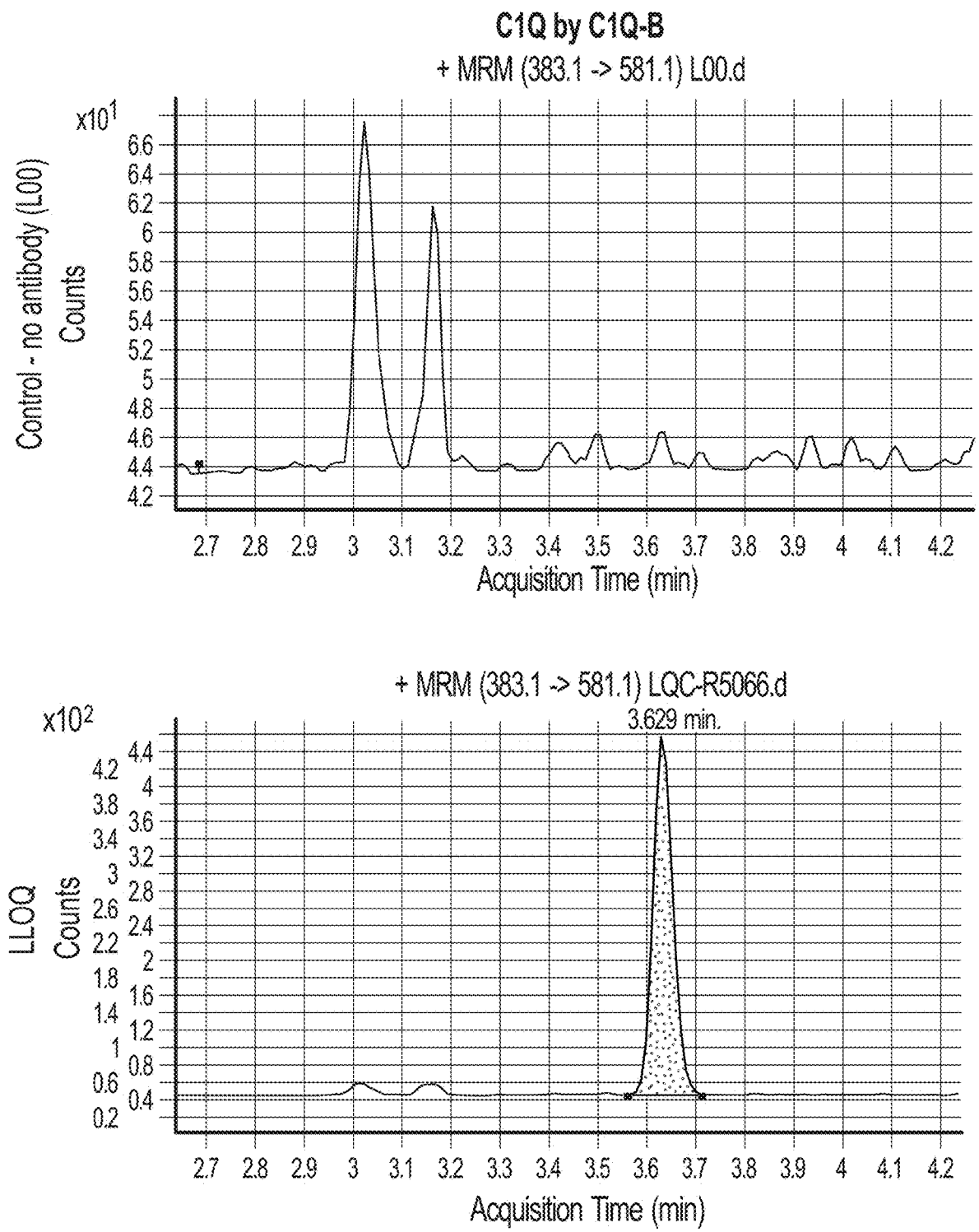
Figure 10E:
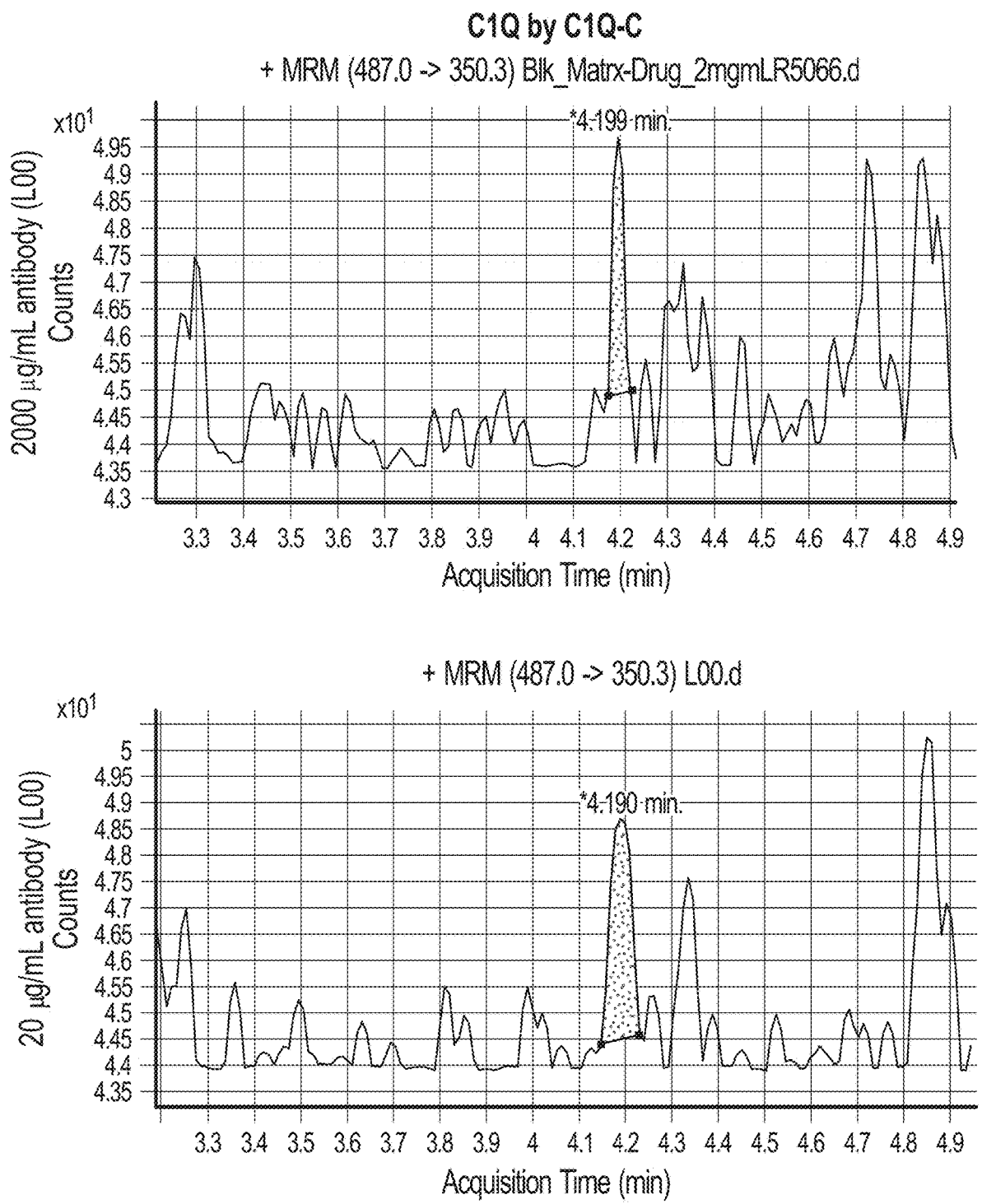
Figure 10F:
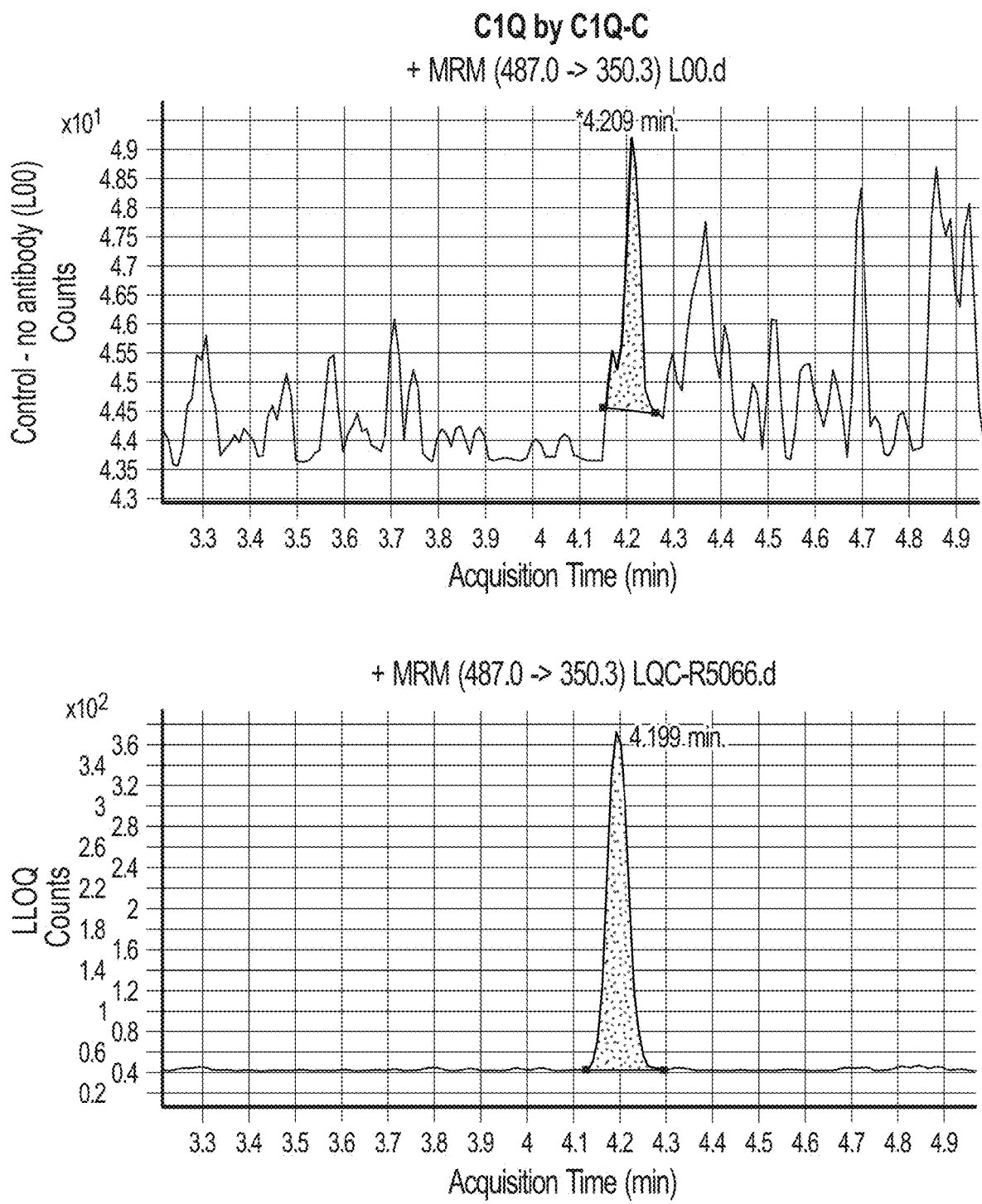

As shown in FIGS. 7A-7F, mass chromatogram recorded at the LLOQ concentration (0.27 µg/mL) for the subunit A peptide and the subunit B peptide exhibited little to no background peaks located at the same acquisition time as the peptide peaks in the blank and double blank samples. However, as show in FIGS. 7A-7F, the mass chromatogram recorded for the subunit C peptide exhibited background peaks in the blank and double blank samples. The area under curve for the background peak in the blank sample was approximately 5% of the area under curve for the sample peak. Overall, as shown in FIGS. 8A-8C, the signal to noise ratios for the subunit A peptide, the subunit B peptide and the subunit C peptide at the LLOQ concentration were 51, 36, 94, respectively and at the Limited of Detection (LOD) concentration were 7, 9 and 6 respectively.

Example 2—Testing Instrument Carryover of the Methods of the Present Disclosure As the methods of the present disclosure may be used to perform consecutive experiments on the same instrument, it is important to make sure that the carryover from the last sample will not interfere with the assay for the next sample. The instrument carryover during the practice of the methods of the present disclosure was measured.

An LC-SRM-MS chromatogram was first recorded for a blank digest sample. Immediately after, a mass chromatogram for a C1q QC sample at the ULOQ concentration (66.7 µg/mL) was recorded on the same instrument. Finally, a second blank digest sample was analyzed on the same instrument after the analysis of the ULOQ sample. As shown in FIGS. 9A-9E, there was no significant change in the blank digest chromatograms before or after analyzing the ULOQ sample for the subunit A, subunit B or subunit C peptide. These results demonstrate that the instrument carryover for the methods of the present disclosure is minimal.

Example 3—Testing Drug Tolerance of the Methods of the Present Disclosure

To examine whether or not the presence of antibody drugs interferes with the methods of the present disclosure, different concentrations (0, 20 µg/mL, or 2000 µg/mL) of a bispecific antibody were added to C1q reference samples at the Double Blank (blank matrix only, without internal standard; L00) concentration. As shown in FIGS. 10A-10F, the addition of the bispecific antibody did not produce any significant changes in the recorded mass chromatogram.

Figure 11:
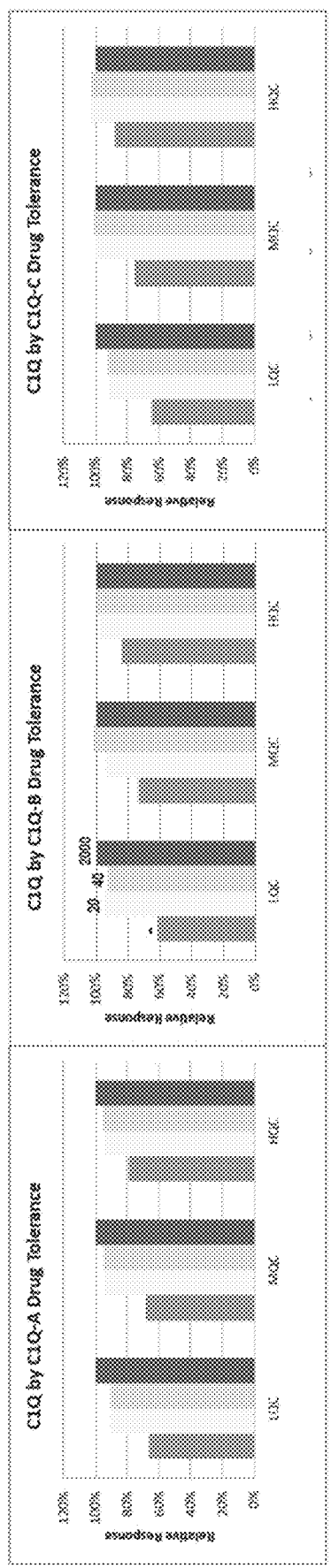
FIG. 11 is a series of charts showing the relative response of C1q in samples incubated with bispecific antibody measured using the methods of the present disclosure.

C1q reference samples at the LQC, MQC and HQC concentrations (0.8 g/mL, 6.3 µg/mL and 50.0 µg/mL respectively) were incubated in the absence of the bispecific antibody or with either 0 µg/mL, 20 µg/mL, 40 µg/mL, or 2000 µg/mL of the bispecific antibody and analyzed using LC-SRM-MS/MS. These concentrations of the bispecific antibody in the C1q assay corresponded to 1 mg/mL, 2 mg/mL, or 100 mg/mL of the bispecific antibody in neat serum. To put these concentrations in the context of pharmacokinetics, when administered at the dosage of 50 mg/kg, the peak serum concentration ($C_{max}$) of the bispecific antibody 6 is 1.25-1.5 mg/mL. As shown in FIG. 11, the addition of the bispecific antibody actually improves the recovery of signal for the subunit A, subunit B and subunit C peptides. In FIG. 11, the pink or first bar in each group corresponds to samples incubated in the absence of the bispecific antibody; the yellow or second bar in each group corresponds to samples incubated with 20 µg/mL of the bispecific antibody; the green or third bar in each group corresponds to samples incubated with 40 µg/mL of the bispecific antibody; the blue or fourth bar in each group corresponds to samples incubated with 2000 µg/mL of the bispecific antibody.

Figure 12:
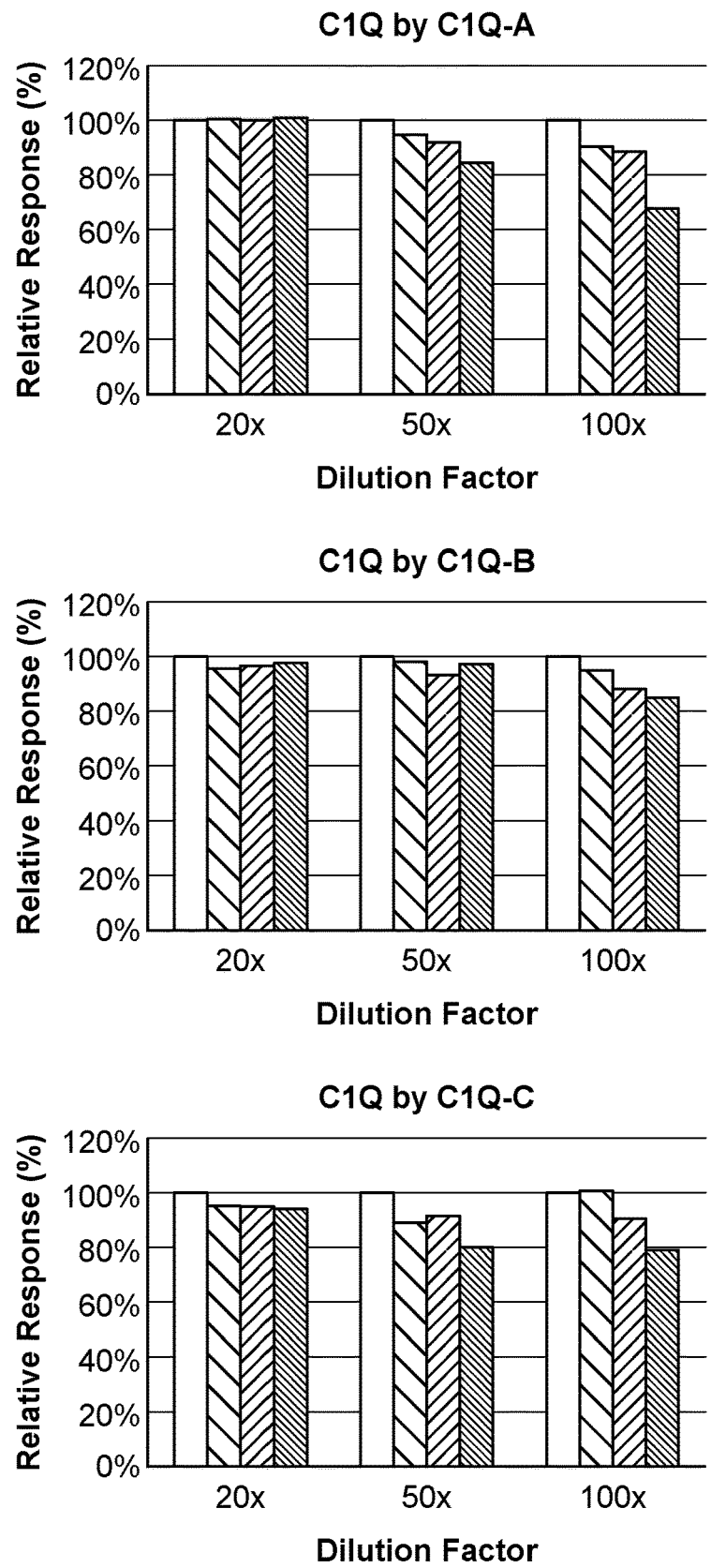
FIG. 12 is a series of charts showing the relative response measured for endogenous C1q in samples diluted at different dilution factors in different diluents using the methods of the present disclosure.

Example 4—Testing Dilution Recovery and Dilution Linearity of the Methods of the Present Disclosure The recovery of endogenous C1q signal in the methods of the present disclosure was also tested in samples diluted in different diluents and with different dilution factors. The diluents tested included 2% depleted human serum incubated with 20 µg/mL of the bispecific antibody, 2% depleted human serum, 0.1% BSA and a Tris-HCl solution. These samples were diluted 20×, 50× and 100× and LC-SRM-MS/MS was used to analyze the dilutions. As shown in FIG. 12, the addition of the bispecific antibody improves the recovery of the subunit A, subunit B and subunit C peptide signals even at higher dilution factors. There was a lower signal recovery in samples diluted with 0.1% BSA and Tris-HCl. In FIG. 12, the blue or first bar in each group corresponds to samples diluted with 2% depleted human serum incubated with 20 µg/mL of the bispecific antibody; the orange or second bar in each group corresponds to samples diluted with 2% depleted human serum; the green or third bar in each group corresponds to samples diluted with 0.1% BSA; the purple or fourth bar in each group corresponds to samples diluted with Tris-HCl.

Figure 13:
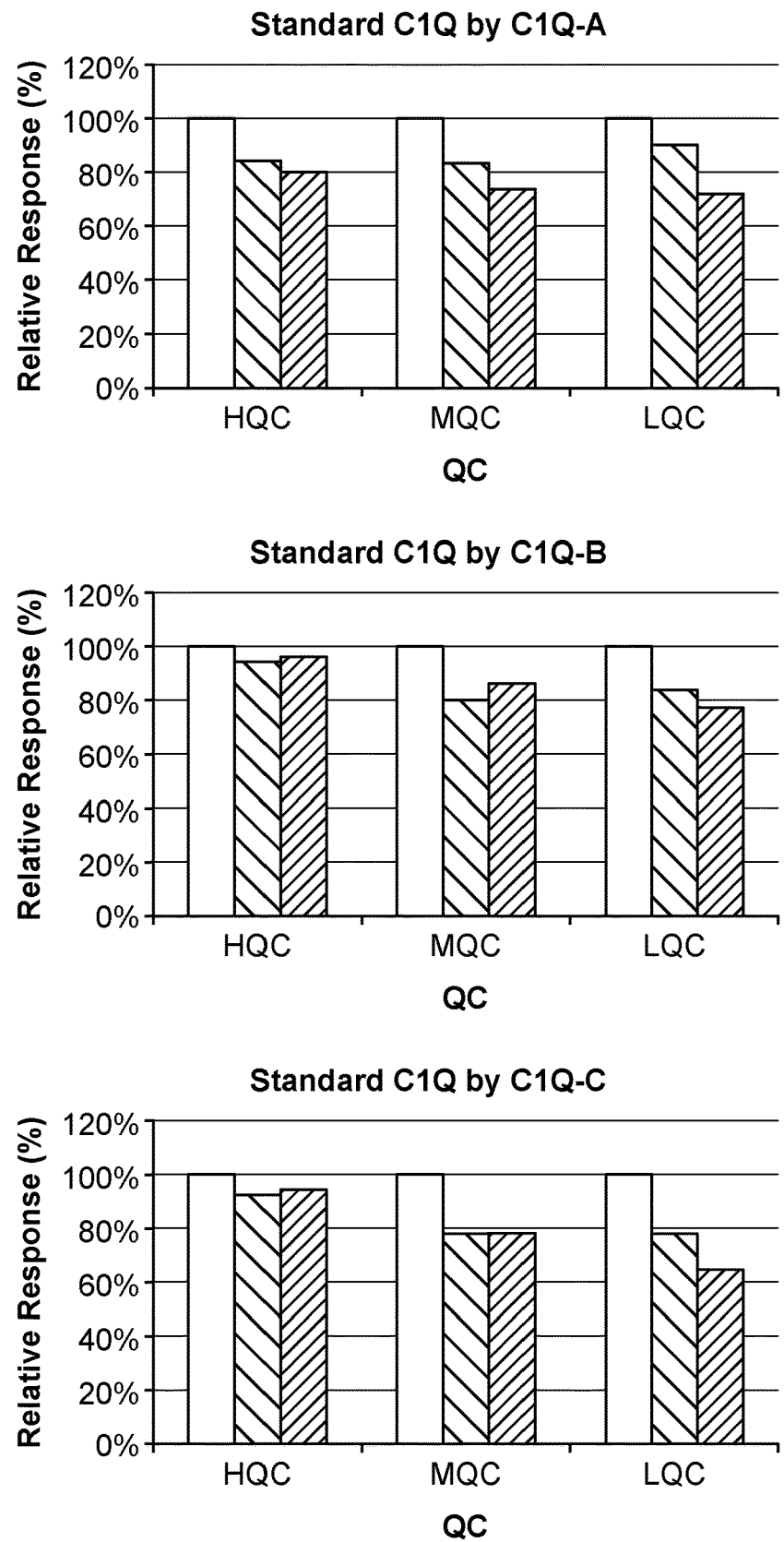
FIG. 13 is a series of charts showing the relative response measured for C1q in samples diluted at different dilution factors in different diluents using the methods of the present disclosure.

The recovery of signal from C1q reference standards using different diluents was also tested. C1q reference samples at LQC, MQC and HQC concentrations (0.8 µg/mL, 6.3 µg/mL and 50.0 µg/mL respectively) were diluted with either 2% depleted human serum incubated with 20 µg/mL of the bispecific antibody, 2% depleted human serum or 0.1% BSA. As shown in FIG. 13, the bispecific antibody improved the recovery of the subunit A, subunit B and subunit C peptide signals. In FIG. 13, the blue or first bar in each group corresponds to samples diluted with 2% depleted human serum incubated with 20 µg/mL of the bispecific antibody; the orange or second bar in each group corresponds to samples diluted with 2% depleted human serum; the green or third bar in each group corresponds to samples diluted with 0.1% BSA.

To test the dilution linearity of the methods of the present disclosure, pooled human serum, male monkey, and female monkey samples were diluted by 20 times, 50 times, and 100 times. The concentrations of endogenous C1q in these diluted samples were determined using the methods of the present disclosure. The results of this test are shown in Table 9 below.

TABLE 9

Dilution linearity test with endogenous C1q.

| Sample | Dilution Factor | By C1Q-A | | By C1Q-B | | By C1Q-C | |
| --- | --- | --- | --- | --- | --- | --- | --- |
| | | Cal. Conc. (ug/mL) | % RSD | Cal. Conc. (ug/mL) | % RSD | Cal. Conc. (ug/mL) | % RSD |
| Pooled Human Serum | 100X | 89 | | 80 | | 78 | |
| | 50X | 70 | 12.4% | 72 | 5.3% | 70 | 6.0% |
| | 20X | 87 | | 74 | | 74 | |
| Male Monkey | 100X | 87 | 8.7% | 59 | 0.8% | 61 | 2.7% |
| | 50X | 81 | | 58 | | 60 | |
| | 20X | 96 | | 58 | | 58 | |
| Female Monkey | 100X | 70 | | 56 | | 55 | 8.7% |
| | 50X | 67 | 2.1% | 49 | 6.2% | 50 | |
| | 20X | 69 | | 54 | | 59 | |

Example 5—Sample Preparation Repeatability and Sample Stability in Methods of the Present Disclosure Sample preparation repeatability of the methods of the present disclosure were tested using C1q QC samples at LLOQ, LQC, MQC, HQC, and ULOQ concentrations. For injection repeatability, aliquots of same QC sample were injected into the assay instrument either on same day (intra-day) or on different days (inter-day). For sample preparation repeatability, samples were prepared from QC solutions either on same day (intra-day) or on different days (inter-day). 3 samples for each condition were tested, and the relative standard deviation of the 3 samples for each condition is shown in Table 10 below.

TABLE 10

Injection and sample preparation repeatability of the methods of the present disclosure

| | | % RSD | | | |
|---|---|---|---|---|---|
| C1Q | QC (n = 3) | Intra-day Injector | Inter-day Injector | Intra-day Sample Prep | Inter-day Sample Prep |
| C1Q-A | LLOQ | 0.6 | 10.2 | 3.0 | 14.0 |
| | LQC | 7.8 | 7.1 | 9.2 | 13.7 |
| | MQC | 1.2 | 5.4 | 2.7 | 4.3 |
| | HQC | 1.2 | 1.3 | 0.9 | 1.3 |
| | ULOQ | 2.5 | 2.0 | 2.0 | 2.0 |
| C1Q-B | LLOQ | 4.8 | 5.0 | 0.8 | 6.0 |
| | LQC | 4.4 | 9.3 | 2.0 | 4.6 |
| | MQC | 1.8 | 6.2 | 1.5 | 3.9 |
| | HQC | 0.5 | 2.0 | 1.2 | 1.8 |
| | ULOQ | 0.4 | 0.8 | 1.2 | 1.7 |
| C1Q-C | LLOQ | 6.8 | 6.2 | 4.6 | 5.6 |
| | LQC | 1.3 | 1.6 | 3.3 | 5.6 |
| | MQC | 2.3 | 2.0 | 3.2 | 2.9 |
| | HQC | 1.3 | 2.2 | 1.6 | 2.5 |
| | ULOQ | 1.0 | 1.9 | 1.9 | 2.7 |

Figure 14:
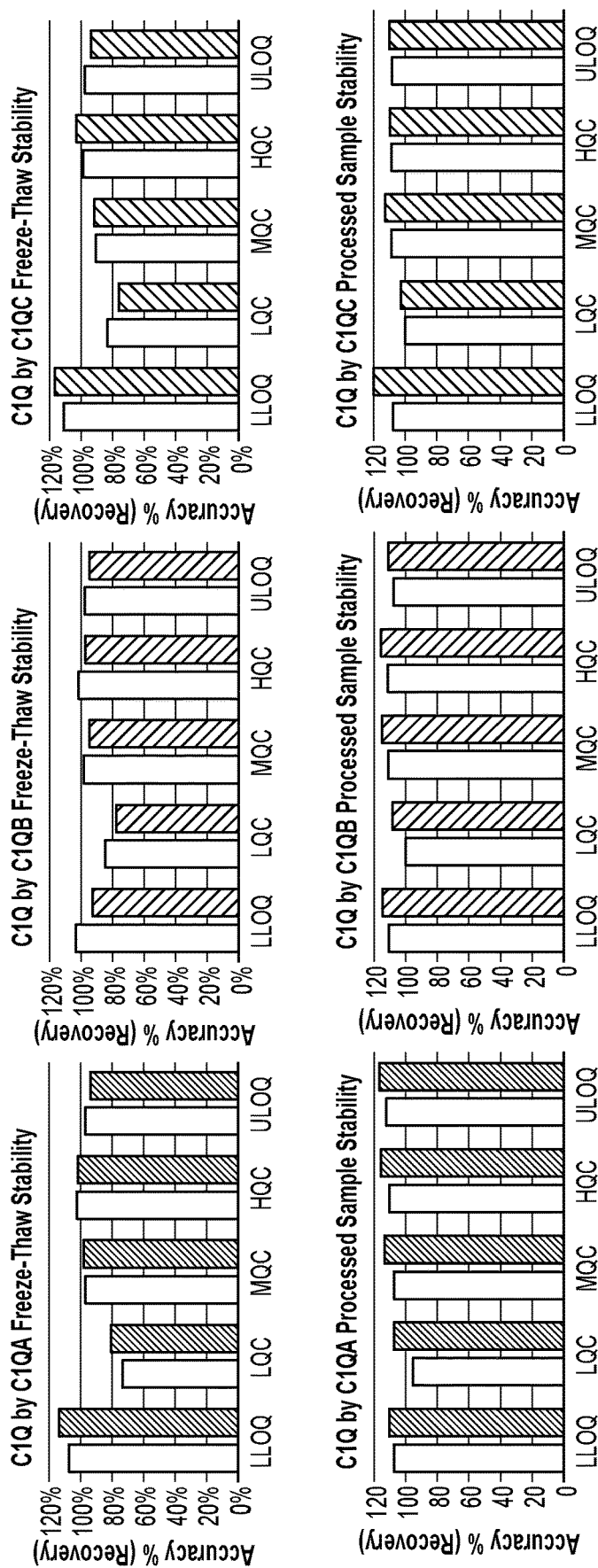
FIG. 14 is a series of charts showing the accuracy of measured concentration for C1q in samples subjected to three freeze thaw cycles or stored in an autosampler for 48 hours using the methods of the present disclosure.

For sample stability, C1q QC samples at LLOQ, LQC, MQC, HQC, and ULOQ concentrations (0.3 µg/mL, 0.8 µg/mL, 6.3 µg/mL, 50.0 g/mL, and 66.7 µg/mL respectively) were either subjected to three freeze thaw cycles, or stored in an autosampler for 48 hours before their C1q concentrations were determined by the C1q assay. As shown FIG. 14, the accuracy of the methods of the present disclosure were not significantly affected by three freeze thaw cycles, or by 48 hours storage in an autosampler. In the top row of charts in FIG. 14, the first bar in each group corresponds to samples that were freshly analyzed before freezing; the second bar in each group corresponds to samples that were subjected to three freeze thaw cycles. In the bottom row of charts in FIG. 14, the first bar in each group corresponds to samples that were freshly analyzed; the second bar in each group corresponds to samples that were analyzed after 48 hours storage in an autosampler.

In separate experiments, 72 hours storage was also tested, and no sample degradation or loss was observed.

Example 6—Assay Variation Related to Internal Standard Peptides in Methods of the Present Disclosure Heavy isotope labelled peptides; called internal standard peptides (ISPs) have identical amino acid sequences as the subunit A, subunit B and subunit C peptides. C1q QC samples at LLOQ, LQC, MQC, HQC, and ULOQ concentrations (0.3 µg/mL, 0.8 µg/mL, 6.3 µg/mL, 50.0 µg/mL and 66.7 µg/mL respectively) were analyzed in the presence and absence of each ISP. The results of this analysis are shown in Table 11. The inclusion of the ISPs did not interfere with the analysis. Therefore, isotope labelled peptides used for retention time confirmation, instrument performance calibration, and troubleshooting purposes.

TABLE 11

C1q assay variation with or without isotope labelled internal standard peptides

| | % RSD of QC (n = 3) | | | | | |
|---|---|---|---|---|---|---|
| QC | C1QA | | C1QB | | C1QC | |
| (n = 3) | −ISP | +ISP | −ISP | +ISP | −ISP | +ISP |
| LLOQ | 8% | 12% | 4% | 2% | 2% | 8% |
| LQC | 11% | 11% | 4% | 2% | 2% | 1% |
| MQC | 2% | 6% | 3% | 5% | 2% | 4% |
| HQC | 2% | 6% | 1% | 4% | 0% | 8% |
| ULOQ | 2% | 3% | 1% | 1% | 2% | 7% |

Example 6—Quantitation of C1q in Blood Samples from Treated Monkeys Using the Methods of the Present Disclosure The methods of the present disclosure were used to quantify the concentration of C1q protein present in the blood samples of monkeys treated with a bispecific antibody. The monkey group designation and dose levels are shown in Table 12.

TABLE 12

Monkey group designation and dose levels

| Group | No. of animals (male) | Dose level (mg/kg) | Dose concentration (mg/mL) |
|---|---|---|---|
| 1 (Isotype control) | 3 | 50 | 25 |
| 2 (Low) | 3 | 2 | 1 |
| 3 (Mid) | 3 | 10 | 5 |
| 4 (High) | 3 | 50 | 25 |

Group 1 was administered diluted an isotype control antibody via slow bolus intravenous injection at a dose volume of 2 mL/kg. Groups 2, 3, and 4 were administered a diluted bispecific antibody via slow bolus intravenous injection at a dose of 2 mL/kg. 0.5 mL blood samples were collected according the following schedule: pre-dose sample and approximately 5 minutes after dose sample were collected on Day 1; subsequent samples were collected at 24 hours, 72 hours and 168 hours after dose; samples were also collected once on each of Day 14 after dose, Day 42 after dose and Day 56 after dose. Blood samples were centrifuged for 1 hours after collection, and the harvested serum samples were split into 4 aliquots, 50 µL each.

Each monkey serum sample was diluted by 50 times in 100 mM Tris-HCl, pH 7.5 and 20 µg/mL of the bispecific antibody. 5 µL of each diluted monkey serum sample was then denatured and reduced in 20 µL of 8 M urea and 10 mM tris(2-carboxyethyl) phosphine (TCEP) at 56° C. with shaking for 30 minutes. 5 µL of 50 mM iodoacetamide was then added to each sample, and the samples were then incubated in the dark at 25° C. with shaking for 30 minutes. 10 µL of the appropriate isotope-labelled internal standard peptide solution (see Example 1) was added before 100 µL of 0.01 µg/µL trypsin was added to each sample. The samples were then incubated at 37° C. in the dark with shaking for 4 hours. 5 µL of 20% of formic acid was added to the samples to quench the tryptic digestion reaction. The samples were mixed and centrifuged at 4680 rpm for 5 minutes before they were analyzed by LC-SRM-MS/MS.

For each monkey serum sample, LC-SRM-MS/MS was used to record the signal corresponding to the subunit A peptide, the subunit B peptide and the subunit C peptide, as well as the signals corresponding to the isotope-labelled internal standard peptides.

The concentrations of C1q in each of the dosed monkey serum samples were then determined by comparing the signals of the subunit A, subunit B and subunit C peptides to calibration curves (generated as described in Example 1)

Figure 15:
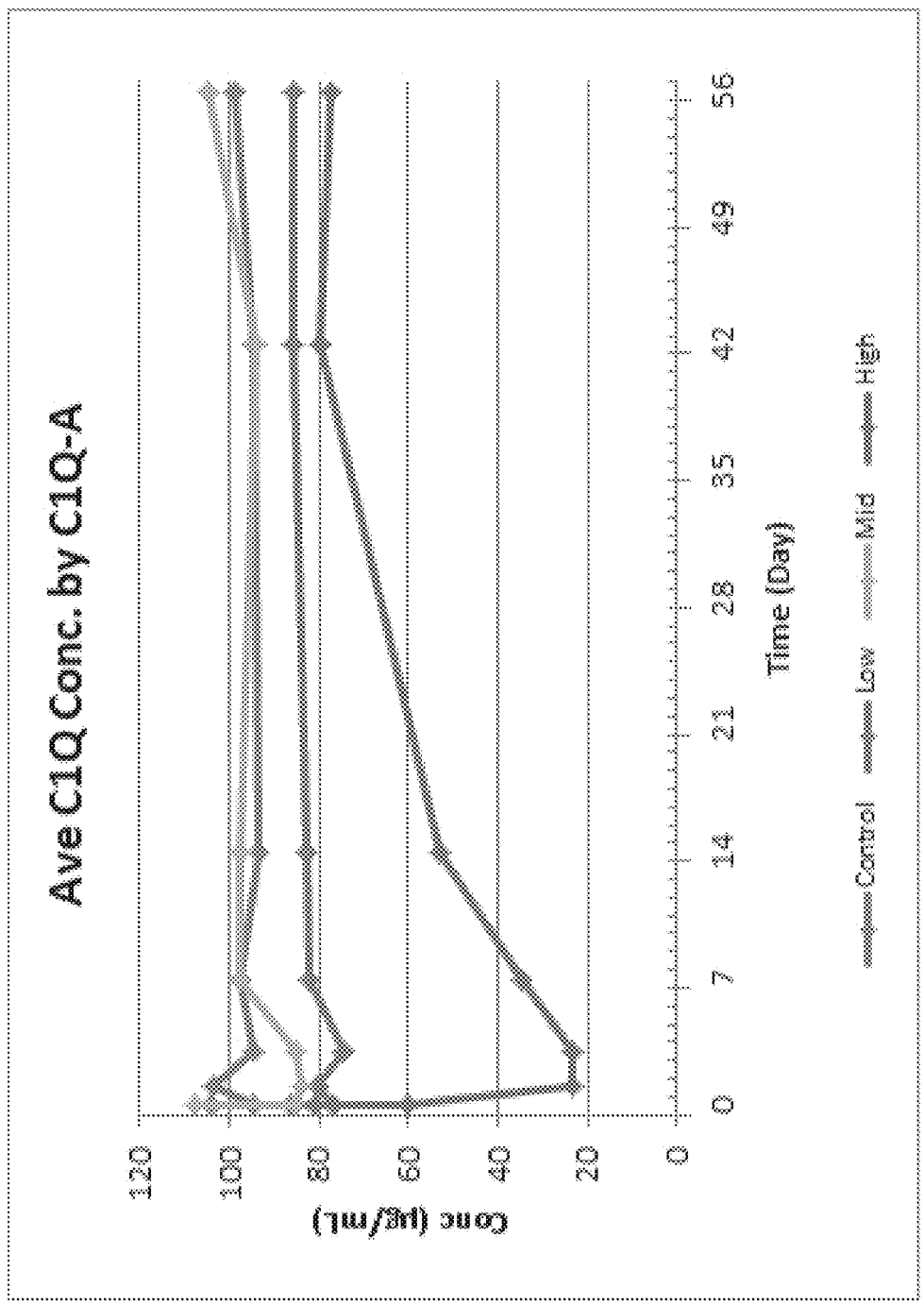
FIG. 15 shows a chart depicting the C1q concentration over time in the blood samples from dosed monkeys, determined using the methods of the present disclosure and a selected peptide derived from the A subunit of C1q.
Figure 16:
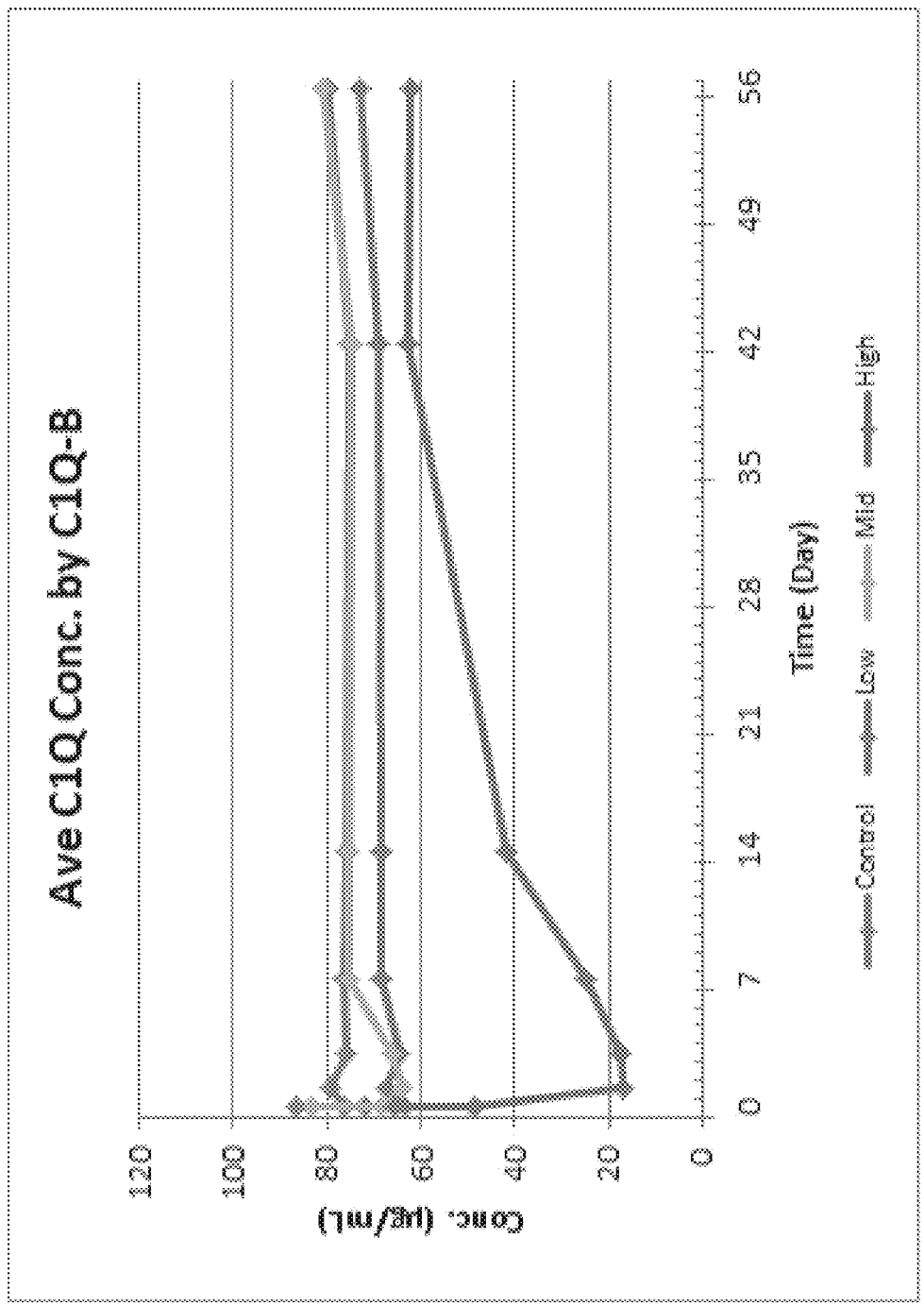
FIG. 16 shows a chart depicting the C1q concentration over time in the blood samples from dosed monkeys, determined using the methods of the present disclosure and a selected peptide derived from the B subunit of C1q.
Figure 17:
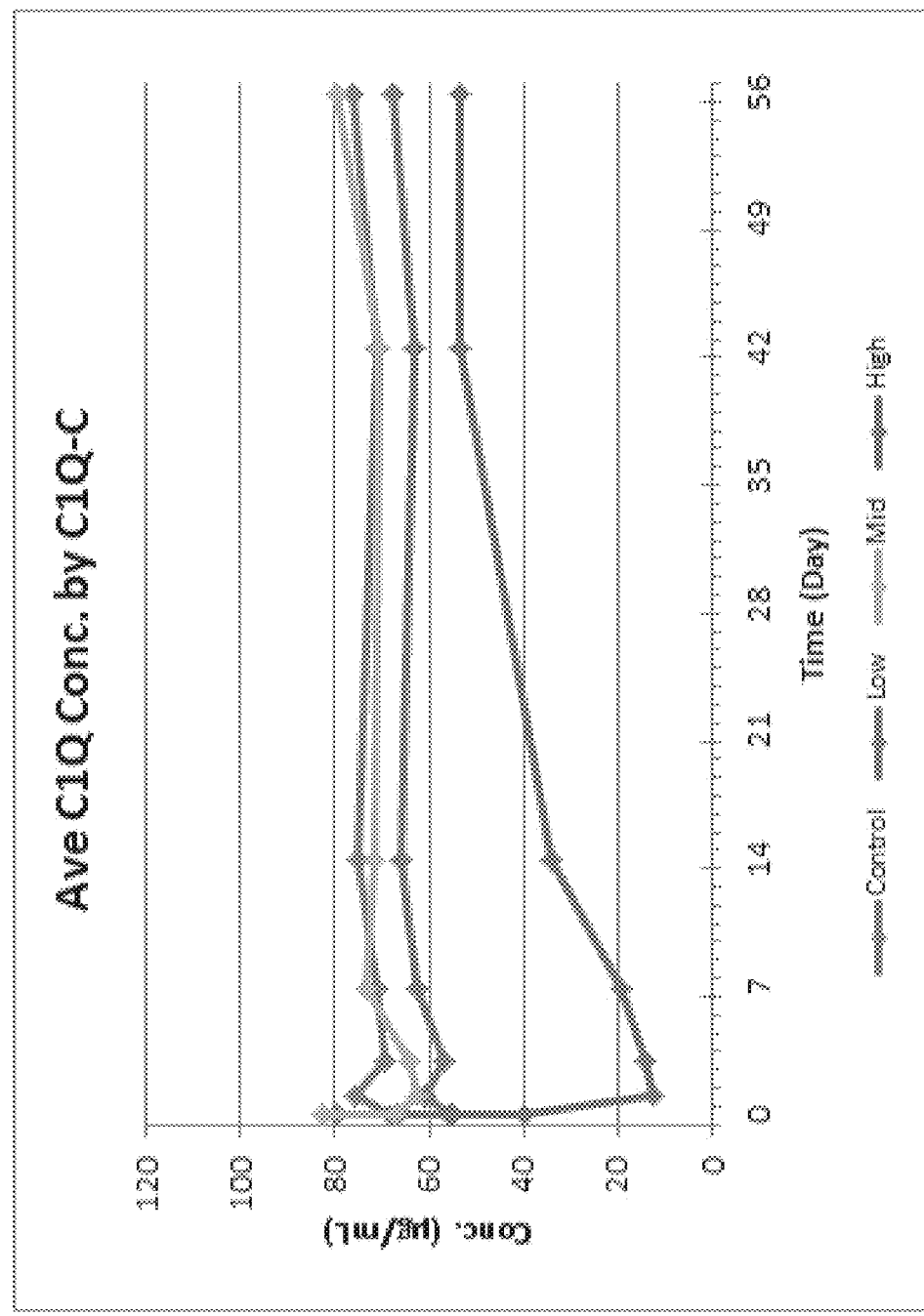
FIG. 17 shows a chart depicting the C1q concentration over time in the blood samples from dosed monkeys, determined using the methods of the present disclosure and a selected peptide derived from the C subunit of C1q.

The concentrations of C1q, as determined by the subunit A peptide, subunit B peptide and subunit C peptide, are shown in Tables 13-15. The post dose time course of C1q concentrations in monkey blood are depicted in FIGS. 15-17. FIG. 15 shows the concentration of C1q in the dose monkey samples quantified using the subunit A peptide. FIG. 16 shows the concentration of C1q in the dose monkey samples quantified using the subunit B peptide. FIG. 17 shows the concentration of C1q in the dose monkey samples quantified using the subunit C peptide. In FIG. 15-17, the blue line corresponds to monkeys in Group 1, the red line corresponds to monkeys in Group 2, the green line corresponds to monkeys in Group 3 and the purple line corresponds to monkeys in Group 4.

TABLE 13

Quantitation of dosed monkey blood samples for C1q concentration by target peptide SLGFCDTTNK (SEQ ID NO: 26) derived from C1q A subunit.

Concentration of C1q by Subunit A (µg/mL)

| Time Point | Group 1 (Isotype Control) | | | Group 2 (Low) | | | Group 3 (Mid) | | | Group 4 (High) | | |
|---|---|---|---|---|---|---|---|---|---|---|---|---|
| | P0001 | P0002 | P0003 | P0101 | P0102 | P0103 | P0201 | P0202 | P0203 | P0301 | P0302 | P0303 |
| Pre-dose | 124 | 87 | 102 | 89 | 93 | 76 | 114 | 120 | 90 | 59 | 92 | 92 |
| 5 min | 102 | 88 | 94 | 78 | 81 | 72 | 90 | 91 | 74 | 43 | 70 | 67 |
| 24 h | 118 | 83 | 108 | 78 | 89 | 74 | 84 | 102 | 66 | 4* | 58 | 9* |
| 72 h | 112 | 76 | 96 | 80 | 79 | 64 | 93 | 96 | 67 | 5* | 53 | 13* |
| 168 h | 116 | 80 | 96 | 81 | 86 | 79 | 106 | 106 | 81 | 8* | 67 | 28 |
| D14 | 105 | 77 | 99 | 78 | 100 | 70 | 120 | 93 | 79 | 25 | 71 | 63 |
| D42 | 106 | 81 | 96 | 74 | 103 | 80 | 85 | 106 | 91 | 56 | 83 | 99 |
| D56 | 109 | 91 | 96 | 79 | 104 | 74 | 105 | 117 | 92 | 53 | 86 | 94 |

*An estimated C1q concentration. Concentration below LLOQ (0.27 µg/mL) but above LOD (0.027 µg/mL).

TABLE 14

Quantitation of dosed monkey blood samples for C1q concentration by target peptide IAFSATR (SEQ ID NO: 29) derived from C1q B subunit.

Concentration of C1q by Subunit B (µg/mL)

| Time Point | Group 1 (Isotype Control) | | | Group 2 (Low) | | | Group 3 (Mid) | | | Group 4 (High) | | |
|---|---|---|---|---|---|---|---|---|---|---|---|---|
| | P0001 | P0002 | P0003 | P0101 | P0102 | P0103 | P0201 | P0202 | P0203 | P0301 | P0302 | P0303 |
| Pre-dose | 99 | 72 | 88 | 69 | 79 | 67 | 90 | 93 | 67 | 49 | 75 | 74 |
| 5 min | 82 | 67 | 80 | 61 | 69 | 59 | 71 | 77 | 58 | 34 | 58 | 55 |
| 24 h | 90 | 66 | 82 | 66 | 75 | 62 | 65 | 76 | 51 | 1* | 44 | 5* |
| 72 h | 90 | 63 | 75 | 59 | 75 | 59 | 72 | 73 | 53 | 2* | 44 | 7* |
| 168 h | 88 | 67 | 74 | 66 | 77 | 62 | 82 | 81 | 64 | 6* | 50 | 19 |
| D14 | 85 | 68 | 75 | 62 | 77 | 66 | 85 | 78 | 63 | 17 | 60 | 49 |
| D42 | 86 | 65 | 76 | 61 | 79 | 67 | 75 | 80 | 69 | 46 | 66 | 76 |
| D56 | 82 | 76 | 82 | 63 | 88 | 68 | 84 | 85 | 74 | 44 | 69 | 73 |

*An estimated C1q concentration. Concentration below LLOQ (0.27 µg/mL) but above LOD (0.027 µg/mL).

TABLE 15

Quantitation of dosed monkey blood samples for C1q concentration by target peptide QTHQPPAPNSLIR (SEQ ID NO: 36) derived from C1q C subunit.

Concentration of C1q by Subunit C (µg/mL)

| Time Point | Group 1 (Isotype Control) | | | Group 2 (Low) | | | Group 3 (Mid) | | | Group 4 (High) | | |
|---|---|---|---|---|---|---|---|---|---|---|---|---|
| | P0001 | P0002 | P0003 | P0101 | P0102 | P0103 | P0201 | P0202 | P0203 | P0301 | P0302 | P0303 |
| Pre-dose | 94 | 66 | 78 | 65 | 73 | 62 | 94 | 88 | 66 | 51 | 41 | 73 |
| 5 min | 76 | 59 | 70 | 53 | 60 | 54 | 68 | 73 | 61 | 37 | 31 | 52 |
| 24 h | 88 | 63 | 76 | 57 | 68 | 58 | 62 | 75 | 51 | 6* | 23 | 9* |

TABLE 15-continued

Quantitation of dosed monkey blood samples for C1q concentration by target peptide QTHQPPAPNSLIR (SEQ ID NO: 36) derived from C1q C subunit.
Concentration of C1q by Subunit C (μg/mL)

| Time Point | Group 1 (Isotype Control) | | | Group 2 (Low) | | | Group 3 (Mid) | | | Group 4 (High) | | |
|---|---|---|---|---|---|---|---|---|---|---|---|---|
| | P0001 | P0002 | P0003 | P0101 | P0102 | P0103 | P0201 | P0202 | P0203 | P0301 | P0302 | P0303 |
| 72 h | 87 | 58 | 64 | 57 | 61 | 54 | 69 | 70 | 54 | 7* | 24 | 12* |
| 168 h | 79 | 62 | 72 | 62 | 69 | 58 | 79 | 81 | 60 | 8* | 28 | 22 |
| D14 | 86 | 67 | 73 | 61 | 77 | 59 | 79 | 74 | 62 | 21 | 34 | 48 |
| D42 | 82 | 60 | 73 | 53 | 74 | 62 | 71 | 76 | 66 | 45 | 39 | 77 |
| D56 | 78 | 73 | 78 | 58 | 82 | 62 | 85 | 80 | 74 | 47 | 39 | 75 |

*An estimated C1q concentration. Concentration below LLOQ (0.27 μg/mL) but above LOD (0.027 μg/mL).

What is claimed is:

1. An assay comprising:
   (1) contacting a biological sample with at least one proteolytic enzyme to produce peptide fragments of the protein C1q present in the biological sample, wherein the peptide fragments of the protein C1q comprise:
      i) target peptides with an amino acid sequence of IAFSATR (SEQ ID NO:29);
      ii) target peptides with an amino acid sequence of SLGFCDTTNK (SEQ ID NO: 26), and
      iii) target peptides with an amino acid sequence of QTHOPPAPNSLIR (SEQ ID NO: 36); and
   (2) performing selected reaction monitoring mass spectrometry (SRM-MS) to measure the abundance of the target peptides, wherein the abundance of the target peptides determines the concentration of C1q in the biological sample.

2. The assay of claim 1, further comprising between step (1) and step (2), adding to the biological sample at least one labeled, synthetic C1q peptide fragment comprising an amino acid sequence identical to the amino acid sequence of at least one of the target peptides.

3. The assay of claim 1, wherein measuring the abundance of the target peptides comprises comparing a signal corresponding to the target peptides generated by SRM-MS to a standard curve.

4. The assay of claim 1, wherein the biological sample is a blood sample.

5. The assay of claim 1, wherein the biological sample is a human sample or a non-human primate sample.

6. The assay of claim 1, wherein the selected reaction monitoring mass spectrometry is LC-SRM-MS/MS.

7. The assay of claim 1, wherein the at least one proteolytic enzyme is trypsin.

8. The assay of claim 3, wherein the standard curve is produced using a method comprising:
   (a) preparing at least two C1q concentration standards by mixing known quantities of purified C1q protein and C1q-depleted serum;
   (b) adding to the at least two C1q concentration standards labeled, synthetic peptide fragments with amino acid sequences identical to the target peptides;
   (c) contacting the at least two labeled C1q concentration standards with a proteolytic enzyme to produce the target peptides;
   (d) performing selected reaction monitoring mass spectrometry to determine the strength of the signal that corresponds to the target peptides and the strength of the signal that corresponds to the labeled, synthetic peptide fragments in each of the at least two labeled C1q concentration standards; and
   (e) determining a standard curve using the signals and the known quantities of C1q protein.

* * * * *

```
                              SEQUENCE LISTING

Sequence total quantity: 41
SEQ ID NO: 1            moltype = AA   length = 245
FEATURE                 Location/Qualifiers
source                  1..245
                        mol_type = protein
                        organism = Homo sapiens
SEQUENCE: 1
MEGPRGWLVL CVLAISLASM VTEDLCRAPD GKKGEAGRPG RRGRPGLKGE QGEPGAPGIR   60
TGIQGLKGDQ GEPGPSGNPG KVGYPGPSGP LGARGIPGIK GTKGSPGNIK DQPRPAFSAI  120
RRNPPMGGNV VIFDTVITNQ EEPYQNHSGR FVCTVPGYYY FTFQVLSQWE ICLSIVSSSR  180
GQVRRSLGFC DTTNKGLFQV VSGGMVLQLQ QGDQVWVEKD PKKGHIYQGS EADSVFSGFL  240
IFPSA                                                              245

SEQ ID NO: 2            moltype = AA   length = 253
FEATURE                 Location/Qualifiers
source                  1..253
                        mol_type = protein
                        organism = Homo sapiens
SEQUENCE: 2
MMMKIPWGSI PVLMLLLLLG LIDISQAQLS CTGPPAIPGI PGIPGTPGPD GQPGTPGIKG   60
EKGLPGLAGD HGEFGEKGDP GIPGNPGKVG PKGPMGPKGG PGAPGAPGPK GESGDYKATQ  120
KIAFSATRTI NVPLRRDQTI RFDHVITNMN NNYEPRSGKF TCKVPGLYYF TYHASSRGNL  180
CVNLMRGRER AQKVVTFCDY AYNTFQVTTG GMVLKLEQGE NVFLQATDKN SLLGMEGANS  240
IFSGFLLFPD MEA                                                    253

SEQ ID NO: 3            moltype = AA   length = 245
FEATURE                 Location/Qualifiers
source                  1..245
                        mol_type = protein
                        organism = Homo sapiens
SEQUENCE: 3
MDVGPSSLPH LGLKLLLLLL LLPLRGQANT GCYGIPGMPG LPGAPGKDGY DGLPGPKGEP   60
GIPAIPGIRG PKGQKGEPGL PGHPGKNGPM GPPGMPGVPG PMGIPGEPGE EGRYKQKFQS  120
VPFTVTRQTH QPPAPNSLIRF NAVLTNPQGD YDTSTGKFTC KVPGLYYFVY HASHTANLCV  180
LLYRSGVKVV TFCGHTSKTN QVNSGGVLLR LQVGEEVWLA VNDYYDMVGI QGSDSVFSGF  240
LLFPD                                                              245

SEQ ID NO: 4            moltype = AA   length = 245
FEATURE                 Location/Qualifiers
source                  1..245
                        mol_type = protein
                        organism = Macaca fascicularis
SEQUENCE: 4
MEGPQGWLVV CVLAISLASI VTQNVCRAPD GKNGVAGRPG RPGRPGLKGE RGEPGAPGIR   60
TGIQGLKGDQ GEPGPSGNPG KVGYPGPSGP LGDRGIPGIK GIKGNPGNIK DQPRPAFSAI  120
RRNPPMGGNV VIFDMVITNQ EEPYQNHSGR FVCTVPGYYY FTFQVVSERE ICLSIVSSSR  180
GQVRRSLGFC DTTNKGLFQV VSGGMVLQLQ RGDQVWVEKD PRKGNIYQGL EADSVFSGFL  240
IFPSS                                                              245

SEQ ID NO: 5            moltype = AA   length = 253
FEATURE                 Location/Qualifiers
source                  1..253
                        mol_type = protein
                        organism = Macaca fascicularis
SEQUENCE: 5
MMMKILWGSI PVLMLLLLLG LLDVSWAQGS CTGPPAIPGT PGIPGTPGSD GQPGTPGIKG   60
EKGLPGLAGD HGEFGEKGDP GIPGNPGKVG PKGPMGPKGG PGAPGAPGPK GESGDYKATQ  120
```

```
KIAFSATRTV NTPLRRDQTI RFDHVITNMN NNYEPRSGKF TCRVPGLYYF TYHASSRGNL  180
CVKLMRGRER PQKVVTFCDY AYNTFQVTTG GMVLKLEQGE NVFLQATDKN SLLGMEGANS  240
IFSGFLLFPD VEA                                                    253

SEQ ID NO: 6              moltype = AA  length = 245
FEATURE                   Location/Qualifiers
source                    1..245
                          mol_type = protein
                          organism = Macaca fascicularis
SEQUENCE: 6
MDVGPSSLPH LGLKLLLLLL LLPLRGQANT GCYGIPGMPG LPGAPGKDGH DGLPGPKGEP   60
GIPAIPGTRG PKGQKGEPGT PGHPGKNGPM GPPGMPGVPG PMGIPGEPGE EGRYKQKYQS  120
VFTVARQTHQ PPAPNSLIRF NAVLTNPQGD YDTSTGKFTC KVPGLYYFVY HASHTANLCV  180
LLYRGGVKVV TFCGHTSQAN QVNSGGVLLR LQVGEEVWLG VNDYYDMVGI QGSDSVFSGF  240
LLFPD                                                             245

SEQ ID NO: 7              moltype = AA  length = 245
FEATURE                   Location/Qualifiers
source                    1..245
                          mol_type = protein
                          organism = Macaca mulatta
SEQUENCE: 7
MEGPQGWLVV CVLAISLASI VTQNVCRAPD GKNGVAGRPG RPGRPGLKGE RGEPGAPGIR   60
TGIQGLKGDQ GEPGPSGNPG KVGYPGPSGP LGDRGIPGIK GIKGNPGNIK DQPRPAFSAI  120
RRNPPMGGNV VIFDMVITNQ EEPYQNHSGR FVCTVPGYYY FTFQVVSERE ICLSIVSSSR  180
GQVRRSLGFC DTTNKGLFQV VSGGMVLQLQ RGDQVWVEKD PRKGNIYQGL EADSVFSGFL  240
IFPST                                                             245

SEQ ID NO: 8              moltype = AA  length = 253
FEATURE                   Location/Qualifiers
source                    1..253
                          mol_type = protein
                          organism = Macaca mulatta
SEQUENCE: 8
MMMKILWGSI PVLMLLLLLG LLDVSWAQGS CTGPPAIPGT PGIPGTPGSD GQPGTPGIKG   60
EKGLPGLAGD HGEFGEKGDP GIPGNPGKVG PKGPMGPKGG PGAPGAPGPK GESGDYKATQ  120
KIAFSATRTI NTPLRRDQTI RFDHVITNMN NNYEPRSGKF TCRVPGLYYF TYHASSRGNL  180
CVKLMRGRER PQKVVTFCDY AYNTFQVTTG GMVLKLEQGE NVFLQATDKN SLLGMEGANS  240
IFSGFLLFPD VEA                                                    253

SEQ ID NO: 9              moltype = AA  length = 245
FEATURE                   Location/Qualifiers
source                    1..245
                          mol_type = protein
                          organism = Macaca mulatta
SEQUENCE: 9
MDVGPSSLPH LGLKLLLLLL LLPLRGQANT GCYGIPGMPG LPGAPGKDGH DGLPGPKGEP   60
GIPAIPGTRG PKGQKGEPGT PGHPGKNGPM GPPGMPGVPG PMGIPGEPGE EGRYKQKYQS  120
VFTVARQTHQ PPAPNSLIRF NAVLTNPQGD YDTSTGKFTC KVPGLYYFVY HASHTANLCV  180
LLYRGGVKVV TFCGHTSQAN QVNSGGVLLR LQVGEEVWLG VNDYYDMVGI QGSDSVFSGF  240
LLFPD                                                             245

SEQ ID NO: 10             moltype = AA  length = 245
FEATURE                   Location/Qualifiers
source                    1..245
                          mol_type = protein
                          organism = Mus musculus
SEQUENCE: 10
METSQGWLVA CVLTMTLVWT VAEDVCRAPN GKDGAPGNPG RPGRPGLKGE RGEPGAAGIR   60
TGIRGFKGDP GESGPPGKPG NVGLPGPSGP LGDSGPQGLK GVKGNPGNIR DQPRPAFSAI  120
RQNPMTLGNV VIFDKVLTNQ ESPYQNHTGR FICAVPGFYY FNFQVISKWD LCLFIKSSSG  180
GQPRDSLSFS NTNNKGLFQV LAGGTVLQLR RGDEVWIEKD PAKGRIYQGT EADSIFSGFL  240
IFPSA                                                             245

SEQ ID NO: 11             moltype = AA  length = 253
FEATURE                   Location/Qualifiers
source                    1..253
                          mol_type = protein
                          organism = Mus musculus
SEQUENCE: 11
MKTQWGEVWT HLLLLLLGFL HVSWAQSSCT GPPGIPGIPG VPGVPGSDGQ PGTPGIKGEK   60
GLPGLAGDLG EFGEKGDPGI PGTPGKVGPK GPVGPKGTPG PSGPRGPKGD SGDYGATQKV  120
AFSALRTINS PLRPNQVIRF EKVITNANEN YEPRNGKFTC KVPGLYYFTY HASSRGNLCV  180
NLVRGRDRDS MQKVVTFCDY AQNTFQVTTG GVVLKLEQEE VVHLQATDKN SLLGIEGANS  240
IFTGFLLFPD MDA                                                    253

SEQ ID NO: 12             moltype = AA  length = 246
FEATURE                   Location/Qualifiers
source                    1..246
```

-continued

```
                        mol_type = protein
                        organism = Mus musculus
SEQUENCE: 12
MVVGPSCQPP CGLCLLLLFL LALPLRSQAS AGCYGIPGMP GMPGAPGKDG HDGLQGPKGE    60
PGIPAVPGTR GPKGQKGEPG MPGHRGKNGP RGTSGLPGDP GPRGPPGEPG VEGRYKQKHQ   120
SVFTVTRQTT QYPEANALVR FNSVVTNPQG HYNPSTGKFT CEVPGLYYFV YYTSHTANLC   180
VHLNLNLARV ASFCDHMFNS KQVSSGGVLL RLQRGDEVWL SVNDYNGMVG IEGSNSVFSG   240
FLLFPD                                                              246

SEQ ID NO: 13           moltype = AA   length = 245
FEATURE                 Location/Qualifiers
source                  1..245
                        mol_type = protein
                        organism = Rattus norvegicus
SEQUENCE: 13
METSQGWLVA CVLAVTLVWT VAEDVCRAPN GKDGVAGIPG RPGRPGLKGE RGEPGAAGIR    60
TGIRGLKGDM GESGPPGKPG NVGFPGPTGP LGNSGPQGLK GVKGNPGNIR DQPRPAFSAI   120
RQNPPTYGNV VVFDKVLTNQ ENPYQNRTGH FICAVPGFYY FTFQVISKWD LCLSIVSSSR   180
GQPRNSLGFC DTNSKGLFQV LAGGTVLQLQ RGDEVWIEKD PAKGRIYQGT EADSIFSGFL   240
IFPSA                                                               245

SEQ ID NO: 14           moltype = AA   length = 253
FEATURE                 Location/Qualifiers
source                  1..253
                        mol_type = protein
                        organism = Rattus norvegicus
SEQUENCE: 14
MKTQWSEILT PLLLLLLGLL HVSWAQSSCT GSPGIPGVPG IPGVPGSDGK PGTPGIKGEK    60
GLPGLAGDHG ELGEKGDAGI PGIPGKVGPK GPVGPKGAPG PPGPRGPKGG SGDYKATQKV   120
AFSALRTVNS ALRPNQAIRF EKVITNVNDN YEPRSGKFTC KVPGLYYFTY HASSRGNLCV   180
NIVRGRDRDR MQKVLTFCDY AQNTFQVTTG GVVLKLEQEE VVHLQATDKN SLLGVEGANS   240
IFTGFLLFPD MDV                                                      253

SEQ ID NO: 15           moltype = AA   length = 245
FEATURE                 Location/Qualifiers
source                  1..245
                        mol_type = protein
                        organism = Rattus norvegicus
SEQUENCE: 15
MVVGTSCQPQ HGLYLLLLLL ALPLRSQANA GCYGIPGMPG LPGTPGKDGH DGLQGPKGEP    60
GIPAIPGTQG PKGQKGEPGM PGHRGKNGPM GTSGSPGDPG PRGPPGEPGE EGRYKQKHS    120
VFTVTRQTAQ YPAANGLVKF NSAITNPQGD YNTNTGKFTC KVPGLYYFVH HTSQTANLCV   180
QLLLNNAKVT SFCDHMSNSK QVSSGGVLLR LQRGDEVWLA VNDYNGMVGT EGSDSVFSGF   240
LLFPD                                                               245

SEQ ID NO: 16           moltype = AA   length = 245
FEATURE                 Location/Qualifiers
source                  1..245
                        mol_type = protein
                        organism = Canis lupus
SEQUENCE: 16
MEAPWGWLAL CVLATSLASA VTQDVCRALD GRDGAAGTPG RPGRPGLKGE QGEPGAPGMR    60
TGIRGLKGDQ GDPGPPGNPG NMGFPGPSGL MGLPGIPGRR GPKGNPGNIR DQPRPAFSAI   120
RRNPPTGGNV VIFDTVITNQ EGPYQNHSGR FICAVPGYYY FTFQVSKWD  ICLSIVSSGR   180
AQIRRSLGFC DTNSKGIFQV VSGGMALQLQ QGDQVWIEKD PIKGRIYQGP EADSIFSGFL   240
IFPSL                                                               245

SEQ ID NO: 17           moltype = AA   length = 250
FEATURE                 Location/Qualifiers
source                  1..250
                        mol_type = protein
                        organism = Canis lupus
SEQUENCE: 17
MKTPRGGILA LLLPLLLGLL EVSWAQSCTG HPAIPGIPGI PGAPGTDGTP GTPGTKGEKG    60
LPGLAGDHGE FGEKGDPGIP GTPGKVGPKG PVGPKGSPGP PGARGAKGES GDYKATQKIA   120
FSAMRTINIP LRRDQTIRFD HIVTNENRNY EPRSGKFTCN VPGIYYFAYH ASSRGNLCVN   180
VMRGRERMQK VVTFCDYVQN TFQVTTGSVV LKLSQGENVY LQATDKNSLL GMEGANSIFS   240
GFLLFPDAEA                                                          250

SEQ ID NO: 18           moltype = AA   length = 245
FEATURE                 Location/Qualifiers
source                  1..245
                        mol_type = protein
                        organism = Canis lupus
SEQUENCE: 18
MDTGPSSWPH LGLNLLLLLL ALPLGGQAST GCYGIPGMPG LPGAPGKDGH DGLPGPKGEP    60
GIPAIPGTRG PKGQKGEPGT PGYPGKNGPM GTPGIPGVPG PVGPPGEPGE EGRYKQKHS    120
VFTVTRQTAQ YPLANNLVKF NTVITNPQGD YDTSTGKFTC KVPGLYYFVY HTSLTSNLCV   180
HLYRSGTRVT TFCDHMSNSK QVSSGGVLLR LQMGEQVWLA VNDYNGMVGT EGSDSVFSGF   240
```

```
LLFPD                                                                                                   245

SEQ ID NO: 19             moltype = AA  length = 247
FEATURE                   Location/Qualifiers
source                    1..247
                          mol_type = protein
                          organism = Danio rerio
SEQUENCE: 19
MQPSAFFAFL WAGALFPFSF CQDECVKHGR NGADGPNGRD GLPGPKGEKG EPALQVKLSS          60
IALEELKGDM GVRGPPGEPG LEGLMGAIGP RGPLGPAGPR GSSVGADGAK ASEKPAFSVL        120
RNEASQAQYK QPVTFNDKLS DANDDFQIKT GYFTCKVPGV YYFVFHASSE GRLCLRLKST        180
SAPPVSLSFC DFNSKSVSLV VSGGAVLTLL KGDKVWIEPF AGDGGVGQMP KRLYAVFNGF        240
LIYRNAE                                                                                                 247

SEQ ID NO: 20             moltype = AA  length = 242
FEATURE                   Location/Qualifiers
source                    1..242
                          mol_type = protein
                          organism = Danio rerio
SEQUENCE: 20
MLFALMSAHV VPQLAIMLLL VTSSMSETCA GNKGFPGTPG IPGVPGTDGK DGAKGEKGDP          60
GENEVQMTGP KGDPGKPGLP GRPGVKGPEG PQGPPGPGPE KGQRGVLSGK VAPDQYFVFS        120
YKKSQKLEKI LQDKLVVFDV PLITGIDGVL DGEGYFDVTI TGMYYISYQI SFQQSACLKI        180
QIGAEEKVKF CDSPKLILGT AASVVLKLNK GDKVSVQSTG ESTVFSRDTD CTFTGFMLFP        240
IK                                                                                                      242

SEQ ID NO: 21             moltype = AA  length = 244
FEATURE                   Location/Qualifiers
source                    1..244
                          mol_type = protein
                          organism = Danio rerio
SEQUENCE: 21
MFGGHLILVS LLSASLCLCL ASADTCPAGA MPGLPGIPGF PGRDGRQGMK GEKGDLGIPI          60
KPGDTVKKGE RGAFGLKGPP GKRGPHGDPG IMGPPGPPGE PGEAGLVDVS GSQLQSAFSV        120
SRHTRIPPDA NKVIRFSKVI TNPQGHFSTD ESKFVCKIPG TYYFVLHASS HDKKLCVILV        180
HDDKNLVSFC DHTQRGSQQV SSGGLSLYLK ENEKVWLMTN ALNGMYATAD RADSVFSGFL        240
IHAH                                                                                                    244

SEQ ID NO: 22             moltype = AA  length = 13
FEATURE                   Location/Qualifiers
source                    1..13
                          mol_type = protein
                          organism = Macaca fascicularis
SEQUENCE: 22
VGYPGPSGPL GAR                                                                                           13

SEQ ID NO: 23             moltype = AA  length = 11
FEATURE                   Location/Qualifiers
source                    1..11
                          mol_type = protein
                          organism = Macaca fascicularis
SEQUENCE: 23
DQPRPAFSAI R                                                                                             11

SEQ ID NO: 24             moltype = AA  length = 28
FEATURE                   Location/Qualifiers
source                    1..28
                          mol_type = protein
                          organism = Macaca fascicularis
SEQUENCE: 24
NPPMGGNVVI FDTVITNQEE PYQNHSGR                                                                           28

SEQ ID NO: 25             moltype = AA  length = 30
FEATURE                   Location/Qualifiers
source                    1..30
                          mol_type = protein
                          organism = Macaca fascicularis
SEQUENCE: 25
FVCTVPGYYY FTFQVLSQWE ICLSIVSSSR                                                                         30

SEQ ID NO: 26             moltype = AA  length = 10
FEATURE                   Location/Qualifiers
source                    1..10
                          mol_type = protein
                          organism = Macaca fascicularis
SEQUENCE: 26
SLGFCDTTNK                                                                                               10

SEQ ID NO: 27             moltype = AA  length = 26
```

```
FEATURE                 Location/Qualifiers
source                  1..26
                        mol_type = protein
                        organism = Macaca fascicularis
SEQUENCE: 27
GLFVVSGGMV LQLQQGDQVW VEKDPK                                         26

SEQ ID NO: 28           moltype = AA  length = 22
FEATURE                 Location/Qualifiers
source                  1..22
                        mol_type = protein
                        organism = Macaca fascicularis
SEQUENCE: 28
GHIYQGSEAD SVFSGFLIFP SA                                             22

SEQ ID NO: 29           moltype = AA  length = 7
FEATURE                 Location/Qualifiers
source                  1..7
                        mol_type = protein
                        organism = Macaca fascicularis
SEQUENCE: 29
IAFSATR                                                              7

SEQ ID NO: 30           moltype = AA  length = 8
FEATURE                 Location/Qualifiers
source                  1..8
                        mol_type = protein
                        organism = Macaca fascicularis
SEQUENCE: 30
TINVPLRR                                                             8

SEQ ID NO: 31           moltype = AA  length = 15
FEATURE                 Location/Qualifiers
source                  1..15
                        mol_type = protein
                        organism = Macaca fascicularis
SEQUENCE: 31
FDHVITNMNN NYEPR                                                     15

SEQ ID NO: 32           moltype = AA  length = 14
FEATURE                 Location/Qualifiers
source                  1..14
                        mol_type = protein
                        organism = Macaca fascicularis
SEQUENCE: 32
VPGLYYFTYH ASSR                                                      14

SEQ ID NO: 33           moltype = AA  length = 9
FEATURE                 Location/Qualifiers
source                  1..9
                        mol_type = protein
                        organism = Macaca fascicularis
SEQUENCE: 33
GNLCVNLMR                                                            9

SEQ ID NO: 34           moltype = AA  length = 14
FEATURE                 Location/Qualifiers
source                  1..14
                        mol_type = protein
                        organism = Macaca fascicularis
SEQUENCE: 34
LEQGENVFLQ ATDK                                                      14

SEQ ID NO: 35           moltype = AA  length = 9
FEATURE                 Location/Qualifiers
source                  1..9
                        mol_type = protein
                        organism = Macaca fascicularis
SEQUENCE: 35
FQSVFTVTR                                                            9

SEQ ID NO: 36           moltype = AA  length = 13
FEATURE                 Location/Qualifiers
source                  1..13
                        mol_type = protein
                        organism = Macaca fascicularis
SEQUENCE: 36
QTHQPPAPNS LIR                                                       13
```

```
SEQ ID NO: 37            moltype = AA  length = 18
FEATURE                  Location/Qualifiers
source                   1..18
                         mol_type = protein
                         organism = Macaca fascicularis
SEQUENCE: 37
FNAVLTNPQG DYDTSTGK                                                       18

SEQ ID NO: 38            moltype = AA  length = 23
FEATURE                  Location/Qualifiers
source                   1..23
                         mol_type = protein
                         organism = Macaca fascicularis
SEQUENCE: 38
VPGLYYFVYH ASHTANLCVL LYR                                                 23

SEQ ID NO: 39            moltype = AA  length = 10
FEATURE                  Location/Qualifiers
source                   1..10
                         mol_type = protein
                         organism = Macaca fascicularis
SEQUENCE: 39
VVTFCGHTSK                                                                10

SEQ ID NO: 40            moltype = AA  length = 12
FEATURE                  Location/Qualifiers
source                   1..12
                         mol_type = protein
                         organism = Macaca fascicularis
SEQUENCE: 40
TNQVNSGGVL LR                                                             12

SEQ ID NO: 41            moltype = AA  length = 10
FEATURE                  Location/Qualifiers
source                   1..10
                         mol_type = protein
                         organism = synthetic construct
MOD_RES                  5
                         note = Carbamidomethylation
SEQUENCE: 41
SLGFCDTTNK                                                                10
```

UNITED STATES PATENT AND TRADEMARK OFFICE
CERTIFICATE OF CORRECTION

PATENT NO. : 12,196,761 B2
APPLICATION NO. : 18/175066
DATED : January 14, 2025
INVENTOR(S) : Sook Yen E et al.

Page 1 of 1

It is certified that error appears in the above-identified patent and that said Letters Patent is hereby corrected as shown below:

In the Claims

At Column 41, Claim 1, Line number 51:
"QTHOPPAPNSLIR (SEQ ID NO:36); and"

Should read:
-- QTHQPPAPNSLIR (SEQ ID NO:36); and --

Signed and Sealed this
Eleventh Day of February, 2025

Coke Morgan Stewart
*Acting Director of the United States Patent and Trademark Office*